(12) United States Patent
Koerber et al.

(10) Patent No.: US 9,085,541 B2
(45) Date of Patent: Jul. 21, 2015

(54) PROCESS FOR PRODUCING IMINE COMPOUNDS FOR COMBATING INVERTEBRATE PESTS

(75) Inventors: Karsten Koerber, Eppelheim (DE); Florian Kaiser, Mannheim (DE); Christian Rein, Mannheim (DE); Joachim Schmidt-Leithoff, Freiburg (DE); Wolfgang Von Deyn, Neustadt (DE); Prashant Deshmukh, Mannheim (DE); Arun Narine, Mannheim, DE (US); Joachim Dickhaut, Heidelberg (DE); Nina Gertrud Bandur, Mannheim (DE); Juergen Langewald, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/805,559

(22) PCT Filed: Jun. 22, 2011

(86) PCT No.: PCT/EP2011/060388
§ 371 (c)(1),
(2), (4) Date: Dec. 19, 2012

(87) PCT Pub. No.: WO2011/161130
PCT Pub. Date: Dec. 29, 2011

(65) Prior Publication Data
US 2013/0102462 A1    Apr. 25, 2013

Related U.S. Application Data

(60) Provisional application No. 61/357,623, filed on Jun. 23, 2010.

(30) Foreign Application Priority Data

Jun. 23, 2010  (EP) ..................................... 10167098
Jun. 24, 2010  (EP) ..................................... 10167255

(51) Int. Cl.
*C07D 261/02* (2006.01)
*C07D 261/04* (2006.01)
(Continued)

(52) U.S. Cl.
CPC ............. *C07D 261/04* (2013.01); *A01N 43/80* (2013.01); *A01N 47/34* (2013.01); *A01N 47/36* (2013.01);
(Continued)

(58) Field of Classification Search
CPC .................................................... C07D 261/08
USPC ......................................................... 548/240
See application file for complete search history.

(56) References Cited

U.S. PATENT DOCUMENTS

2007/0066617 A1    3/2007  Mita et al.
2009/0023923 A1    1/2009  Mizukoshi et al.
(Continued)

FOREIGN PATENT DOCUMENTS

EP       1932836      6/2008
JP       2007016017   1/2007
(Continued)

OTHER PUBLICATIONS

Dorwald F. A. (Side Reactions in Organic Synthesis, 2005, Wiley: VCH, Weinheim p. IX of Preface p. 1-15).*
(Continued)

*Primary Examiner* — Nizal Chandrakumar
(74) *Attorney, Agent, or Firm* — Brinks Gilson & Lione

(57) ABSTRACT

The present invention relates to a process for producing aromatic carbonyl compounds of formula I and aromatic imine compounds of formula III

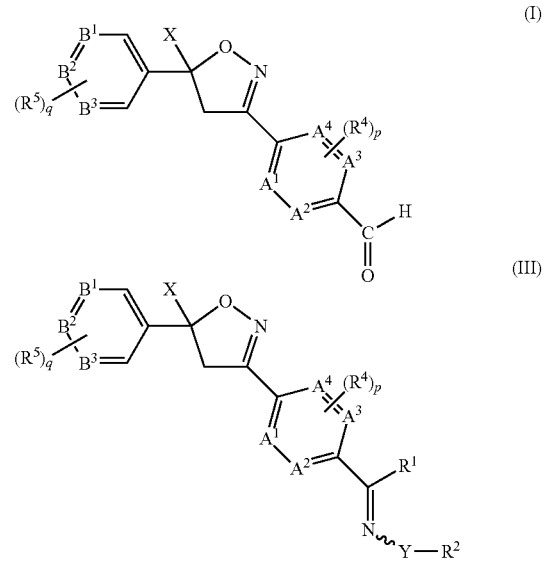

comprising the step of reacting a (hetero)aromatic halogen or sulfonate compound II

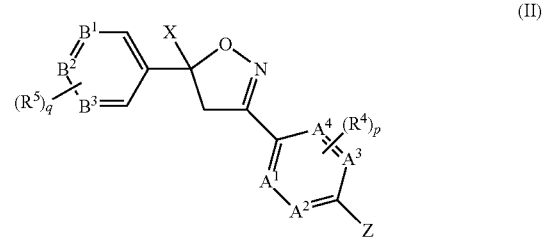

wherein the variables are as defined in the claims and description,
with a mixture of carbon monoxide and hydrogen in the presence of a transition metal complex catalyst. The invention also relates to specific compounds III, to compositions comprising them and to their use for combating invertebrate pests.

31 Claims, No Drawings

(51) Int. Cl.

| | | |
|---|---|---|
| *C07D 413/12* | (2006.01) | |
| *C07D 417/12* | (2006.01) | |
| *A01N 43/80* | (2006.01) | |
| *A01N 47/34* | (2006.01) | |
| *A01N 47/36* | (2006.01) | |
| *A01N 47/38* | (2006.01) | |
| *C07D 405/12* | (2006.01) | |
| *C07D 409/12* | (2006.01) | |

(52) U.S. Cl.
CPC .............. *A01N 47/38* (2013.01); *C07D 405/12* (2013.01); *C07D 409/12* (2013.01); *C07D 413/12* (2013.01); *C07D 417/12* (2013.01)

(56) References Cited

U.S. PATENT DOCUMENTS

| | | |
|---|---|---|
| 2010/0137612 A1 | 6/2010 | Yaosaka et al. |
| 2010/0144797 A1 | 6/2010 | Mita et al. |
| 2010/0174094 A1 | 7/2010 | Zierke et al. |
| 2011/0144349 A1 | 6/2011 | Kousaka et al. |
| 2011/0172414 A1 | 7/2011 | Mita et al. |
| 2011/0251398 A1 | 10/2011 | Mita et al. |

FOREIGN PATENT DOCUMENTS

| | | |
|---|---|---|
| JP | 2007106756 | 4/2007 |
| JP | 2008133242 | 6/2008 |
| JP | 2008156347 | 7/2008 |
| JP | 2008239611 | 10/2008 |
| WO | WO 2005085216 | 9/2005 |
| WO | WO 2007026965 | 3/2007 |
| WO | WO 2007070606 | 6/2007 |
| WO | WO 2007074789 | 7/2007 |
| WO | WO 2007075459 | 7/2007 |
| WO | WO 2007079162 | 7/2007 |
| WO | WO 2007105814 | 9/2007 |
| WO | WO 2007125984 | 11/2007 |
| WO | WO 2008012027 | 1/2008 |
| WO | WO 2008019760 | 2/2008 |
| WO | WO 2008108448 | 9/2008 |
| WO | WO 2008/122375 | 10/2008 |
| WO | WO 2008130651 | 10/2008 |
| WO | WO 2008145740 | 12/2008 |
| WO | WO 2008150393 | 12/2008 |
| WO | WO 2008154528 | 12/2008 |
| WO | WO 2009001942 | 12/2008 |
| WO | WO 2009002809 | 12/2008 |
| WO | WO 2009003075 | 12/2008 |
| WO | WO 2009024541 | 2/2009 |
| WO | WO 2009/049846 | 4/2009 |
| WO | WO 2009063910 | 5/2009 |
| WO | WO 2009126668 | 10/2009 |
| WO | WO 2009/142569 | 11/2009 |
| WO | WO 2010003877 | 1/2010 |
| WO | WO 2010003923 | 1/2010 |
| WO | WO 2010005048 | 1/2010 |
| WO | WO 2010/072781 | 7/2010 |
| WO | WO 2010/125130 | 11/2010 |
| WO | WO 2012/59441 | 5/2012 |
| WO | WO 2012/151512 | 11/2012 |

OTHER PUBLICATIONS

Office Action dated Dec. 26, 2013, in U.S. Appl. No. 13/266,265, filed Oct. 26, 2011.
Office Action dated May 28, 2013, in U.S. Appl. No. 13/266,265, filed Oct. 26, 2011.
Dorwald, "Side Reactions in Organic Synthesis," eds. Wiley, 2005, pp. 1-15, 279-308.
Hatanaka et al., "An Improved Synthesis of 4-[3-(Trifluoromethyl)-3H-Diazirin-3-YL]Benzoic Acid for Photoaffinity Labeling", Heterocycles, vol. 35, No. 2, (1993), pp. 997-1004.
Nader et al., "A Novel Fluoride Ion Mediated Olefination of Electron-Deficient Aryl Ketones by Alkanesulfonyl Halides", J. Org. Chem. vol. 59, (1994), pp. 2898-2901.
Doamaral et al., "AntiMalarial Activity of Guanyl Hydrazone Salts of Aromatic Ketones Part 2 Development of Active Poly Halo Derivatives," Journal of Medicinal Chemistry, vol. 14, No. 9, (1971), pp. 862-866.
Beech, "Preparation of Aromatic Aldehydes and Ketones from Diazonium Salts," Journal of the Chemical Society, (1954), pp. 1297-1302.
Jolad et al., "2-bromo-4-methylbenzaldehyde (p-tolualdehyde, 2-bromo-)," Organic Synthesis—Collective Volumes, eds. John Wiley and Sons, vol. 46, (1966), pp. 13-16.
International Search Report dated Oct. 27, 2011, prepared in International Application No. PCT/EP2011/060388.
International Preliminary Report on Patentability dated Dec. 28, 2012, prepared in International Application No. PCT/EP2011/060388.
Schoenberg, A., et al., "Palladium-Catalyzed Amidation of Aryl, Hereocyclic and Vinylic Halides", J. Org. Chem. 1974, p. 3327-3331, vol. 39, No. 23.
Barnard, Christopher, F.J., "Carbonylation of Aryl Halides: Extending the Scope of the Reaction", Organic Process Research & Deveopment, 2008, p. 566-574, vol. 12.
Fontán, Noelia, et al. "A conjunctive diiodoheptaene for the synthesis of $C_2$-symmetirc carotenoids", Chem Commun., 2013, p. 2964-2996, vol. 49, including Electronic Supplementary Material (ESI) for Chemical Communications.
Ulrich, Gilles, et al. "Carbonyl derivatives of Boradiazaindacene viacatalytic CO insertion", Journal of Organic Chemistry, 2012, p. 5036-5048, vol. 77.
Smith, M.B., and March J., March's Advanced Organic Chemistry: Reactions, mechanisms, and Structure, 5$^{th}$ Edition, 2001, Wiley & Sons, Inc., pp. 708-711, 929-931, 1239, and 1330-1339.
Friedel-Crafts reactions, accessed via http://en.wikipedia.org/wiki on Oct. 7, 2014.

* cited by examiner

PROCESS FOR PRODUCING IMINE COMPOUNDS FOR COMBATING INVERTEBRATE PESTS

This application is a National Stage application of International Application No. PCT/EP2011/060388, filed Jun. 22, 2011, which claims the benefit of U.S. Provisional Application No. 61/357,623, filed Jun. 23, 2010, the entire contents of which are hereby incorporated herein by reference. This application also claims priority under 35 U.S.C. §119 to European Patent Application No. 10167098.2, filed Jun. 23, 2010, and European Patent Application No. 10167255.8, filed Jun. 24, 2010, the entire contents of which is hereby incorporated herein by reference.

The present invention relates to a process for producing aromatic carbonyl compounds of formula I as defined below and aromatic imine compounds of formula III as defined below comprising the step of reacting a (hetero)aromatic halogen or sulfonate compound with a mixture of carbon monoxide and hydrogen in the presence of a transition metal complex catalyst.

Imine-substituted isoxazolines of the formula III defined below are useful for combating or controlling invertebrate pests, in particular arthropod pests and nematodes. Their preparation is however rather difficult and involves steps which are not feasible on an industrial scale.

For instance, WO 2010/072781 describes in example 1 the conversion of an aromatic bromide to the corresponding aldehyde with triethyl silane in the presence of a palladium catalyst. Triethyl silane is however not suitable for the use on an industrial scale. Moreover, the amount of palladium catalyst required in this conversion is rather high.

It was therefore an object of the present invention to provide a process for producing the aromatic carbonyl compound of formula I and eventually the imine product of formula III as defined below which can be applied on an industrial scale. Moreover, the process should require a smaller amount of catalyst.

The object is achieved by the finding that the (hetero) aromatic halogenide or sulfonate of formula II as defined below can be converted into the corresponding aldehyde by reaction with a mixture of CO and $H_2$ in the presence of a transition metal catalyst.

The invention thus relates to a process for producing a carbonyl compound of formula I

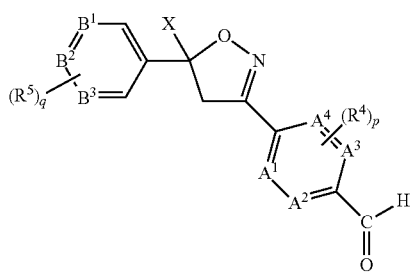

(I)

wherein $A^1$, $A^2$, $A^3$ and $A^4$ are N or CH, with the proviso that at most three of $A^1$, $A^2$, $A^3$ and $A^4$ are N;

$B^1$, $B^2$ and $B^3$ are N or CH, with the proviso that at most two of $B^1$, $B^2$ and $B^3$ are N;

X is selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl and $C_3$-$C_6$-halocycloalkyl;

each $R^4$ is independently selected from the group consisting of fluorine; chlorine; cyano; azido; nitro; —SCN; $SF_5$; $C_1$-$C_6$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_6$-alkenyl which may be partially or fully halogenated and/or may be substituted by one or more radicals $R^6$; $C_2$-$C_6$-alkynyl which may be partially or fully halogenated and/or may be substituted by one or more radicals $R^6$; —Si$(R^{14})_2R^{13}$; —OR$^7$; —SR$^7$; —S(O)$_m R^7$; —S(O)$_n$N$(R^8)R^9$; —N$(R^8)R^9$; —N$(R^8)$C(=O)R$^6$; C(=O)R$^6$; —C(=O)OR$^7$; —C(=NR$^8$)H; —C(=NR$^8$)R$^6$; —C(=O)N$(R^8)R^9$; C(=S)N$(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or two radicals $R^4$ bound on adjacent carbon atoms may be together a group selected from —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CHCH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^8$—, —CH$_2$CH=N—, —CH=CH—NR$^8$—, —OCH=N— and —SCH=N—, thus forming, together with the carbon atoms to which they are bound, a 5- or 6-membered ring, where the hydrogen atoms of the above groups may be replaced by one or more substituents selected from fluorine, chlorine, methyl, halomethyl, hydroxyl, methoxy and halomethoxy or one or more CH$_2$ groups of the above groups may be replaced by a C=O group;

each $R^5$ is independently selected from the group consisting of fluorine, chlorine, cyano, azido, nitro, —SCN, $SF_5$, $C_1$-$C_6$-alkyl which may be partially or fully halogenated and/or may be substituted by one or more radicals $R^6$, $C_3$-$C_8$-cycloalkyl which may be partially or fully halogenated and/or may be substituted by one or more radicals $R^6$, $C_2$-$C_6$-alkenyl which may be partially or fully halogenated and/or may be substituted by one or more radicals $R^6$, $C_2$-$C_6$-alkynyl which may be partially or fully halogenated and/or may be substituted by one or more radicals $R^6$, —Si$(R^{14})_2R^{13}$, —OR$^7$, —SR$^7$, —S(O)$_m R^7$, —S(O)$_n$N$(R^8)R^9$, —N$(R^8)R^9$, N$(R^8)$C(=O)R$^6$, —C(=O)R$^6$, —C(=O)OR$^7$, —C(=S)R$^6$, —C(=S)OR$^7$, —C(=NR$^8$)R$^6$, —C(=O)N$(R^8)R^9$, —C(=S)N$(R^8)R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

each $R^6$ is independently selected from the group consisting of cyano, azido, nitro, —SCN, $SF_5$, $C_3$-$C_8$-cycloalkyl, $C_3$-$C_8$-halocycloalkyl, —Si($R^{14}$)$_2R^{13}$, —$OR^7$, —$OSO_2R^7$, —$SR^7$, —S(O)$_mR^7$, —S(O)$_nN(R^8)R^9$, —$N(R^8)R^9$, —C(=O)$N(R^8)R^9$, —C(=S)$N(R^8)R^9$, —C(=O)$OR^7$, —C(=O)$R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; and, in case $R^6$ is bound to a cycloalkyl group or to a heterocyclic ring formed by $R^1$ and $R^2$ together with the atoms to which they are bound, $R^6$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$; and in groups —C(=O)$R^6$, —C(=S)$R^6$, —C(=$NR^8$)$R^6$ and —N($R^8$)C(=O)$R^6$, $R^6$ may additionally be selected from hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$;

or two geminally bound radicals $R^6$ together form a group selected from =$CR^{11}R^{12}$, =S(O)$_mR^7$, =S(O)$_mN(R^8)R^9$, =$NR^8$, =$NOR^7$ and =$NNR^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2R^{13}$, —$SR^8$, —S(O)$_mR^7$, —S(O)$_nN(R^8)R^9$, —$N(R^8)R^9$, —N=$CR^{15}R^{16}$, —C(=O)$R^{17}$, —C(=O)$N(R^8)R^9$, —C(=S)$N(R^8)R^9$, —C(=O)$OR^{17}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

with the proviso that $R^7$ is not $C_1$-$C_6$-alkoxy or $C_1$-$C_6$-haloalkoxy if it is bound to an oxygen atom;

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_mR^{20}$, —S(O)$_nN(R^{21})R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_mR^{20}$, —S(O)$_nN(R^{21})R^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^8$ and $R^9$ together form a group =$CR^{11}R^{12}$;

or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$;

each $R^{10}$ is independently selected from the group consisting of fluorine, chlorine, cyano, azido, nitro, —SCN, $SF_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —Si($R^{14}$)$_2R^{13}$, —$OR^{20}$, —$SR^{20}$, —S(O)$_mR^{20}$, —S(O)$_nN(R^{21})R^{22}$, —$N(R^{21})R^{22}$, C(=O)$R^{19}$, —C(=O)$OR^{20}$, —C(=$NR^{21}$)$R^{22}$, —C(=O)$N(R^{21})R^{22}$, —C(=S)$N(R^{21})R^{22}$, phenyl which may be substituted by 1, 2, 3, 4 or 5 radicals independently selected from fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —$CH_2CH_2CH_2CH_2$—, —CH=CH—CH=CH—, —N=CH—CH=CH—, —CH=N—CH=CH—, —N=CH—N=CH—, —$OCH_2CH_2CH_2$—, —OCH=$CHCH_2$—, —$CH_2OCH_2CH_2$—, —$OCH_2CH_2O$—, —OCH$_2$OCH$_2$—, —CH$_2$CH$_2$CH$_2$—, —CH═CHCH$_2$—, —CH$_2$CH$_2$O—, —CH═CHO—, —CH$_2$OCH$_2$—, —CH$_2$C(═O)O—, —C(═O)OCH$_2$—, —O(CH$_2$)O—, —SCH$_2$CH$_2$CH$_2$—, —SCH═CHCH$_2$—, —CH$_2$SCH$_2$CH$_2$—, —SCH$_2$CH$_2$S—, —SCH$_2$SCH$_2$—, —CH$_2$CH$_2$S—, —CH═CHS—, —CH$_2$SCH$_2$—, —CH$_2$C(═S)S—, —C(═S)SCH$_2$—, —S(CH$_2$)S—, —CH$_2$CH$_2$NR$^{21}$—, —CH$_2$CH═N—, —CH═CH—NR$^{21}$—, —OCH═N— and —SCH═N—, thus forming, together with the atoms to which they are bound, a 5- or 6-membered ring, where the hydrogen atoms of the above groups may be replaced by one or more substituents selected from fluorine, chlorine, methyl, halomethyl, hydroxyl, methoxy and halomethoxy or one or more CH$_2$ groups of the above groups may be replaced by a C═O group;

R$^{11}$, R$^{12}$ are, independently of each other and independently of each occurrence, selected from the group consisting of hydrogen, halogen, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy-C$_1$-C$_6$-alkyl, C$_1$-C$_6$-haloalkoxy-C$_1$-C$_6$-alkyl, C$_1$-C$_6$-alkoxy, C$_1$-C$_6$-haloalkoxy, —C(═O)R$^{19}$, —C(═O)OR$^{20}$, —C(═NR$^{21}$)R$^{22}$, —C(═O)N(R$^{21}$)R$^{22}$, —C(═S)N(R$^{21}$)R$^{22}$, phenyl which may be substituted by 1, 2, 3, 4, or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, which may be substituted by one or more radicals R$^{10}$;

R$^{13}$, R$^{14}$ are, independently of each other and independently of each occurrence, selected from the group consisting of C$_1$-C$_4$-alkyl, C$_3$-C$_6$-cycloalkyl, C$_1$-C$_4$-alkoxy-C$_1$-C$_4$-alkyl, phenyl and benzyl;

R$^{15}$, R$^{16}$ are, independently of each other and independently of each occurrence, selected from the group consisting of C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy-C$_1$-C$_6$-alkyl, C$_1$-C$_6$-haloalkoxy-C$_1$-C$_6$-alkyl, phenyl which may be substituted by 1, 2, 3, 4, or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, which may be substituted by one or more radicals R$^{10}$;

each R$^{17}$ is independently selected from the group consisting of C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C$_3$-C$_8$-cycloalkyl, C$_3$-C$_8$-halocycloalkyl, C$_1$-C$_6$-alkoxy-C$_1$-C$_6$-alkyl, C$_1$-C$_6$-haloalkoxy-C$_1$-C$_6$-alkyl, phenyl and benzyl;

each R$^{19}$ is independently selected from the group consisting of cyano, azido, nitro, —SCN, SF$_5$, C$_3$-C$_8$-cycloalkyl, C$_3$-C$_8$-halocycloalkyl, —Si(R$^{14}$)$_2$R$^{13}$, —OR$^{20}$, —OSO$_2$R$^{20}$, —SR$^{20}$, —S(O)$_m$R$^{20}$, —S(O)$_n$N(R$^{21}$)R$^{22}$, —N(R$^{21}$)R$^{22}$, —C(═O)N(R$^{21}$)R$^{22}$, —C(═S)N(R$^{21}$)R$^{22}$, —C(═O)OR$^{20}$, —C(═O)R$^{20}$, phenyl which may be substituted by 1, 2, 3, 4 or 5 radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy, and a 3-, 4-, 5-, 6- or 7-membered saturated, partially unsaturated or aromatic heteroaryl ring containing 1, 2 or 3 heteroatoms or heteroatom groups selected from N, O, S, NO, SO and SO$_2$, as ring members, where the heterocyclic ring may be substituted by one or more radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy;

and, in case R$^{19}$ is bound to a cycloalkyl group, R$^{19}$ may additionally be selected from the group consisting of C$_1$-C$_6$-alkyl, C$_1$-C$_6$-haloalkyl, C$_1$-C$_6$-alkoxy-C$_1$-C$_6$-alkyl, C$_2$-C$_6$-alkenyl, C$_2$-C$_6$-haloalkenyl, C$_2$-C$_6$-alkynyl and C$_2$-C$_6$-haloalkynyl; and in groups —C(═O)R$^{19}$, R$^{19}$ may additionally be selected from hydrogen, halogen, C$_1$-C$_6$-alkyl, C$_1$-C$_6$-haloalkyl, C$_1$-C$_6$-alkoxy-C$_1$-C$_6$-alkyl, C$_2$-C$_6$-alkenyl, C$_2$-C$_6$-haloalkenyl, C$_2$-C$_6$-alkynyl, and C$_2$-C$_6$-haloalkynyl;

or two geminally bound radicals R$^{19}$ together form a group selected from ═CR$^{11}$R$^{12}$, ═S(O)$_m$R$^{20}$, ═S(O)$_m$N(R$^{21}$)R$^{22}$, ═NR$^{21}$, ═NOR$^{20}$ and ═NNR$^{21}$;

or two radicals R$^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and SO$_2$, as ring members;

each R$^{20}$ is independently selected from the group consisting of hydrogen, cyano, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_1$-C$_6$-alkylsulfinyl, C$_1$-C$_6$-haloalkylsulfinyl, C$_1$-C$_6$-alkylsulfonyl, C$_1$-C$_6$-haloalkylsulfonyl, C$_3$-C$_8$-cycloalkyl, C$_3$-C$_8$-cycloalkyl-C$_1$-C$_4$-alkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, —Si(R$^{14}$)$_2$R$^{13}$, C$_1$-C$_6$-alkylaminosulfonyl, amino, C$_1$-C$_6$-alkylamino, di-(C$_1$-C$_6$-alkyl)-amino, C$_1$-C$_6$-alkylcarbonyl, C$_1$-C$_6$-haloalkylcarbonyl, aminocarbonyl, C$_1$-C$_6$-alkylaminocarbonyl, di-(C$_1$-C$_6$-alkyl)-aminocarbonyl, C$_1$-C$_6$-alkoxycarbonyl, C$_1$-C$_6$-haloalkoxycarbonyl, phenyl which may be substituted by 1, 2, 3, 4 or 5 radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy, benzyl which may be substituted by 1, 2, 3, 4 or 5 radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy;

with the proviso that R$^{20}$ is not C$_1$-C$_6$-alkoxy or C$_1$-C$_6$-haloalkoxy if it is bound to an oxygen atom;

R$^{21}$ and R$^{22}$ are independently of each other and independently of each occurrence selected from the group consisting of hydrogen, C$_1$-C$_6$-alkyl, C$_1$-C$_6$-haloalkyl, C$_1$-C$_6$-alkoxy, C$_1$-C$_6$-haloalkoxy, C$_1$-C$_6$-alkylthio, C$_1$-C$_6$-haloalkylthio, C$_3$-C$_8$-cycloalkyl, C$_3$-C$_8$-halocycloalkyl, C$_3$-C$_8$-cycloalkyl-C$_1$-C$_4$-alkyl, C$_2$-C$_6$-alkenyl, C$_2$-C$_6$-haloalkenyl, C$_2$-C$_6$-alkynyl, C$_2$-C$_6$-haloalkynyl, phenyl which may be substituted by 1, 2, 3, 4 or 5 radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy, benzyl which may be substituted by 1, 2, 3, 4 or 5 radicals independently selected from fluorine, chlorine, cyano, nitro, C$_1$-C$_6$-alkyl, C$_1$-C$_6$-haloalkyl, C$_1$-C$_6$-alkoxy and C$_1$-C$_6$-haloalkoxy, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals independently selected from fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from fluorine, chlorine, $C_1$-$C_6$-alkyl, $C_1$-$C_6$-haloalkyl, $C_1$-$C_6$-alkoxy and $C_1$-$C_6$-haloalkoxy;

each m is independently 1 or 2;
each n is independently 0, 1 or 2;
p is 0, 1, 2, 3 or 4; and
q is 0, 1 2, 3, 4 or 5;
comprising following step:
reacting a compound of formula II

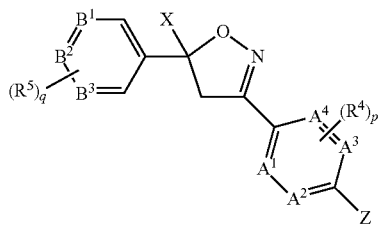

wherein $A^1$, $A^2$, $A^3$, $A^4$, $B^1$, $B^2$, $B^3$, X, $R^4$, $R^5$, p and q are as defined above and Z is selected from halogen and —$OSO_2$—$R^{z1}$, where $R^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy;

with carbon monoxide and hydrogen in the presence of a transition metal complex.

This process is called process A.

The invention also relates to a process for producing imine compounds of the formula III

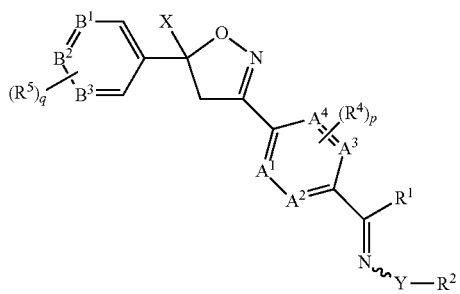

wherein
Y is O, N—$R^3$, $S(O)_n$ or a chemical bond;
$R^1$ is selected from the group consisting of hydrogen; cyano; $C_1$-$C_{10}$-alkyl which may be partially or fully halogenated and/or may be substituted by one or more radicals $R^6$; $C_1$-$C_{10}$-alkoxy; $C_1$-$C_{10}$-haloalkoxy; $C_1$-$C_{10}$-alkylthio; $C_1$-$C_{10}$-haloalkylthio; $C_1$-$C_{10}$-alkylsulfinyl; $C_1$-$C_{10}$-haloalkylsulfinyl; $C_1$-$C_{10}$-alkylsulfonyl; $C_1$-$C_{10}$-haloalkylsulfonyl; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a C-bound 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —N($R^8$)C(=O)$R^6$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$, —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

with the proviso that $R^2$ is not —O$R^7$ if Y is O;

or $R^1$ and $R^2$, together with the atoms to which they are bound, form a partially unsaturated or aromatic 5- or 6-membered heterocyclic ring which, apart from the nitrogen atom of the imine group and the group Y if this is different from a chemical bond, optionally contains 1 or 2 further heteroatoms or heteroatom groups selected from N, O, S, NO, SO and $SO_2$, as ring members, where the heterocyclic ring may carry 1, 2 or 3 substituents $R^6$;

$R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; —N($R^8$)$R^9$; —Si($R^{14}$)$_2$$R^{13}$; —O$R^7$; —S$R^7$; —S(O)$_m$$R^7$; —S(O)$_n$N($R^8$)$R^9$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;

or $R^2$ and $R^3$ together form a group =C$R^{11}$$R^{12}$; =S(O)$_m$$R^7$; =S(O)$_m$N($R^8$)$R^9$; =N$R^8$; or =NO$R^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or N$R^{18}$ and/or 1 or 2 of the $CH_2$ groups of the alkylene chain may be replaced by a group C=O, C=S and/or C=NR$^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$;
each R$^{18}$ is independently defined like R$^3$;
and A$^1$, A$^2$, A$^3$, A$^4$, B$^1$, B$^2$, B$^3$, X, R$^4$, R$^5$, R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{19}$, R$^{20}$, R$^{21}$, R$^{22}$, m, n, p and q are as defined in claim 1;
comprising following step:
reacting a compound of formula II

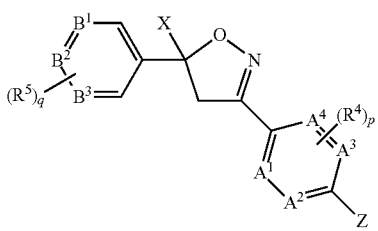

(II)

wherein A$^1$, A$^2$, A$^3$, A$^4$, B$^1$, B$^2$, B$^3$, X, R$^4$, R$^5$, p and q are as defined above and
Z is selected from halogen and —OSO$_2$—R$^{z1}$, where R$^{z1}$ is $C_1$-$C_4$-alkyl, $C_1$-$C_4$-haloalkyl or phenyl which may be substituted by 1, 2 or 3 radicals selected from $C_1$-$C_4$-alkyl, $C_1$-$C_4$-haloalkyl $C_1$-$C_4$-alkoxy or $C_1$-$C_4$-haloalkoxy;
with carbon monoxide and hydrogen in the presence of a transition metal complex catalyst.

This process is called process B.

The organic moieties mentioned in the above definitions of the variables are—like the term halogen—collective terms for individual listings of the individual group members. The prefix $C_n$-$C_m$ indicates in each case the possible number of carbon atoms in the group.

The term halogen denotes in each case fluorine, bromine, chlorine or iodine, in particular fluorine, chlorine or bromine.

The term "$C_1$-$C_{10}$-alkyl" as used herein and in the alkyl moieties of alkoxy, alkylthio, alkylsulfinyl, alkylsulfonyl, alkylcarbonyl, alkoxycarbonyl and the like refers to saturated straight-chain or branched hydrocarbon radicals having 1 to 2 ("$C_1$-$C_2$-alkyl"), 1 to 4 ("$C_1$-$C_4$-alkyl"), 1 to 6 ("$C_1$-$C_6$-alkyl"), 1 to 8 ("$C_1$-$C_8$-alkyl") or 1 to 10 ("$C_1$-$C_{10}$-alkyl") carbon atoms. $C_1$-$C_2$-Alkyl is methyl or ethyl. $C_1$-$C_4$-Alkyl is additionally propyl, isopropyl, butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl. $C_1$-$C_8$-Alkyl is additionally also, for example, heptyl, octyl, 2-ethylhexyl and positional isomers thereof. $C_1$-$C_{10}$-Alkyl is additionally also, for example, nonyl, decyl and positional isomers thereof.

The term "$C_1$-$C_{10}$-haloalkyl" as used herein, which is also expressed as "$C_1$-$C_{10}$-alkyl which is partially or fully halogenated", refers to straight-chain or branched alkyl groups having 1 to 2 ("$C_1$-$C_2$-haloalkyl"), 1 to 4 ("$C_1$-$C_4$-haloalkyl"), 1 to 6 ("$C_1$-$C_6$-haloalkyl"), 1 to 8 ("$C_1$-$C_8$-haloalkyl") or 1 to 10 ("$C_1$-$C_{10}$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl or 1,1,1-trifluoroprop-2-yl.

"Halomethyl" is methyl in which 1, 2 or 3 of the hydrogen atoms are replaced by halogen atoms. Examples are bromomethyl, chloromethyl, fluoromethyl, dichloromethyl, trichloromethyl, difluoromethyl, trifluoromethyl, chlorofluoromethyl, dichlorofluoromethyl, chlorodifluoromethyl and the like.

The term "$C_2$-$C_{10}$-alkenyl" as used herein and in the alkenyl moiety of alkenyloxy and the like refers to monounsaturated straight-chain or branched hydrocarbon radicals having 2 to 4 ("$C_2$-$C_4$-alkenyl"), 2 to 6 ("$C_2$-$C_6$-alkenyl"), 2 to 8 ("$C_2$-$C_8$-alkenyl"), 3 to 8 ("$C_3$-$C_8$-alkenyl"), 2 to 10 ("$C_2$-$C_{10}$-alkenyl") or 3 to 10 ("$C_3$-$C_{10}$-alkenyl") carbon atoms and a double bond in any position, for example $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like, or $C_2$-$C_{10}$-alkenyl, such as the radicals mentioned for $C_2$-$C_6$-alkenyl and additionally 1-heptenyl, 2-heptenyl, 3-heptenyl, 1-octenyl, 2-octenyl, 3-octenyl, 4-octenyl, 1-nonenyl, 2-nonenyl, 3-nonenyl, 4-nonenyl, 1-decenyl, 2-decenyl, 3-decenyl, 4-decenyl, 5-decenyl and the positional isomers thereof.

The term "$C_2$-$C_{10}$-haloalkenyl" as used herein, which is also expressed as "$C_1$-$C_{10}$-alkenyl which is partially or fully halogenated", and the haloalkenyl moieties in haloalkenyloxy, haloalkenylcarbonyl and the like refers to unsaturated straight-chain or branched hydrocarbon radicals having 2 to 4 ("$C_2$-$C_4$-haloalkenyl"), 2 to 6 ("$C_2$-$C_6$-haloalkenyl"), 2 to 8 ("$C_2$-$C_6$-haloalkenyl") or 2 to 10 ("$C_2$-$C_{10}$-haloalkenyl") carbon atoms and a double bond in any position (as mentioned above), where some or all of the hydrogen atoms in these groups are replaced by halogen atoms as mentioned above, in particular fluorine, chlorine and bromine, for example chlorovinyl, chloroallyl and the like.

The term "$C_2$-$C_{10}$-alkynyl" as used herein and the alkynyl moieties in alkynyloxy, alkynylcarbonyl and the like refers to straight-chain or branched hydrocarbon groups having 2 to 4 ("$C_2$-$C_4$-alkynyl"), 2 to 6 ("$C_2$-$C_6$-alkynyl"), 2 to 8 ("$C_2$-$C_8$-alkynyl"), 3 to 8 ("$C_3$-$C_8$-alkynyl"), 2 to 10 ("$C_2$-$C_{10}$-alkynyl") or 3 to 10 ("$C_3$-$C_8$-alkynyl") carbon atoms and one or two triple bonds in any position, for example $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "$C_2$-$C_{10}$-haloalkynyl" as used herein, which is also expressed as "$C_1$-$C_{10}$-alkynyl which is partially or fully halogenated", and the haloalkynyl moieties in haloalkynyloxy, haloalkynylcarbonyl and the like refers to unsaturated straight-chain or branched hydrocarbon radicals having 2 to 4 ("$C_2$-$C_4$-haloalkynyl"), 3 to 4 ("$C_3$-$C_4$-haloalkynyl"), 2 to 6 ("$C_2$-$C_6$-haloalkynyl"), 3 to 6 ("$C_3$-$C_6$-haloalkynyl"), 2 to 8 ("$C_2$-$C_8$-haloalkynyl"), 3 to 8 ("$C_3$-$C_8$-haloalkynyl"), 2 to 10 ("$C_2$-$C_{10}$-haloalkynyl") or 3 to 10 ("$C_3$-$C_{10}$-haloalkynyl") carbon atoms and one or two triple bonds in any position (as mentioned above), where some or all of the hydrogen atoms in these groups are replaced by halogen atoms as mentioned above, in particular fluorine, chlorine and bromine;

The term "$C_3$-$C_8$-cycloalkyl" as used herein refers to mono- or bi- or polycyclic saturated hydrocarbon radicals having 3 to 8, in particular 3 to 6 carbon atoms ("$C_3$-$C_6$-cycloalkyl"). Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl.

The term "$C_3$-$C_8$-halocycloalkyl" as used herein, which is also expressed as "$C_3$-$C_8$-cycloalkyl which is partially or fully halogenated", and the halocycloalkyl moieties in halocycloalkoxy, halocycloalkylcarbonyl and the like refers to mono- or bi- or polycyclic saturated hydrocarbon groups having 3 to 8 ("$C_3$-$C_8$-halocycloalkyl") or preferably 3 to 6 ("$C_3$-$C_6$-halocycloalkyl") carbon ring members (as mentioned above) in which some or all of the hydrogen atoms are replaced by halogen atoms as mentioned above, in particular fluorine, chlorine and bromine.

The term "$C_3$-$C_8$-cycloalkyl-$C_1$-$C_4$-alkyl" refers to a $C_3$-$C_8$-cycloalkyl group as defined above which is bound to the remainder of the molecule via a $C_1$-$C_4$-alkyl group, as defined above. Examples are cyclopropylmethyl, cyclopropylethyl, cyclopropylpropyl, cyclobutylmethyl, cyclobutylethyl, cyclobutylpropyl, cyclopentylmethyl, cycloppentylethyl, cyclopentylpropyl, cyclohexylmethyl, cyclohexylethyl, cyclohexylpropyl, and the like.

The term "$C_1$-$C_2$-alkoxy" is a $C_1$-$C_2$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is methoxy or ethoxy. $C_1$-$C_4$-Alkoxy is additionally, for example, n-propoxy, 1-methylethoxy (isopropoxy), butoxy, 1-methylpropoxy (sec-butoxy), 2-methylpropoxy (isobutoxy) or 1,1-dimethylethoxy (tertbutoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. The term "$C_1$-$C_{10}$-haloalkoxy" is a $C_1$-$C_{10}$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_4$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy, 1-($CH_2Br$)-2-bromoethoxy, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromhexoxy, 6-iodohexoxy or dodecafluorohexoxy.

The term "$C_1$-$C_2$-alkylthio" is a $C_1$-$C_2$-alkyl group, as defined above, attached via a sulfur atom. The term "$C_1$-$C_4$-alkylthio" is a $C_1$-$C_4$-alkyl group, as defined above, attached via a sulfur atom. The term "$C_1$-$C_6$-alkylthio" is a $C_1$-$C_6$-alkyl group, as defined above, attached via a sulfur atom. The term "$C_1$-$C_{10}$-alkylthio" is a $C_1$-$C_{10}$-alkyl group, as defined above, attached via a sulfur atom. $C_1$-$C_2$-Alkylthio is methylthio or ethylthio. $C_1$-$C_4$-Alkylthio is additionally, for example, n-propylthio, 1-methylethylthio (isopropylthio), butylthio, 1-methylpropylthio (sec-butylthio), 2-methylpropylthio (isobutylthio) or 1,1-dimethylethylthio (tert-butylthio). $C_1$-$C_6$-Alkylthio is additionally, for example, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio or 1-ethyl-2-methylpropylthio. $C_1$-$C_8$-Alkylthio is additionally, for example, heptylthio, octylthio, 2-ethylhexylthio and positional isomers thereof. $C_1$-$C_{10}$-Alkylthio is additionally, for example, nonylthio, decylthio and positional isomers thereof.

The term "$C_1$-$C_2$-haloalkylthio" is a $C_1$-$C_2$-haloalkyl group, as defined above, attached via a sulfur atom. The term "$C_1$-$C_4$-haloalkylthio" is a $C_1$-$C_4$-haloalkyl group, as defined above, attached via a sulfur atom. The term "$C_1$-$C_6$-haloalkylthio" is a $C_1$-$C_6$-haloalkyl group, as defined above, attached via a sulfur atom. The term "$C_1$-$C_{10}$-haloalkylthio" is a $C_1$-$C_{10}$-haloalkyl group, as defined above, attached via a sulfur atom. $C_1$-$C_2$-Haloalkylthio is, for example, $SCH_2F$, $SCHF_2$, $SCF_3$, $SCH_2Cl$, $SCHC_2$, $SCCl_3$, chlorofluoromethylthio, dichlorofluoromethylthio, chlorodifluoromethylthio, 2-fluoroethylthio, 2-chloroethylthio, 2-bromoethylthio, 2-iodoethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio or $SC_2F_5$. $C_1$-$C_4$-Haloalkylthio is additionally, for example, 2-fluoropropylthio, 3-fluoropropylthio, 2,2-difluoropropylthio, 2,3-difluoropropylthio, 2-chloropropylthio, 3-chloropropylthio, 2,3-dichloropropylthio, 2-bromopropylthio, 3-bromopropylthio, 3,3,3-trifluoropropylthio, 3,3,3-trichloropropylthio, $SCH_2$—$C_2F_5$, $SCF_2$—$C_2F_5$, 1-($CH_2F$)-2-fluoroethylthio, 1-($CH_2Cl$)-2-chloroethylthio, 1-($CH_2Br$)-2-bromoethylthio, 4-fluorobutylthio, 4-chlorobutylthio, 4-bromobutylthio or nonafluorobutylthio. $C_1$-$C_6$-Haloalkylthio is additionally, for example, 5-fluoropentylthio, 5-chloropentylthio, 5-brompentylthio, 5-iodopentylthio, undecafluoropentylthio, 6-fluorohexylthio, 6-chlorohexylthio, 6-bromohexylthio, 6-iodohexylthio or dodecafluorohexylthio.

The term "$C_1$-$C_2$-alkylsulfinyl" is a $C_1$-$C_2$-alkyl group, as defined above, attached via a sulfinyl [S(O)] group. The term "$C_1$-$C_4$-alkylsulfinyl" is a $C_1$-$C_4$-alkyl group, as defined above, attached via a sulfinyl [S(O)] group. The term "$C_1$-$C_6$-alkylsulfinyl" is a $C_1$-$C_6$-alkyl group, as defined above, attached via a sulfinyl [S(O)] group. The term "$C_1$-$C_{10}$-alkylsulfinyl" is a $C_1$-$C_{10}$-alkyl group, as defined above, attached via a sulfinyl [S(O)] group. $C_1$-$C_2$-Alkylsulfinyl is methylsulfinyl or ethylsulfinyl. $C_1$-$C_4$-Alkylsulfinyl is additionally, for example, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl) or 1,1-dimethylethylsulfinyl (tert-butylsulfinyl). $C_1$-$C_6$-Alkylsulfinyl is additionally, for example, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl or 1-ethyl-2-methylpropylsulfinyl. $C_1$-$C_8$-Alkylsulfinyl is additionally, for example, heptylsulfinyl, octylsulfinyl, 2-ethylhexylsulfinyl and positional isomers thereof. $C_1$-$C_{10}$-Alkylsulfinyl is additionally, for example, nonylsulfinyl, decylsulfinyl and positional isomers thereof.

The term "$C_1$-$C_2$-haloalkylsulfinyl" is a $C_1$-$C_2$-haloalkyl group, as defined above, attached via a sulfinyl [S(O)] group. The term "$C_1$-$C_4$-haloalkylsulfinyl" is a $C_1$-$C_4$-haloalkyl group, as defined above, attached via a sulfinyl [S(O)] group. The term "$C_1$-$C_6$-haloalkylsulfinyl" is a $C_1$-$C_6$-haloalkyl group, as defined above, attached via a sulfinyl [S(O)] group. The term "$C_1$-$C_{10}$-haloalkylsulfinyl" is a $C_1$-$C_{10}$-haloalkyl group, as defined above, attached via a sulfinyl [S(O)] group. $C_1$-$C_2$-Haloalkylsulfinyl is, for example, $S(O)CH_2F$, $S(O)CHF_2$, $S(O)CF_3$, $S(O)CH_2Cl$, $S(O)CHCl_2$, $S(O)CCl_3$, chlorofluoromethylsulfinyl, dichlorofluoromethylsulfinyl, chlorodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl or $S(O)C_2F_5$. $C_1$-$C_4$-Haloalkylsulfinyl is additionally, for example, 2-fluoropropylsulfinyl, 3-fluoropropylsulfinyl, 2,2-difluoropropylsulfinyl, 2,3-difluoropropylsulfinyl, 2-chloropropylsulfinyl, 3-chloropropylsulfinyl, 2,3-dichloropropylsulfinyl, 2-bromopropylsulfinyl, 3-bromopropylsulfinyl, 3,3,3-trifluoropropylsulfinyl, 3,3,3-trichloropropylsulfinyl, $S(O)CH_2$—$C_2F_5$, $S(O)CF_2$—$C_2F_5$, 1-($CH_2F$)-2-fluoroethylsulfinyl, 1-($CH_2Cl$)-2-chloroethylsulfinyl, 1-($CH_2Br$)-2-bromoethylsulfinyl, 4-fluorobutylsulfinyl, 4-chlorobutylsulfinyl, 4-bromobutylsulfinyl or nonafluorobutylsulfinyl. $C_1$-$C_6$-Haloalkylsulfinyl is additionally, for example, 5-fluoropentylsulfinyl, 5-chloropentylsulfinyl, 5-brompentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl or dodecafluorohexylsulfinyl.

The term "$C_1$-$C_2$-alkylsulfonyl" is a $C_1$-$C_2$-alkyl group, as defined above, attached via a sulfonyl [S(O)$_2$] group. The term "$C_1$-$C_4$-alkylsulfonyl" is a $C_1$-$C_4$-alkyl group, as defined above, attached via a sulfonyl [S(O)$_2$] group. The term "$C_1$-$C_6$-alkylsulfonyl" is a $C_1$-$C_6$-alkyl group, as defined above, attached via a sulfonyl [S(O)$_2$] group. The term "$C_1$-$C_{10}$-alkylsulfonyl" is a $C_1$-$C_{10}$-alkyl group, as defined above, attached via a sulfonyl [S(O)$_2$] group. $C_1$-$C_2$-Alkylsulfonyl is methylsulfonyl or ethylsulfonyl. $C_1$-$C_4$-Alkylsulfonyl is additionally, for example, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl) or 1,1-dimethylethylsulfonyl (tert-butylsulfonyl). $C_1$-$C_6$-Alkylsulfonyl is additionally, for example, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl or 1-ethyl-2-methylpropylsulfonyl. $C_1$-$C_8$-Alkylsulfonyl is additionally, for example, heptylsulfonyl, octylsulfonyl, 2-ethylhexylsulfonyl and positional isomers thereof. $C_1$-$C_{10}$-Alkylsulfonyl is additionally, for example, nonylsulfonyl, decylsulfonyl and positional isomers thereof.

The term "$C_1$-$C_2$-haloalkylsulfonyl" is a $C_1$-$C_2$-haloalkyl group, as defined above, attached via a sulfonyl [S(O)$_2$] group. The term "$C_1$-$C_4$-haloalkylsulfonyl" is a $C_1$-$C_4$-haloalkyl group, as defined above, attached via a sulfonyl [S(O)$_2$] group. The term "$C_1$-$C_6$-haloalkylsulfonyl" is a $C_1$-$C_6$-haloalkyl group, as defined above, attached via a sulfonyl [S(O)$_2$] group. The term "$C_1$-$C_{10}$-haloalkylsulfonyl" is a $C_1$-$C_{10}$-haloalkyl group, as defined above, attached via a sulfonyl [S(O)$_2$] group. $C_1$-$C_2$-Haloalkylsulfonyl is, for example, S(O)$_2$CH$_2$F, S(O)$_2$CHF$_2$, S(O)$_2$CF$_3$, S(O)$_2$CH$_2$Cl, S(O)$_2$CHCl$_2$, S(O)$_2$CCO$_3$, chlorofluoromethylsulfonyl, dichlorofluoromethylsulfonyl, chlorodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl or S(O)$_2$C$_2$F$_5$. $C_1$-$C_4$-Haloalkylsulfonyl is additionally, for example, 2-fluoropropylsulfonyl, 3-fluoropropylsulfonyl, 2,2-difluoropropylsulfonyl, 2,3-difluoropropylsulfonyl, 2-chloropropylsulfonyl, 3-chloropropylsulfonyl, 2,3-dichloropropylsulfonyl, 2-bromopropylsulfonyl, 3-bromopropylsulfonyl, 3,3,3-trifluoropropylsulfonyl, 3,3,3-trichloropropylsulfonyl, S(O)$_2$CH$_2$—C$_2$F$_5$, S(O)$_2$CF$_2$—C$_2$F$_5$, 1-(CH$_2$F)-2-fluoroethylsulfonyl, 1-(CH$_2$Cl)-2-chloroethylsulfonyl, 1-(CH$_2$Br)-2-bromoethylsulfonyl, 4-fluorobutylsulfonyl, 4-chlorobutylsulfonyl, 4-bromobutylsulfonyl or nonafluorobutylsulfonyl. $C_1$-$C_6$-Haloalkylsulfonyl is additionally, for example, 5-fluoropentylsulfonyl, 5-chloropentylsulfonyl, 5-brompentylsulfonyl, 5-iodopentylsulfonyl, undecafluoropentylsulfonyl, 6-fluorohexylsulfonyl, 6-chlorohexylsulfonyl, 6-bromohexylsulfonyl, 6-iodohexylsulfonyl or dodecafluorohexylsulfonyl.

The term "3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members" as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl include:
Oxiranyl, aziridinyl, oxetidinyl (radical of trimethylene oxide), thietidinyl (radical of trimethylene sulfide), azetidinyl, 2-tetrahydrofuranyl, 3-tetrahydrofuranyl, 1,3-dioxolane-2-yl, 1,3-dioxolane-4-yl, 2-tetrahydrothienyl, 3-tetrahydrothienyl, 1,3-thiolane-2-yl, 1,3-dithiolane-4-yl, 1-thia-3-oxolan-2-yl, 1-thia-3-oxolan-4-yl, 1-thia-3-oxolan-5-yl, 2-thiolyl-1,1-dioxide, 3-thiolyl-1,1-dioxide, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 3-tetrahydropyranyl, 4-tetrahydropyranyl, 1,3-dioxan-2-yl, 1,3-dioxan-4-yl, 1,3-dioxan-5-yl, 1,4-dioxan-2-yl, 2-thianyl, 3-thianyl, 4-thianyl, 1,3-dithian-2-yl, 1,3-dithian-4-yl, 1,3-dithian-5-yl, 1,4-dithian-2-yl, 1-oxa-3-thian-2-yl, 1-oxa-3-thian-4-yl, 1-oxa-3-thian-5-yl, 1-oxa-3-thian-6-yl, 1-oxa-4-thian-2-yl, 1-oxa-4-thian-3-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

3-, 4-, 5-, 6- or 7-membered aromatic heterocyclyl is 5- or 6-membered aromatic heterocyclyl (hetaryl). Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

$C_2$-$C_7$-alkylene is divalent branched or preferably unbranched saturated aliphatic chain having 2 to 7 carbon atoms, for example CH$_2$CH$_2$, —CH(CH$_3$)—, CH$_2$CH$_2$CH$_2$, CH(CH$_3$)CH$_2$, CH$_2$CH(CH$_3$), CH$_2$CH$_2$CH$_2$CH$_2$, CH$_2$CH$_2$CH$_2$CH$_2$CH$_2$, CH$_2$CH$_2$CH$_2$CH$_2$CH$_2$CH$_2$, and CH$_2$CH$_2$CH$_2$CH$_2$CH$_2$CH$_2$CH$_2$ In the definition of the ligands in the catalyst (see below), the following definitions apply for the generic terms, if not yet mentioned above:

The expression "alkyl" refers to straight-chain and branched alkyl groups. These are preferably straight-chain or branched C$_1$-C$_{20}$-alkyl, more preferably C$_1$-C$_{12}$-alkyl, particularly preferably C$_1$-C$_8$-alkyl and very particularly preferably C$_1$-C$_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "substituted alkyl" encompasses substituted alkyl groups which bear one or more, for example 1, 2, 3, 4 or 5 substituents, preferably 1, 2 or 3 substituents and particularly preferably 1 substituent, selected for example from among cycloalkyl, aryl, hetaryl, halogen, NE$^1$E$^2$, NE$^1$E$^2$E$^{3+}$X$^-$, COOH, carboxylate, —SO$_3$H and sulfonate (if not specified otherwise). E$^1$, E$^2$ and E$^3$ are identical or different radicals selected from hydrogen, C$_1$-C$_6$-alkyl, C$_3$-C$_{10}$-cycloalkyl and aryl; and X$^-$ is an anion equivalent.

In the definition of the ligands, the expression "alkylene" refers to straight-chain or branched alkanediyl groups having for example from 1 to 8, preferably from 1 to 4 carbon atoms.

The expression "cycloalkyl" encompasses C$_3$-C$_{12}$-cycloalkyl groups, such as cyclopropyl, cyclobutyl, cyclopentyl, cyclohexyl, cycloheptyl, cyclooctyl, cyclononyl, cyclopdecyl, cycloundecyl and cyclododecyl, preferably C$_5$-C$_7$-cycloalkyl groups such as cyclopentyl, cyclohexyl or cycloheptyl. Substituted cycloalkyl bears one or more, for example 1, 2, 3, 4 or 5 substituents, preferably 1, 2 or 3 substituents and particularly preferably 1 substituent, selected from among alkyl, alkoxy and halogen (if not specified otherwise).

The expression "heterocycloalkyl" or "heterocyclyl" refers to saturated, cycloaliphatic groups which generally have from 4 to 7, preferably 5 or 6, ring atoms and in which 1, 2, 3 or 4 of the ring carbons are replaced by heteroatoms selected from among the elements oxygen, nitrogen (nitrogen may be present, for example, as NR or NO, where R is H or a group different therefrom, e.g. alkyl, alkoxy, CN, a group bound via CO etc.) and sulfur (sulfur may be present, for example, as S, SO or SO$_2$). Substituted heterocyclyl bears one or more substituents, for example 1, 2 or 3 substituents, preferably 1 or 2 substituents, particularly preferably 1 substituent, for example selected from among alkyl, aryl, COOR$^f$, COO$^-$M$^+$ and NE$^1$E$^2$, preferably alkyl (if not specified otherwise). Examples of heterocycloaliphatic groups are tetrahydrofuranyl, tetrahydrothienyl, pyrrolidinyl, pyrazolidinyl, imidazolidinyl, oxazolidinyl, thiazolidinyl, isoxazolidinyl, isothiazolidinyl, piperidinyl, morpholinyl, thiomorpholinyl, piperazinyl, tetrahydropyranyl, dioxanyl.

The expression "aryl" encompasses carbocyclic aromatic ring systems and preferably refers to phenyl, naphthyl, fluorenyl, anthracenyl, phenanthrenyl or naphthacenyl, particularly preferably phenyl or naphthyl. Substituted aryl bears one or more substituents, for example 1, 2, 3, 4 or 5 substituents, preferably 1, 2 or 3 substituents and particularly preferably 1 substituent, selected from among alkyl, alkoxy, carboxyl, carboxylate, trifluoromethyl, —SO$_3$H, sulfonate, NE$^1$E$^2$, alkylene-NE$^1$E$^2$, nitro, cyano and halogen (if not specified otherwise). Specific examples of substituted aryl are tolyl, xylyl and mesityl.

The expression "hetaryl" encompasses, for the purposes of the present invention, 5- to 14-membered, preferably 5- to 10-membered mono- or polycyclic heterocycloaromatic groups comprising 1, 2, 3 or 4 heteroatoms selected from O, S and N as ring members. Examples are furanyl, thienyl, pyrrolyl, pyrazolyl, imidazolyl, oxazolyl, thiazolyl, isoxazolyl, isothiazolyl, triazolyl, oxadiazolyl, thiadiazolyl, pyridyl, pyrimidyl, pyrazinyl, pyridazinyl, triazinyl, indolyl, isoindolyl, benzofuranyl, benzothienyl, benzopyrazolyl, benzoimidazolyl, benzoxazolyl, benzothiazolyl, benzoisoxazolyl, benzoisothiazolyl, quinolinyl, isoquinolinyl, quinacridinyl, benzindolyl, acridinyl, xanthenyl, phenanthrolinyl and the like. Substituted hetaryl bears one or more, for example 1, 2 or 3 substituents selected for example from among alkyl, alkoxy, carboxyl, carboxylate, —SO$_3$H, sulfonate, NE$^1$E$^2$, alkylene-NE$^1$E$^2$, trifluoromethyl and halogen (if not specified otherwise).

The term "polycyclyl" relates to condenced carbocyclic saturated ring systems, the term "condensed" also comprising spiro-annelated systems. Examples are norbornane, [2,2,2]-bicyclooctane, tetraline, adamantyl and the like.

Carboxylate and sulfonate are preferably derivatives of a carboxylic acid function and a sulfonic acid function, respectively, in particular a metal carboxylate or sulfonate, a carboxylic ester or sulfonic ester function or a carbonamide or sulfonamide function. These include, for example, the esters of C$_1$-C$_4$-alkanols such as methanol, ethanol, n-propanol, isopropanol, n-butanol, sec-butanol and tert-butanol. They also include the primary amides and their N-alkyl and N,N-dialkyl derivatives.

What has been said above with regard to the expressions "alkyl", "cycloalkyl", "aryl", "heterocycloalkyl" and "hetaryl" applies correspondingly to the expressions "alkoxy", "cycloalkoxy", "aryloxy", "heterocycloalkoxy" and "hetaryloxy".

The expression "acyl" refers to alkanoyl or aroyl groups generally having from 2 to 11, preferably from 2 to 8, carbon atoms, for example the acetyl, propanoyl, butanoyl, pentanoyl, hexanoyl, heptanoyl, 2-ethylhexanoyl, 2-propylheptanoyl, benzoyl or naphthoyl group.

The groups NE$^1$E$^2$ and NE$^{22}$E$^{23}$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

M$^+$ is a cation equivalent, i.e. a monovalent cation or the proportion of a polyvalent cation corresponding to a simple positive charge. The cation M$^+$ serves only as counterion to neutralize negatively charged substituent groups such as COO$^-$ or sulfonate groups and can in principle be chosen freely. Preference is therefore given to using alkali metal ions, in particular Na$^+$, K$^+$, Li$^+$ ions, or onium ions such as ammonium, monoalkylammonium, dialkylammonium, trialkylammonium, tetraalkylammonium, phosphonium, tetraalkylphosphonium or tetraarylphosphonium ions.

Analogously, the anion equivalent X$^-$ serves only as counterion to balance positively charged substituent groups, e.g. ammonium groups, and can be selected freely from among monovalent anions and the proportions of polyvalent anions corresponding to a single negative charge. Examples of suitable anions are halide ions X$^-$, e.g. chloride and bromide.

Preferred anions are sulfate and sulfonate, e.g. $SO_4^{2-}$, tosylate, trifluoromethanesulfonate and methylsulfonate.

Fused ring systems can be aromatic, hydroaromatic and cyclic compounds linked by fusion. Fused ring systems consist of two, three or more rings. Depending on the way in which the rings of fused ring systems are linked, a distinction is made between orthofusion, i.e. each ring shares an edge or two atoms with each adjacent ring, and perifusion in which one carbon atom belongs to more than two rings. Among fused ring systems, preference is given to ortho-fused ring systems.

The remarks made below concerning preferred embodiments of the processes of the invention, the catalyst used therein, the reaction conditions and also of compounds of formulae I, II and III, especially with respect to their substituents Z, X, Y, $A^1, A^2, A^3, A^4, B^1, B^2, B^3, R^1, R^2, R^3, R^4, R^5, R^6, R^7, R^8, R^9, R^{10}, R^{11}, R^{12}, R^{13}, R^{14}, R^{15}, R^{16}, R^{17}, R^{18}$, m, n, p and q, are valid both on their own and, in particular, in every possible combination with each other. The remarks made below apply to both processes A and B.

As a matter of course, the q radicals $R^5$ replace a hydrogen atom on a carbon ring atom. For instance, if $B^1$, $B^2$ or $B^3$ is defined to be CH and if this position is to be substituted by a radical $R^5$, then $B^1$, $B^2$ or $B^3$ is of course C—$R^5$. If there is more than one radical $R^5$, these can be the same or different.

As a matter of course, the p radicals $R^4$ replace a hydrogen atom on a carbon ring atom. For instance, if $A^1, A^2, A^3$ or $A^4$ is defined to be CH and if this position is to be substituted by a radical $R^4$, then $A^1, A^2, A^3$ or $A^4$ is of course C—$R^4$. If there is more than one radical $R^4$, these can be the same or different.

Compounds I, II and III are principally known from WO 2010/072781.

In compounds II, Z is preferably selected from Br, I and —$OSO_2$—$R^{z1}$, where $R^{z1}$ is as defined above. Preferably, $R^{z1}$ is selected from $CH_3$, $CF_3$ and 4-methylphenyl (p-tolyl).

Thus, Z is more preferably selected from Br, I and —$OSO_2$—$R^{z1}$, where $R^{z1}$ is selected from $CH_3$, $CF_3$ and 4-methylphenyl (p-tolyl). In particular, Z is Br.

In the processes of the invention, carbon monoxide and hydrogen are used in a molar ratio of preferably from 100:1 to 1:10, more preferably from 10:1 to 1:10, even more preferably from 5:1 to 1:5, in particular from 2:1 to 1:2 and specifically of about 1:1. Very specifically, synthesis gas is used.

Carbon monoxide and hydrogen may be introduced into the reaction separately or as a mixture. Preferably they are introduced as a mixture, especially in the form of synthesis gas.

The catalyst used in the processes of the invention is preferably a complex compound of a transition metal of group VIII of the periodic system of elements. Among these metals, preference is given to Pd, Pt, Ni, $R^h$, Ir and Ru; Pd being particularly preferred.

The complex compound contains, apart the central transition metal, one or more ligands. Preferred ligands are mono- or bidentate ligands.

More preferred complexes comprise at least one phosphorus-containing compound as ligand. The phosphorus-containing compounds are preferably selected from among $PF_3$, phosphols, phosphabenzenes, monodentate, bidentate and polydentate phosphine, phosphinite, phosphonite, phosphoramidite and phosphite ligands and mixtures thereof.

More preferred are P(III)-containing compounds. Even more preferred ligands are mono- or bidentate phosphorus-containing ligands; preferably mono- or bidentate P(III)-containing ligands. In one embodiment, particularly preferred are bidentate P-containing ligands, especially bidentate P(III)-containing ligands. In an alternative embodiment, particularly preferred are monodentate P-containing ligands, especially monodentate P(III)-containing ligands.

Suitable phosphorus-containing ligands are described, for example, in Beller, J. Molecular Catalysis, A, 104, 1995, 17-85.

Monodentate phosphorus-containing ligands are preferably selected from phosphorus compounds of formula $PR^aR^bR^c$ where $R^a$, $R^b$ and $R^c$, independently of each other, are selected from $C_3$-$C_{12}$-alkyl, $C_3$-$C_{12}$-alkoxy, where the alkyl moieties in the 2 last-mentioned radicals may carry 1, 2 or 3 substituents $R^d$; $C_3$-$C_{10}$-cycloalkyl, $C_3$-$C_{10}$-cycloalkoxy, heterocyclyl, heterocyclyloxy, $C_4$-$C_{18}$-polycyclyl, $C_5$-$C_{18}$-polycyclyloxy, aryl, aryloxy, hetaryl and hetaryloxy, where the cycloalkyl, heterocyclyl, polycyclyl, aryl and hetaryl moieties in the 10 last-mentioned radicals may carry 1, 2, 3 or 4 substituents $R^e$;

or $R^a$ and $R^b$ together with the phosphorus atom to which they are bound form a 5-, 6-, 7- or 8-membered heterocyclic ring which may be additionally fused to one, two or three $C_3$-$C_{10}$-cycloalkyl, $C_3$-$C_{10}$-heterocyclyl, aryl or hetaryl groups, where the heterocyclic ring and, if present, the fused-on groups may each independently carry one, two, three or four substituents $R^e$;

each $R^d$ is independently selected from $C_3$-$C_{10}$-cycloalkyl, $C_3$-$C_{10}$-cycloalkoxy, heterocyclyl, heterocyclyloxy, aryl, aryloxy, hetaryl, hetaryloxy, $C_1$-$C_6$-alkoxy, OH, SH, COOH, carboxylate, $SO_3H$, sulfonate, $NE^1E^2$, $NE^1E^2E^{3+}X^-$, halogen, nitro, acyl and cyano;

each $R^e$ is independently selected from $C_1$-$C_6$-alkyl, $C_3$-$C_{10}$-cycloalkyl, $C_3$-$C_{10}$-cycloalkoxy, heterocyclyl, heterocyclyloxy, aryl, aryloxy, hetaryl, hetaryloxy, $C_1$-$C_6$-alkoxy, OH, SH, COOH, carboxylate, $SO_3H$, sulfonate, $NE^1E^2$, $NE^1E^2E^{3+}X^-$, halogen, nitro, acyl and cyano;

$E^1$, $E^2$ and $E^3$ are identical or different radicals selected from hydrogen, $C_1$-$C_6$-alkyl, $C_3$-$C_{10}$-cycloalkyl and aryl; and $X^-$ is an anion equivalent.

In preferred monodentate phosphorus-containing ligands of formula $PR^aR^bR^c$, at least one of $R^a$, $R^b$ and $R^c$ comprises a cyclic group, i.e. is selected from $C_3$-$C_{10}$-cycloalkyl, $C_3$-$C_{10}$-cycloalkoxy, heterocyclyl, heterocyclyloxy, $C_5$-$C_{18}$-polycyclyl, $C_5$-$C_8$-polycyclyloxy, aryl, aryloxy, hetaryl and hetaryloxy which may be substituted as defined above. Preferred radicals $R^e$ are selected from $C_1$-$C_6$-alkyl and $C_1$-$C_4$-alkoxy.

$R^a$, $R^b$ and $R^c$, independently of each other, are preferably selected from $C_3$-$C_{12}$-alkyl, cyclohexyl, adamantyl, phenyl and phenoxy, where the cyclohexyl, adamantyl and phenyl moiety in the 4 last-mentioned radicals may carry 1, 2 or 3 substituents selected from $C_1$-$C_6$-alkyl and $C_1$-$C_4$-alkoxy. More preferably, at least one of $R^a$, $R^b$ and $R^c$ is selected from cyclohexyl, adamantyl, phenyl and phenoxy, which may carry 1, 2 or 3 substituents selected from $C_1$-$C_6$-alkyl and $C_1$-$C_4$-alkoxy.

Even more preferably, at least one of $R^a$, $R^b$ and $R^c$ is selected from cyclohexyl, adamantyl, phenyl and phenoxy, which may be substituted by 1, 2 or 3 radicals $R^e$ selected from $C_1$-$C_6$-alkyl and $C_1$-$C_4$-alkoxy, and the remaining radicals $R^a$, $R^b$ and $R^c$ are selected from $C_3$-$C_{12}$-alkyl, cyclohexyl, adamantyl, phenyl and phenoxy, where the cyclohexyl, adamantyl and phenyl moiety in the 4 last-mentioned radicals may be substituted by 1, 2 or 3 radicals $R^e$ selected from $C_1$-$C_6$-alkyl and $C_1$-$C_4$-alkoxy.

Specific monodentate phosphorus-containing ligands are selected from tricyclohexyl phosphine ($R^a$, $R^b$ and $R^c$ are cyclohexyl), butyl-di-(1-adamantanyl)-phosphine ($R^a$ and $R^b$ are 1-adamantanyl, and $R^c$ is n-butyl), triphenylphosphine ($R^a$, $R^b$ and $R^c$ are phenyl), triphenylphosphite ($R^a$, $R^b$ and $R^c$ are phenoxy), tri-(2-tert-butyl-4-methoxyphenyl)-phosphite ($R^a$, $R^b$ and $R^c$ are 2-tert-butyl-4-methoxy-phenoxy) and 2,6-bis(2,5-dimethylphenyl)-1-octyl-4-phenylphophacyclohexan.

Bidentate phosphorus-containing ligands are preferably selected from phosphorus compounds of formula

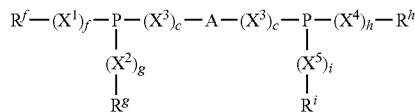

where
$X^1$, $X^2$, $X^3$, $X^4$ and $X^5$, independently of each other and independently of each occurrence, are selected from O, S, $NR^j$ and a group $SiR^kR^l$, where $R^j$, $R^k$ and $R^l$, independently of each other, are selected from hydrogen, $C_1$-$C_4$-alkyl, $C_3$-$C_6$-cycloalkyl, heterocyclyl, aryl and hetaryl;
c, f, g, h and i are independently 0 or 1;
$R^f$, $R^g$, $R^h$ and $R^i$, independently of each other, are selected from $C_3$-$C_{12}$-alkyl which may carry 1, 2 or 3 substituents $R^d$; $C_3$-$C_{10}$-cycloalkyl, heterocyclyl, $C_5$-$C_8$-polycyclyl, aryl and hetaryl, where the cycloalkyl, heterocyclyl, polycyclyl, aryl and hetaryl moieties in the 5 last-mentioned radicals may carry 1, 2, 3 or 4 substituents $R^e$;
where $R^d$ and $R^e$ are as defined above (as for the monodentate P-compounds); or
in case $X^1$ and $X^2$ are O or $NR^j$ and f and g are 1, $R^f$ together with $R^g$ may form a $C_2$-$C_5$-alkylene group; and/or in case $X^4$ and $X^5$ are O or $NR^j$ and h and g are 1, $R^h$ together with $R^i$ may form a $C_2$-$C_5$-alkylene group; and
A is a bridging group.

The bridging groups A are preferably selected from divalent aliphatic groups, divalent alicyclic groups, divalent heterocyclic groups, divalent aliphatic-alicyclic groups, divalent aromatic groups, divalent araliphatic groups, divalent heteroaromatic groups, divalent heteroaromatic-aliphatic groups and divalent metallocene groups.

Divalent aliphatic radicals are those which contain no cycloaliphatic, aromatic or heterocyclic constituents. Examples are alkylene, alkenylene, and alkynylene radicals.

Divalent alicyclic radicals may contain one or more, e.g., one or two, alicyclic radicals; however, they contain no (hetero)aromatic or heterocyclic constituents. The alicyclic radicals may be substituted by aliphatic radicals, but bonding sites for the $(X^3)_c$-groups are located on the alicyclic radical.

Divalent aliphatic-alicyclic radicals contain not only at least one divalent aliphatic radical but also at least one divalent alicyclic radical, the two bonding sites for the $(X^3)_c$-groups possibly being located either both on the alicyclic radical(s) or both on the aliphatic radical(s) or one on an aliphatic radical and the other on an alicyclic radical.

Divalent aromatic radicals may contain one or more, e.g., one or two, aromatic radicals; however, they contain no alicyclic or heterocyclic or heteroaromatic constituents. The aromatic radicals may be substituted by aliphatic and other radicals, but both bonding sites for the $(X^3)_c$-groups are located on the aromatic radical(s).

Divalent araliphatic radicals contain not only at least one divalent aliphatic radical but also at least one divalent aromatic radical, the two bonding sites for the $(X^3)_c$-groups possibly being located either both on the aromatic radical(s) or both on the aliphatic radical(s) or one on an aliphatic radical and the other on an aromatic radical.

Divalent heteroaromatic radicals may contain one or more, e.g., one or two, heteroaromatic radicals; however, they contain no alicyclic or heterocyclic constituents. The heteroaromatic radicals may be substituted by aliphatic and other radicals, but both bonding sites for the $(X^3)_c$-groups are located on the heteroaromatic radical(s).

Divalent heteroaromatic-aliphatic radicals contain not only at least one divalent aliphatic radical but also at least one divalent heteroaromatic radical, the two bonding sites for the $(X^3)_c$-groups possibly being located either both on the heteroaromatic radical(s) or both on the aliphatic radical(s) or one on an aliphatic radical and the other on an heteroaromatic radical.

In divalent metallocene groups, the two bonding sites for the $(X^3)_c$-groups are located on one of the two aromatic rings or, preferably, on the two aromatic rings.

Preferred divalent aliphatic radicals A are linear or branched $C_2$-$C_{20}$-alkylene, more preferably linear or branched $C_2$-$C_{10}$-alkylene, even more preferably linear or branched $C_2$-$C_8$-alkylene and in particular linear or branched $C_2$-$C_6$-alkylene.

Examples of suitable $C_2$-$C_{20}$-alkylene radicals are 1,2-ethylenediyl, 1,2- and 1,3-propanediyl, 2,2-dimethyl-1,3-propanediyl, 1,4-butanediyl, 1,5-pentanediyl, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene, nonadecamethylene, eicosamethylene, 2-butyl-2-ethyl-1,5-pentamethylene, 2,2,4- or 2,4,4-trimethyl-1,6-hexamethylene, 2-methylpentane-1,5-diyl, and 4-methylpentane-1,4-diyl, and the like.

Examples of suitable $C_2$-$C_{10}$-alkylene radicals are 1,2-ethylenediyl, 1,2- and 1,3-propanediyl, 2,2-dimethyl-1,3-propanediyl, 1,4-butanediyl, 1,5-pentanediyl, hexamethylene, heptamethylene, octamethylene, nonamethylene, decamethylene, 2,2,4- or 2,4,4-trimethyl-1,6-hexamethylene, 2-methylpentane-1,5-diyl, and 4-methylpentane-1,4-diyl, and the like.

Examples of suitable $C_2$-$C_8$-alkylene radicals are 1,2-ethylenediyl, 1,2- and 1,3-propanediyl, 2,2-dimethyl-1,3-propanediyl, 1,4-butanediyl, 1,5-pentanediyl, hexamethylene, heptamethylene, octamethylene, 2-methylpentane-1,5-diyl, and 4-methylpentane-1,4-diyl, and the like.

Examples of suitable $C_2$-$C_6$-alkylene radicals are 1,2-ethylenediyl, 1,2- and 1,3-propanediyl, 2,2-dimethyl-1,3-propanediyl, 1,4-butanediyl, 1,5-pentanediyl, hexamethylene, 2-methylpentane-1,5-diyl, and 4-methylpentane-1,4-diyl, and the like.

Preferred divalent alicyclic radicals A are selected from optionally substituted $C_5$-$C_8$-cycloalkylene, optionally substituted $C_5$-$C_8$-cycloalkenylene, optionally substituted $C_5$-$C_8$-bicycloalkylene and optionally substituted $C_5$-$C_8$-bicycloalkenylene.

Examples of suitable $C_5$-$C_8$-cycloalkylene and $C_5$-$C_8$-cycloalkenylene diradicals are cyclopentanediyl, such as 1,2- or 1,3-cyclopentanediyl, cyclopentenediyl, such as cyclopent-1-ene-1,2-diyl, cyclopent-1-ene-1,3-diyl, cyclopent-1-ene-1,4-diyl, cyclopent-1-ene-1,5-diyl, cyclopent-1-ene-3,4-diyl or cyclopent-1-ene-3,5-diyl, cyclohexanediyl, such as cyclohexane-1,2-diyl, cyclohexane-1,3-diyl, or cyclohexane-1,4- diyl, cyclohexenediyl, such as cyclohex-1-ene-1,2-diyl, cyclohex-1-ene-1,3-diyl, cyclohex-1-ene-1,4-diyl, cyclohex-1-ene-1,5-diyl, cyclohex-1-ene-1,6-diyl, cyclohex-1-ene-3,4-diyl, cyclohex-1-ene-3,5-diyl, cyclohex-1-ene-3,6-diyl or cyclohex-1-ene-4,5-diyl, cycloheptanediyl, such as cycloheptane-1,2-diyl, cycloheptane-1,3-diyl, cycloheptane-1,4-diyl, cycloheptane-1,5-diyl, cycloheptane-1,6-diyl or cycloheptane-1,7-diyl, and cyclooctanediyl, such as cyclooctane-1,2-diyl, cyclooctane-1,3-diyl, cyclooctane-1,4-diyl, cyclooctane-1,5-diyl, cyclooctane-1,6-diyl, cyclooctane-1,7-diyl or cyclooctane-1,8-diyl.

Examples of suitable $C_5$-$C_8$-bicycloalkylene and $C_5$-$C_8$-bicycloalkenylene diradicals are norbornanediyl and norbornenediyl and heteroderivatives thereof.

Preferred divalent aliphatic-alicyclic radicals A are selected from $C_5$-$C_8$-cycloalkylene-$C_1$-$C_4$-alkylene, $C_5$-$C_8$-cycloalkylene-$C_1$-$C_4$-alkylene-$C_5$-$C_8$-cycloalkylene, and $C_1$-$C_4$-alkylene-$C_5$-$C_8$-cycloalkylene-$C_1$-$C_4$-alkylene, it being possible for the cycloalkylene radicals to be substituted.

Preferred divalent aromatic radicals A are selected from optionally substituted phenylene, optionally substituted biphenylene, optionally substituted naphthylene, optionally substituted binaphthylene, optionally substituted anthracene, optionally substituted dihydroanthracene and optionally substituted bridged dihydroanthracene, were the phenylene rings in biphenylene and the nathylene rings in binaphthylene may be bound via a bridging group.

Preferred divalent araliphatic radicals A are selected from optionally substituted phenylene-$C_1$-$C_4$-alkylene, optionally substituted phenylene-$C_1$-$C_4$-alkylene-phenylene and optionally substituted $C_1$-$C_4$-alkylene-phenylene-$C_1$-$C_4$-alkylene.

Preferred heteroaromatic radicals are optionally substituted xanthenediyl, optionally substituted acridin-diyl, optionally substituted tetrahydroacridindiyl, optionally substituted thioxanthenediyl and the like.

Preferred divalent groups are elected from $C_2$-$C_6$-alkylene, such as 1,2-ethylene, 1,3-propylene, 1,4-butylene, 1,5-pentylene or 1,6-hexylene, ferrocene-1,1'-diyl and divalent groups selected from the formulae A.1 to A.22

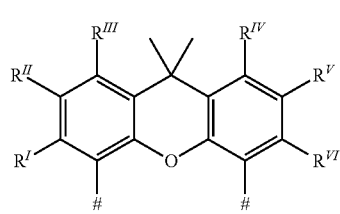

A.1

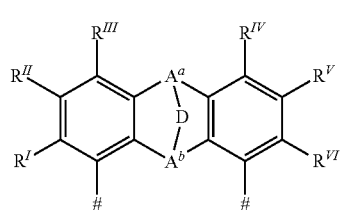

A.2

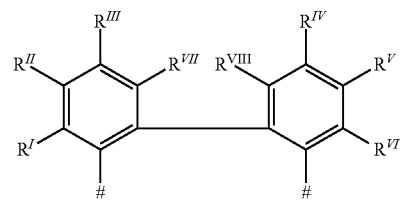

A.3

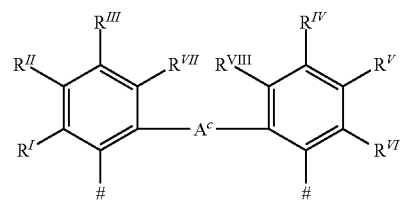

A.4

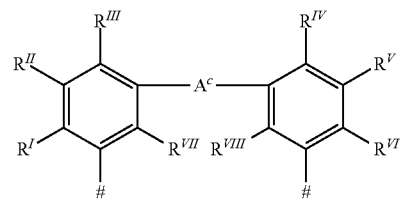

A.5

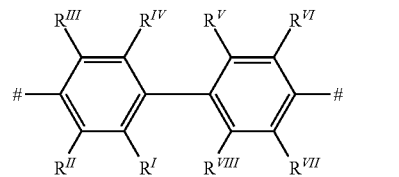

A.6

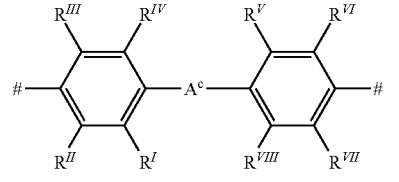

A.7

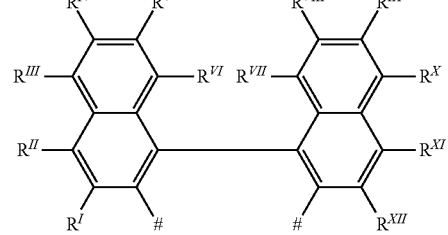

A.8

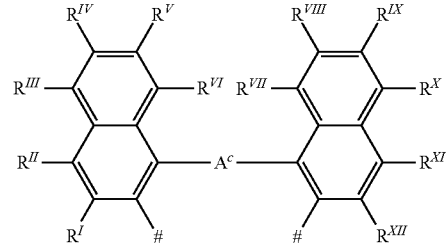

A.9

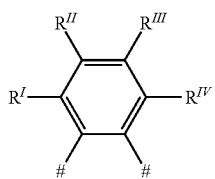
A.10

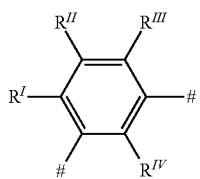
A.11

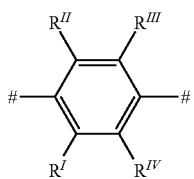
A.12

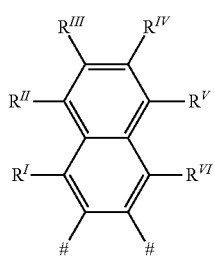
A.13

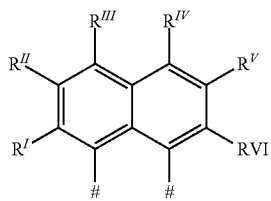
A.14

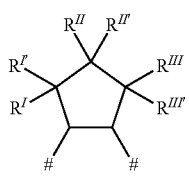
A.15

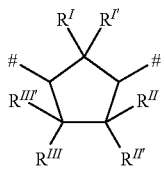
A.16

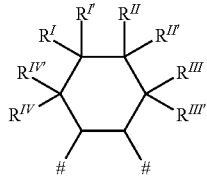
A.17

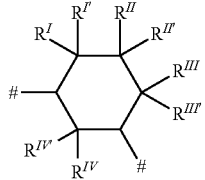
A.18

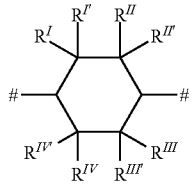
A.19

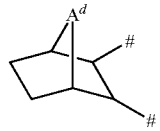
A.20

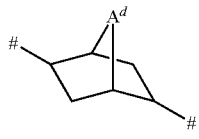
A.21

A.22 where
$R^I$, $R^{I'}$, $R^{II}$, $R^{II'}$, $R^{III}$, $R^{III'}$, $R^{IV}$, $R^{IV'}$, $R^V$, $R^{VI}$, $R^{VII}$, $R^{VIII}$, $R^{IX}$, $R^X$, $R^{XI}$ and $R^{XII}$ are independently of each another and independently of each occurrence, selected from hydrogen, alkyl, cycloalkyl, heterocycloalkyl, aryl, hetaryl, hydroxy, thiol, polyalkylene oxide, polyalkylenimine, alkoxy, halogen, $SO_3H$, sulfonate, $NE^{22}E^{23}$, alkylene-$NE^{22}E^{23}$, trifluoromethyl, nitro, alkoxycarbonyl, carboxyl, acyl or cyano, where $E^{22}$ and $E^{23}$ are identical or different radicals selected from among hydrogen, alkyl, cycloalkyl and aryl, $A^c$ and $A^d$ are O, S, $NR^\alpha$ or $SiR^\alpha R^\beta$, where
  $R^\alpha$ and $R^\beta$ are independently of each another selected from hydrogen, alkyl, cycloalkyl, heterocycloalkyl, aryl or hetaryl,
or $A^c$ and $A^d$ are a $C_1$-$C_4$-alkylene bridge which may have a double bond and/or an alkyl, cycloalkyl, heterocycloalkyl, aryl or hetaryl substituent,
or $A^c$ and $A^d$ are a $C_2$-$C_4$-alkylene bridge which is interrupted by O, S or $NR^\alpha$ or $SiR^\alpha R^\beta$,
where two adjacent radicals $R^I$ to $R^{VI}$ in the groups of the formula A.2 together with the carbon atom of the benzene ring to which they are bound may also form a fused ring system having 1, 2 or 3 further rings,
and two geminal radicals $R^I$, $R^{I'}$; $R^{II}$, $R^{II'}$; $R^{III}$, $R^{III'}$ and/or $R^{IV}$, $R^{IV'}$ in the groups of the formulae A.15 to A.19 may also form oxo or a ketal thereof,
$A^a$ and $A^b$ are, independently of one another, O, S, $SiR^\alpha R^\beta$, $NR^\gamma$ or $CR^\delta R^\epsilon$, where
  $R^\alpha$, $R^\beta$ and $R^\gamma$ are each, independently of one another, hydrogen, alkyl, cycloalkyl, heterocycloalkyl, aryl or hetaryl, R$^\delta$ and R$^\epsilon$ are, independently of one another, hydrogen, alkyl, cycloalkyl, heterocycloalkyl, aryl or hetaryl or the group R$^\delta$ together with a further group R$^\delta$ or the group R$^\epsilon$ together with a further group R$^\epsilon$ forms an intramolecular bridging group D, and D is either not present or is CH$_2$ or is CH$_2$CH$_2$.

Among these, preference is given to bridging groups A selected from C$_2$-C$_6$-alkylene, especially 1,2-ethylene, 1,3-propylene, 1,4-butylene, 1,5-pentylene and 1,6-hexylene; divalent binaphthyl groups (groups A.8 and A.9, A.8 being preferred), divalent xanthene groups (group A.1) and divalent ferrocenyl groups (where the P atoms are each bound to different cyclopentadienyl rings), where the 3 last-mentioned radicals may carry on their cyclic moieties 1, 2, 3, 4, 5 or 6 radicals selected from C$_1$-C$_6$-alkyl and C$_1$-C$_4$-alkoxy. The xanthenediyl group is preferred.

R$^f$, R$^g$, R$^h$ and R$^i$, independently of each other, are preferably selected from C$_3$-C$_{12}$-alkyl, cyclohexyl, adamantyl, phenyl, phenoxy and indolyl, where the phenyl moiety in phenyl and phenoxy and the indolyl radical may carry 1, 2 or 3 substituents selected from C$_1$-C$_6$-alkyl and C$_1$-C$_4$-alkoxy.

The catalysts used according to the present invention can additionally bear at least one further ligand which is preferably selected from among halides, amines, carboxylates, acetylacetonate, arylsulfonates or alkylsulfonates, hydride, CO, olefins, dienes, cycloolefines, nitriles, N-containing heterocycles, aromatics and heteroaromatics, ethers and mixtures thereof.

Specific ligands and catalyst compounds are the following:

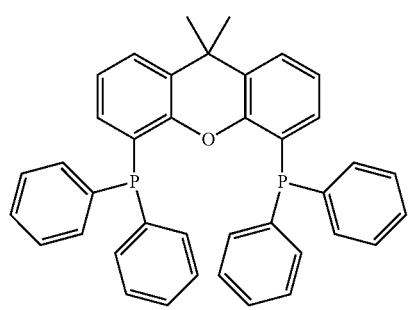

9,9-Dimethyl-4,5-bis(diphenyl-phosphino)xanthene (Xanthphos; ligand)

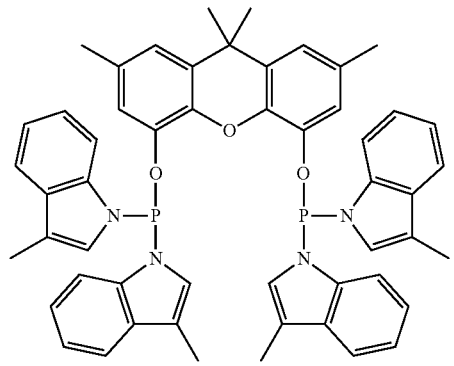

4,5-Bis-(di-1-(3-methylindolyl)-phosphoramidit)-2,7,9,9-tetramethyl-xanthene (MeSkatOX; ligand)

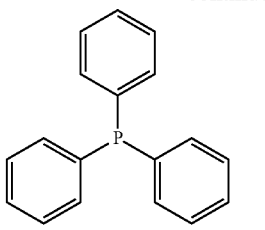

Triphenylphosphine (TPP; ligand)

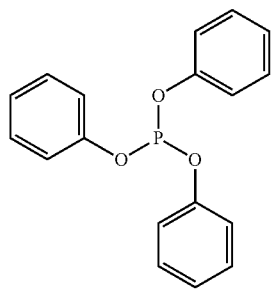

Triphenylphosphite (TPPit; ligand)

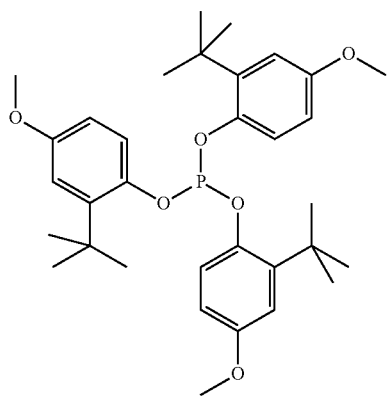

Tri-(2-(1,1-dimethylethyl)-4-methoxy-phenyl)-phosphite (tBuOMe TPPit; ligand)

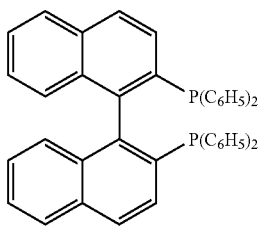

racemic-2,2'-Bis(diphenylphosphino)-1,1'-binaphthyl (BINAP; ligand)

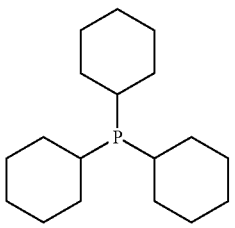

Tricyclohexylphosphine (CyH$_3$P; ligand)

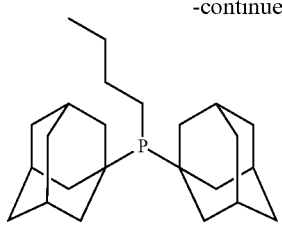

Butyldi-1-adamantylphosphine (cata-CXium; ligand)

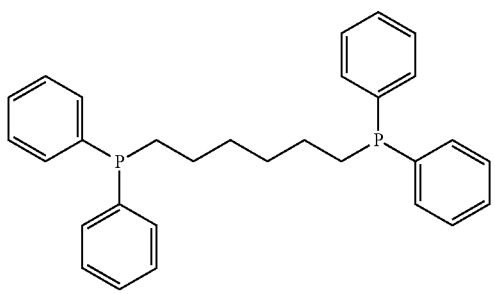

1,6-Bis(diphenylphosphino)hexane (DPPH; ligand)

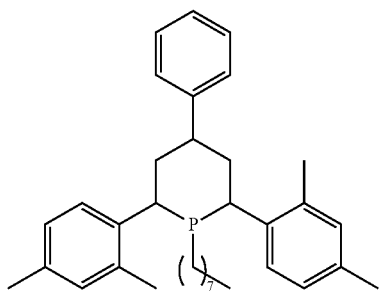

2,6-Bis(2,5-dimethylphenyl)-1-octyl-4-phenylphosphacyclohexan (PCH; ligand)

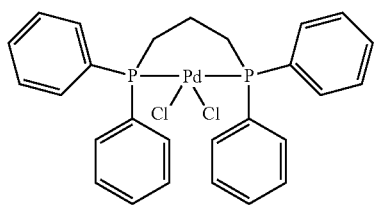

Dichloro[1,3-bis(diphenylphosphino)propane]palladium(II) (Complex 130; catalyst)

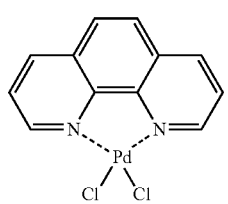

Dichloro(1,10-phenanthroline)-palladium(II) (Complex 34; catalyst)

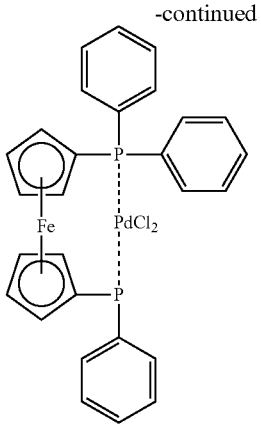

Dichloro[1,1′-bis(diphenylphosphino)-ferrocene]palladium(II), also complex with dichloromethane (Complex 128; catalyst)

Among these, specific preference is given to Xanthphos as ligand.

Among these, specific preference is alternatively given to butyl-di-1-adamantyl-phosphine (cataCXium) as ligand.

Without wishing to be bound by theory, it is assumed that in general, the catalysts or catalyst precursors form catalytically active species of the formula $H_xM_y(CO)_zL_q$, where M is a transition metal (preferably a metal of transition group VIII), L is a ligand (preferably a phosphorus-containing compound) and q, x, y, z are integers which depend on the valence and type of the metal and on the number of coordination sites occupied by the ligand L, under the hydroformylation conditions. z and q are preferably, independently of one another, at least 1, e.g. 1, 2 or 3. The sum of z and q is preferably from 1 to 5. The complexes can, if desired, additionally contain at least one of the above-described further ligands.

In a preferred embodiment, the catalysts are prepared in situ in the reactor used for the carbonylation reaction. However, if desired, the catalysts used according to the present invention can also be prepared separately and isolated by customary methods. To prepare the catalysts used according to the present invention in situ, it is possible, for example, to react at least one ligand, a compound or a complex of a transition metal, if desired at least one further additional ligand and, if appropriate, an activating agent in an inert solvent under the carbonylation conditions.

The catalyst is preferably produced by bringing the transition metal or a salt thereof and the ligand into contact with each other, preferably in situ. The metal is generally used as its salt, such as the chloride, bromide, sulphate, nitrate or acetate, optionally in combination with a simple (mostly solvent) ligand, such as cyclooctadiene (COD), or in form of another suitable compound, for example its oxide. For instance, Pd may be introduced as $PdCl_2$ or Pd(II) acetate or as $PdCl_2$-COD complex, etc. For instance, Pt may be used as its Pt(II) chloride, etc. For instance, rhodium may be introduced as its $R^h(II)$ or $R^h(III)$ salts, such as rhodium(III) chloride, rhodium(III) nitrate, rhodium(III) sulfate, potassium rhodium sulfate, rhodium(II) or rhodium(III) carboxylates, rhodium(II) and rhodium(III) acetate, rhodium(III) oxide, salts of rhodic(III) acid, trisammonium hexachlororhodate (III), etc. or as dicarbonylrhodium acetylacetonate, acetylacetonatobisethylenerhodium(I), etc. Ruthenium may be introduced as ruthenium(III) chloride, ruthenium(IV), ruthenium (VI) or ruthenium(VIII) oxide, alkali metals salts of ruthenium oxo acids such as $K_2RuO_4$ or $KRuO_4$ or complexes such as RuHCl(CO)(PPh$_3$)$_3$, or as carbonyls of ruthenium, for example dodecacarbonyltrisruthenium or octadecacarbonylhexaruthenium or mixed forms in which CO is partly replaced by ligands of the formula PR$_3$, e.g. Ru(CO)$_3$(PPh$_3$)$_2$. Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt-caproate complex. Here too, the carbonyl complexes of cobalt such as octacarbonyldicobalt, dodecacarbonyltetracobalt and hexadecacarbonylhexacobalt can be used.

The abovementioned and further suitable compounds of transition metals, especially of group VIII transition metals are known in principle and are adequately described in the literature or can be prepared by a person skilled in the art by methods analogous to those for the known compounds.

Preferably, the transition metal or its salt and the ligand are brought in a molar ratio of from 10:1 to 1:100, more preferably from 1:1 to 1:100, even more preferably from 1:1 to 1:20, particularly preferably from 1:1 to 1:10 and in particular from 1:1.5 to 1:10, e.g. 1:2 to 1:10 or 1:3 to 1:10, into contact with each other.

Preferably, the catalyst is used in such an amount that the metal is applied in an amount of from 0.001 to 10 mol-%, more preferably 0.01 to 5 mol-%, even more preferably 0.05 to 4 mol-%, and in particular 0.1 to 3 mol-%, relative to 100 mol-% of compound II.

The carbonylation reaction is preferably carried out at from 1 to 100 bar, more preferably from >1 to 50 bar, even more preferably from 1.5 to 20 bar and in particular from 2 to 15 bar.

The carbonylation reaction is preferably carried out at elevated temperature, such as to 200° C., more preferably from 50 to 170° C. and in particular from 60 to 150° C.

The carbonylation reaction is preferably carried out in the presence of a base.

Suitable bases are inorganic bases, such as alkali metal hydroxides, for example lithium, sodium or potassium hydroxide, earth alkaline metal hydroxide such as magnesium or calcium hydroxide, alkali metal carbonates, for example lithium, sodium or potassium carbonate, earth alkaline metal carbonates such as magnesium or calcium carbonates, alkali metal hydrogencarbonates, for example lithium, sodium or potassium hydrogencarbonate, earth alkaline metal hydrogencarbonates such as magnesium or calcium hydrogencarbonates, or ammonia, and organic bases, such as amines, for example aliphatic monoamines such as ethylamine, diethylamine, triethylamine, dipropylamine, tripropylamine, butylamine, diethlisopropylamine and the like, aliphatic polyamines, such as ethylene diamine, propylene diamine, butylene diamine, tetramethylethylene diamine, diethylene triamine, tetraethylene triamine and the like, aromatic amines, such as diphenyl amine, alkanol amines, such as diethanol amine and triethanolamine, nitrogen-containing heterocyclic compounds, such as piperidine, piperazine, morpholine, pyridine, lutidine, picoline and the like, and alkoxides, such as sodium methoxide, sodium ethoxide, sodium propoxide or potassium tert-butanolate. Among the inorganic bases, preference is given to the carbonates, especially to sodium or potassium carbonate. Among the organic bases, amines and especially aliphatic mono- and polyamines, preferably diamines, are preferred. Among organic and inorganic bases, more preference is given to organic bases, among these amines and especially aliphatic mono- and polyamines, preferably diamines, being preferred.

The base is preferably used in an amount of 0.1 to 10, more preferably 0.5 to 5, and in particular 0.5 to 2 mole equivalents, relative to 1 mole of compound II. "Equivalents" in this case refers to the fact that some bases can accept more than one proton. For example a diamine can accept two protons and thus 1 mole of diamine relative to 1 mole of compound II corresponds to two base equivalents.

The carbonylation reaction is preferably carried out in a suitable solvent. Suitable solvents are those which dissolve sufficiently the reactants and do not negatively influence the reaction. Examples are aliphatic hydrocarbons, such as pentane, hexane, heptane, octane and petrolether, cycloaliphatic hydrocarbons, such as cyclohexane and cyclooctane, aromatic hydrocarbons, such as benzene, toluene, the xylenes, nitrobenzene, chlorobenzene and the dichloribenzenes, chlorinated alkanes, such as dichloromethane, chloroform, chloroethane and dichloroethane, ethers, such as diethylether, dipropylether, methyl-tert-butyl ether, methylisobutyl ether, tetrahydrofuran or dioxane, ketones, such as acetone, diethylketone or cyclohexanone, esters, such as ethylacetate, propylacetate, butylacetate, ethylpropionate or propylpropionate, amides, such as dimethylformamide or dimethylacetamide, dimethylsulfoxide, N-methylpyrrolidone and the like.

Alternatively, one of the above-listed amines (if this is liquid under the given reaction conditions) may be used as solvent.

However, preference is given to the above aromatic hydrocarbons and amides, toluene and DMF being specifically preferred.

The carbonylation reaction can be carried out in reaction vessels customary for such reactions, the reaction being configurable continuously, semicontinuously or batchwise.

If the carbonylation is carried out under positive pressure, it is suitably carried out in a reactor which can be pressurized, such as a pressure vessel, an autoclave or a pressurized reactor.

The reaction can for example be carried out by bringing the staring compound II, the catalyst and optionally a base in a reaction vessel into contact with each other, preferably in a solvent. The catalyst is either prepared previously in a separate step or acquired commercially, or is preferably prepared in situ by bringing a suitable transition metal compound, preferably a salt thereof, in the reaction vessel into contact with the desired ligand. Then hydrogen and carbon monoxide are introduced in the desired ratio until the desired pressure is reached. Alternatively, the desired pressure, if it is excess pressure, can also be obtained by introducing an inert gas, such as nitrogen, so that hydrogen and carbon can be used in a smaller amount without being wasted for the production of the required pressure. Hydrogen and carbon monoxide can be introduced either separately or as a mixture. The whole amount of hydrogen and carbon monoxide can be introduced from the beginning or the gases can be introduced by degrees during a part or the whole duration of the reaction, for example depending on consumption. The reaction is heated to the desired reaction temperature. Heating can be started yet during the mixing of the compound II, the catalyst and the optional base, during the introduction of hydrogen and carbon monoxide or only after all reagents (inclusive hydrogen and carbon monoxide) are present in the reaction vessel.

After completion of the reaction, the reaction vessel is generally cooled, if necessary, depressurized, if necessary, and the product is worked-up by customary methods, if desired, such as removing the catalyst, neutralizing optionally present amine, removing the solvent and if desired subjecting the obtained product to a purification step, such as chromatographic methods, recrystallization, extraction and the like.

For the production of compound III in process B, the carbonyl compound I obtained in the carbonylation reaction is converted into the imine compound III.

In case $R^1$ in compound III is H, compound I can for example be directly reacted with a compound $NH_2$—Y—$R^2$.

Compound I and the aminic compound $NH_2$—Y—$R^2$ are preferably used in a molar ratio of from 5:1 to 1:20, more preferably 1.5:1 to 1:10, even more preferably 1:1 to 1:5 and in particular 1:1 to 1:2.

This imination reaction can be carried out in the presence or absence of an acid. In general, the presence of an acid is dispensable if $NH_2$—Y—$R^2$ is an amine, i.e. Y is a bond and $R^2$ is $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$; phenyl which may be substituted by 1, 2, 3, 4 or radicals $R^{10}$; or a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$. In all other cases, and especially if Y is O, N—$R^3$ or $S(O)_n$ and $R^2$ has one of the above-given general definitions or if Y is a bond and $R^2$ is —$N(R^8)R^9$; —$N(R^8)C(=O)R^6$; —$Si(R^{14})_2R^{13}$; —$OR^7$; —$SR^7$; —$S(O)_mR^7$; —$S(O)_nN(R^8)R^9$; —$C(=O)R^6$; —$C(=O)OR^7$; —$C(=O)N(R^8)R^9$; —$C(=S)R^6$; —$C(=S)OR^7$, —$C(=S)N(R^8)R^9$ or —$C(=NR^8)R^6$, it is preferred to carry out the imination step in the presence of an acid.

Suitable acids are mineral acids, such as hydrochloric acid, hydrobromic acid, sulfuric acid, nitric acid or phosphoric acid, as well as organic acids, such as acetic acid, methylsulfonic acid or toluene sulfonic acid. Among these, preference is given to organic acids.

Especially in case that $NH_2$—Y—$R^2$ is a semicarbazide (Y is $NR^3$ and $R^2$ is —$C(O)NR^8R^9$) it is preferred to carry out the imination reaction in the presence of an acid and especially of acetic acid. In this specific case, the semicarbazide is preferably used in the form of its hydrochloride which is converted into the acetate in the presence of acetic acid.

Alternatively, in case that $NH_2$—Y—$R^2$ is a semicarbazide (Y is $NR^3$ and $R^2$ is —$C(O)NR^8R^9$) it is preferred to use the semicarbazide in the form of its hydrochloride which is converted into the acetate in the presence of acetic acid or sodium acetate.

The reaction may be carried out in a suitable solvent. Suitable solvents are all solvents listed above for the carbonylation reaction and also protic solvents, such as alcohols, for instance monobasic alcohols, e.g. methanol, ethanol, propanol, isopropanol, n-butanol, sec-butanol, isobutanol, tert-butanol or cyclohexanol, or di- or polybasic alcohols, such as glycols, e.g. ethylene glycol, propylene glycol, diethylene glycol, triethylleneglykol and the like.

If the aminic compound $NH_2$—Y—$R^2$ is liquid under the given reaction conditions, it may be used as a solvent, too. However it is preferred to use one of the above-listed solvents. Among these, preference is given to the above alcohols. A specific solvent is ethanol.

The imination reaction is preferably carried out at elevated temperatures, e.g. in the range of from 30 to 150° C., preferably from 40 to 120° C. and in particular from 50 to 100° C.

The water formed during the imination reaction may be removed in order to assist the reaction, e.g. by distilling it off or by using a water trap, but generally this is not necessary as the reaction mostly proceeds fast enough.

The work-up of the reaction can be carried out by customary means, such as neutralization of the acid, if present and removal of solvent and excess aminic compound $NH_2$—Y—$R^2$ or by isolating the desired compound III from the reaction mixture, e.g. by extraction or crystallization methods.

The preparation of compounds III, wherein $R^1$ is hydrogen can also be effected as a one-step (or one-pot) reaction by reacting the compound II with carbon monoxide and hydrogen in the presence of a transition metal complex and of the aminic compound $NH_2$—Y—$R^2$. This variant is especially interesting if basic aminic compounds $NH_2$—Y—$R^2$ are used, i.e. compounds wherein $NH_2$ or $NR^3$ are not directly neighboured to a CO, CS, $S(O)_m$ or another electron-withdrawing group. If the aminic compound $NH_2$—Y—$R^2$ is a simple and inexpensive amine, it may also replace the base optionally used in the carbonylation reaction.

For preparing compounds III wherein $R^1$ is not H, the compound I may be first subjected to a derivatization reaction on the aldehyde group before it is subjected to the imination reaction. For instance, the compound I may be reacted in a Grignard reaction with a Grignard reagent $R^1$—MgCl, $R^1$—MgBr or $R^1$—MgI, or may be reacted with another organometallic compound, such as an organic lithium compound $R^1$—Li. Preferably, $R^1$—MgCl or $R^1$—MgBr is used.

The Grignard reagent is generally prepared shortly before the reaction with compound I by reacting a halogenide $R^1$—Cl, $R^1$—Br or $R^1$—I with magnesium. Magnesium and halogenide are generally used in an approximately equimolar ratio. The reaction is generally carried out under customary conditions for this reaction type, i.e. in an inert, anhydrous and also alcohol-free solvent, such as anhydrous and alcohol-free ethers, e.g. diethylether, dibutylether, tetrahydrofuran or anisol, preferably under an inert atmosphere, such as argon or nitrogen. Generally, magnesium is placed in the inert solvent and the halogenide is added by degrees. The halogenide is generally added at such a rate that the reaction mixture refluxes smoothly. After completion of the addition the reaction is generally heated until all magnesium has dissolved. The obtained solution of the Grignard reagent may be used as such or diluted with another solvent which is inert for the following Grignard reaction, such as an aromatic hydrocarbon, e.g. toluene.

For the reaction with compound I may be carried out by either adding the Grignard reagent or another organometallic compound to the compound I or vice versa by adding compound I to the Grignard reagent or another organometallic compound. The reagents are generally present in an inert solvent, such as the above-named ethers or aromatic hydrocarbons. The reaction temperature depends on the reagents' reactivity and can vary in large ranges such as −80° C. to the boiling point of the reaction mixture. After completion of the reaction the mixture is quenched, e.g. by the addition of water or an acidic solution, such as diluted hydrochloric acid or aqueous ammoniumchloride.

The reaction yields an alcohol IV

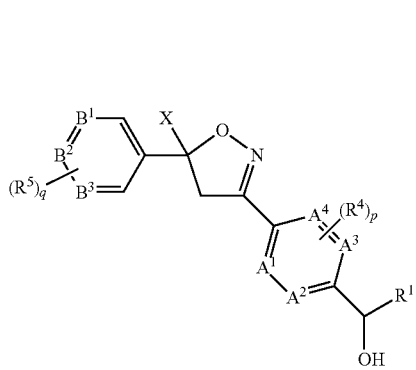
(IV)

This can be isolated from the reaction by customary methods, such as extraction or crystallization.

The alcohol is then oxidized to the ketone V

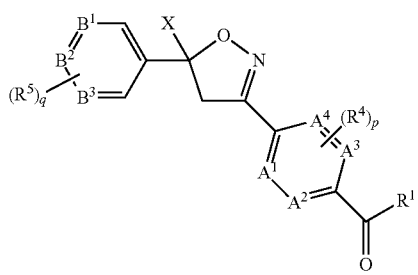
(V)

Oxidation can principally be carried out by using virtually all oxidizing reagent known for such systems, such as chromium compounds, especially Cr(VI) compounds, e.g. chromic acid, potassium dichromate, potassium dichromate/sulfuric acid, chromium trioxide, chromium trioxide/sulphuric acid/acetone, chromium trioxide/pyridinium complex or pyridinium chlorochromate, manganese compounds, such as potassium permanganate or manganese dioxide $MnO_2$, DMSO/oxalyl chloride (Swern reagent), halogen compounds, such as hypohalogenic acid or Dess-Martin-periodinane (DMP), tetrapropylammonium perruthenate (TPAP) or N-methylmorpholine oxide (NMO).

Specifically DMP is used.

The reaction conditions depend on the oxidation reagent used.

The ketone V can then be subjected to an imination reaction as described above for the compounds I wherein $R^1$ is H.

The compound of formula II can be prepared by cycloaddition of styrene compounds of formula 2 with nitrile oxides derived from oximes of formula 3 as outlined in scheme 1.

The reaction typically proceeds through the intermediacy of an in situ generated hydroxamic acid chloride by reaction with chlorine, hypochlorite, N-succinimide or chloramine-T. The hydroxamic acid chloride is combined with the oxime in the presence of styrene 2. Depending on the conditions, amine bases, such as pyridine or triethylamine may be necessary. The reaction can be run in a wide variety of solvents including DMF, toluene, dichloromethane, chlorobenzene, acetonitrile or the like.

Scheme 1

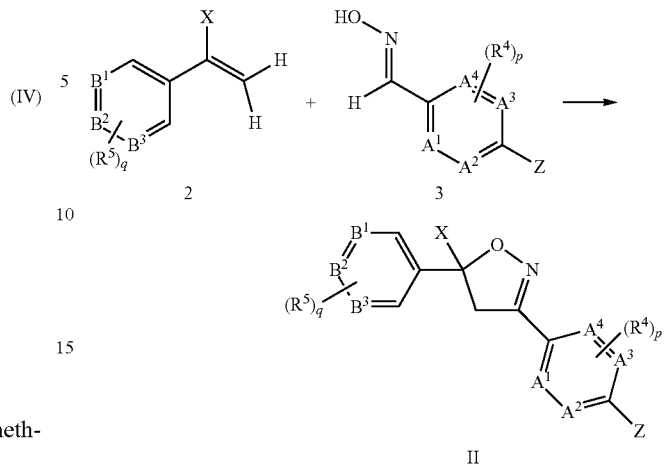

Compounds of formula II can also be prepared as outlined in scheme 2 by reacting enones of formula 4 with hydroxylamine. The preparation of compounds 4 is, for example, described in WO 2007/074789.

Scheme 2

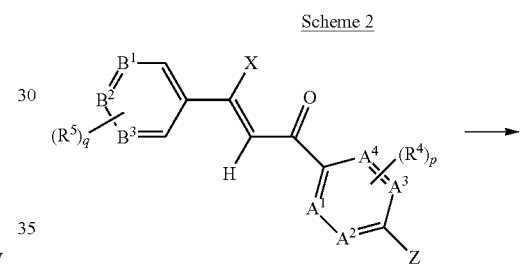

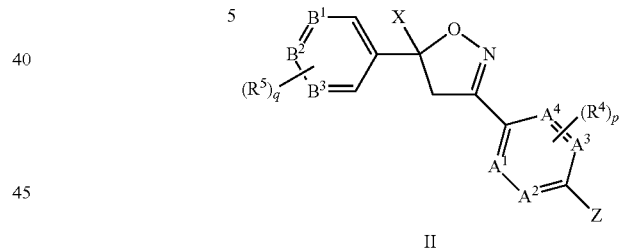

Compounds of formula II can also be prepared as outlined in scheme 3 by reacting ketones or thioketones 5 (W=O or S) with hydroxylamine. The preparation of compounds of type 5 is described, for example, in WO 2007/074789.

Scheme 3

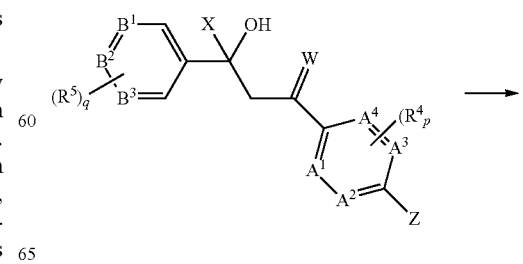

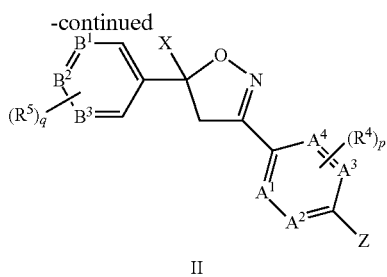

II

The process of the invention is particularly useful for producing compounds I and III and starting from compound II, wherein the variables have the following preferred meanings:

Preferably, at most two of $A^1$, $A^2$, $A^3$ and $A^4$ are N. In one embodiment, $A^1$, $A^2$, $A^3$ and $A^4$ are CH. In an alternative embodiment, $A^1$, $A^3$ and $A^4$ are CH and $A^2$ is N. In an alternative embodiment, $A^1$ and $A^4$ are CH and $A^2$ and $A^3$ are N. In an alternative embodiment, $A^1$ and $A^2$ are CH and $A^3$ and $A^4$ are N. In an alternative embodiment, $A^2$ and $A^4$ are CH and $A^1$ and $A^3$ are N.

More preferably, $A^4$ is CH.

More preferably, $A^1$ and $A^3$ are CH.

Even more preferably, $A^1$, $A^3$ and $A^4$ are CH and $A^2$ is CH or N and in particular CH. Specifically, all $A^1$, $A^2$, $A^3$ and $A^4$ are CH.

In a preferred embodiment, the ring comprising the groups $A^1$, $A^2$, $A^3$ or $A^4$ as ring members carries 0, 1 or 2, preferably 1 or 2 substituents $R^4$. In other words, p is preferably 0, 1 or 2, more preferably 1 or 2. In case $A^2$ is CH and p is 1, the substituent $R^4$ is preferably bound on the position of $A^2$ (or $A^3$, which is interchangeable with $A^2$ in case all of $A^1$, $A^2$, $A^3$ and $A^4$ are CH). In other words, $A^2$ is in this case preferably C—$R^4$. In case $A^2$ is N and p is 1, the substituent $R^4$ is preferably bound on the position of $A^3$. In other words, $A^3$ is in this case preferably C—$R^4$.

In case p is 2, two substituents $R^4$ bound on adjacent carbon atoms preferably form together a group selected from —CH$_2$CH$_2$CH$_2$CH$_2$— and —CH=CH—CH=CH— and more preferably —CH=CH—CH=CH—, thus yielding a fused phenyl ring.

Specifically, $A^1$, $A^3$ and $A^4$ are CH and $A^2$ is C—$R^4$. Alternatively $A^3$ and $A^4$ are CH and $A^1$ and $A^2$ are C—$R^4$.

Preferably, at most one of $B^1$, $B^2$ and $B^3$ is N. More preferably, $B^1$, $B^2$ and $B^3$ are CH or $B^1$ and $B^2$ are CH and $B^3$ is N. Specifically, $B^1$, $B^2$ and $B^3$ are CH.

q is preferably 0, 1, 2 or 3, more preferably 1, 2 or 3, even more preferably 2 or 3. If q is 3 and $B^1$, $B^2$ and $B^3$ are CH, then the three substituents $R^5$ are preferably bound in the positions of $B^1$, $B^2$ and $B^3$; $B^1$, $B^2$ and $B^3$ thus being C—$R^5$. If q is 2 and $B^1$, $B^2$ and $B^3$ are CH, then the two substituents $R^5$ are preferably bound in the positions of $B^1$ and $B^3$; $B^1$ and $B^3$ thus being C—$R^5$. $B^2$ in this case is preferably CH. In case $B^1$ and $B^2$ are CH and $B^3$ is N, q is preferably 1. In this case, $R^5$ is preferably bound in the position of $B^1$, $B^1$ thus being C—$R^5$.

Specifically, $B^1$, $B^2$ and $B^3$ are CH and q is 2 or 3, where in case q is 2, the two substituents $R^5$ are bound in the positions of $B^1$ and $B^3$; $B^1$ and $B^3$ thus being C—$R^5$, and where in case q is 3, the three substituents $R^5$ are bound in the positions of $B^1$, $B^2$ and $B^3$; $B^1$, $B^2$ and $B^3$ thus being C—$R^5$.

X is preferably selected from the group consisting of $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_1$-$C_4$-alkyl, $C_3$-$C_6$-cycloalkyl and $C_3$-$C_6$-halocycloalkyl. More preferably, X is selected from the group consisting of $C_1$-$C_4$-alkyl, $C_1$-$C_4$-haloalkyl, $C_3$-$C_6$-cycloalkyl and $C_3$-$C_6$-halocycloalkyl. Even more preferably, X is selected from the group consisting of $C_1$-$C_4$-alkyl and $C_1$-$C_4$-haloalkyl. In particular, X is $C_1$-$C_4$-haloalkyl, specifically $C_1$-$C_2$-haloalkyl and more specifically halomethyl, in particular fluoromethyl, such as fluoromethyl, difluoromethyl and trifluoromethyl, and is very specifically trifluoromethyl.

Y is preferably O, $NR^3$ or a chemical bond.

In one preferred embodiment, Y is O.

In an alternatively preferred embodiment, Y is $NR^3$. $R^3$ has one of the meanings given above or preferably one of the preferred meanings given below.

In an alternatively preferred embodiment, Y is a chemical bond.

More preferably, Y is O or $NR^3$. $R^3$ has one of the meanings given above or preferably one of the preferred meanings given below.

Specifically, Y is $NR^3$ and very specifically NH.

Preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, preferably 1 or 2, more preferably 1, radicals $R^{10}$;

where $R^7$, $R^8$, $R^9$ and $R^{10}$ have one of the meanings given above or in particular one of the preferred meanings given below and $R^{61}$ is hydrogen or has one of the meanings given above or in particular is hydrogen or has one of the preferred meanings given below for $R^6$.

Even more preferably, $R^1$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_1$-$C_{10}$-alkoxy; $C_1$-$C_{10}$-haloalkoxy; $C_3$-$C_8$-cycloalkyl which may be partially or fully halogenated and/or may be substituted by one or more, e.g. 1, 2, 3 or 4, preferably 1 or 2, more preferably 1, radicals $R^6$, and —C(=O)$R^6$; where $R^6$ has one of the meanings given above or in particular one of the preferred meanings given below.

In particular, $R^1$ is selected from the group consisting of hydrogen, cyano, $C_1$-$C_{10}$-alkyl, preferably $C_1$-$C_6$-alkyl, more preferably $C_1$-$C_4$-alkyl, which may be partially or fully halogenated and/or may be substituted by one or more, e.g. 1, 2, 3 or 4, preferably 1 or 2, more preferably 1, radicals $R^6$; $C_3$-$C_6$-cycloalkyl which may be partially or fully halogenated and/or may be substituted by one or more, e.g. 1, 2, 3 or 4, preferably 1 or 2, more preferably 1, radicals $R^6$, especially cyclopropyl; $C_1$-$C_4$-alkoxy; $C_1$-$C_4$-haloalkoxy, and —C(=O)$R^6$; where $R^6$ has one of the meanings given above or in particular one of the preferred meanings given below.

Specifically, $R^1$ is selected from the group consisting of hydrogen, $C_1$-$C_6$-alkyl which may be partially or fully halogenated and/or may be substituted by 1 or 2, preferably 1, radicals $R^6$, and $C_3$-$C_6$-cycloalkyl, especially cyclopropyl, which may be partially or fully halogenated and/or may be substituted by 1 or 2, preferably 1, radicals $R^6$, more specifically from hydrogen, $C_1$-$C_6$-alkyl and $C_3$-$C_6$-cycloalkyl, especially cyclopropyl and very specifically from hydrogen and $C_1$-$C_6$-alkyl, more specifically hydrogen and methyl.

In case $R^1$ is selected from $C_1$-$C_{10}$-alkyl, preferably $C_1$-$C_6$-alkyl, more preferably $C_1$-$C_4$-alkyl, which is substituted by one or more, e.g. 1, 2, 3 or 4, preferably 1 or 2, more preferably 1, radicals $R^6$, $R^6$ is more preferably selected from $C_3$-$C_6$-cycloalkyl, $C_3$-$C_6$-halocycloalkyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, more preferably from a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, even more preferably from a 5- or 6-membered saturated, partially unsaturated or aromatic heterocyclic ring containing 1, 2 or 3 heteroatoms selected from N, O and S, as ring members, where the heterocyclic ring may be substituted by one or more, e.g. 1, 2 or 3, preferably 1 or 2, more preferably 1, radicals $R^{10}$, in particular from a 5- or 6-membered heteroaromatic ring containing 1 heteroatom selected from N, O and S and optionally 1 or two further N atoms, as ring members, where the heteroaromatic ring may be substituted by one or more, e.g. 1, 2 or 3, preferably 1 or 2, more preferably 1, radicals $R^{10}$, and is specifically 6-membered heteroaromatic ring selected from pyridinyl, pyridazinyl, pyrimidinyl, pyrazinyl and 1,3,5-triazinyl, preferably from pyridyl and pyrimidinyl, where the heteroaromatic ring may be substituted by one or more, e.g. 1, 2 or 3, preferably 1 or 2, more preferably 1, radicals $R^{10}$, where $R^{10}$ has one of the meanings given above or in particular one of the preferred meanings given below.

Preferably, $R^2$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —$N(R^8)R^9$; —$N(R^8)C(\!=\!O)R^6$; —$Si(R^{14})_2R^{13}$; —$OR^7$; —$SR^7$; —$S(O)_mR^7$; —$S(O)_nN(R^8)R^9$; —$C(\!=\!O)R^6$; —$C(\!=\!O)OR^7$; —$C(\!=\!O)N(R^8)R^9$; —$C(\!=\!S)R^6$; —$C(\!=\!S)OR^7$; —$C(\!=\!S)N(R^8)R^9$; —$C(\!=\!NR^8)R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$; with the proviso that $R^2$ is not —$OR^7$ if Y is O.

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or two O, S and/or $NR^{18}$ and/or 1 or 2 of the $CH_2$ groups of the alkylene chain may be replaced by a group $C\!=\!O$, $C\!=\!S$ and/or $C\!=\!NR^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^7$, $R^8$, $R^9$, $R^{10}$, $R^{11}$, $R^{12}$, $R^{13}$, $R^{14}$ and $R^{18}$ have one of the meanings given above or in particular one of the preferred meanings given below and $R^{61}$ is hydrogen or has one of the meanings given above or in particular is hydrogen or has one of the preferred meanings given below for $R^6$.

In case Y is a chemical bond, $R^2$ is more preferably selected from a substituent bound via a heteroatom, such as —$N(R^8)R^9$; —$N(R^8)C(\!=\!O)R^6$; —$OR^7$; —$SR^7$; —$S(O)_mR^7$; —$S(O)_n N(R^8)R^9$ and an N-bound 3-, 4-, 5-, 6- or 7-membered saturated, partially unsaturated or aromatic heterocyclic ring containing 1 N atom as ring member and optionally 1 or 2 further heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is a chemical bond, $R^2$ is even more preferably selected from —$N(R^8)R^9$; —$N(R^8)C(\!=\!O)R^6$; —$OR^7$; —$SR^7$; —$S(O)_mR^7$ and $S(O)_nN(R^8)R^9$, in particular from —$N(R^8)R^9$; —$N(R^8)C(\!=\!O)R^6$; —$OR^7$ and —$SR^7$, and specifically from —$N(R^8)R^9$; —$N(R^8)C(\!=\!O)R^6$ and —$OR^7$, where $R^6$, $R^7$, $R^8$ and $R^9$ have one of the meanings given above or in particular one of the preferred meanings given below.

In case Y is not a chemical bond, $R^2$ is more preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —$C(\!=\!O)R^6$; —$C(\!=\!O)OR^7$; —$C(\!=\!O)N(R^8)R^9$; —$C(\!=\!S)R^6$; —$C(\!=\!S)OR^7$, —$C(\!=\!S)N(R^8)R^9$; —$C(\!=\!NR^8)R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is not a chemical bond, $R^2$ is even more preferably selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)$R^6$; —C(=S)O$R^7$; —C(=S)N($R^8$)$R^9$; —C(=N$R^8$)$R^6$, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is not a chemical bond, $R^2$ is in particular selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; —C(=O)$R^6$; —C(=O)O$R^7$; —C(=O)N($R^8$)$R^9$; —C(=S)N($R^8$)$R^9$; —C(=N$R^8$)$R^6$, phenyl which may be substituted by 1, 2, 3, 4 or 5, preferably 1 or 2 and in particular 1, radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

In case Y is not a chemical bond, $R^2$ is more particularly selected from the group consisting of hydrogen; $C_1$-$C_{10}$-alkyl, preferably $C_1$-$C_4$-alkyl, which may be partially or fully halogenated and/or may be substituted by one or more, e.g. 1, 2, 3 or 4, preferably 1 or 2, more preferably 1, radicals $R^6$; —C(=O)$R^6$, —C(=O)O$R^7$; —C(=O)N($R^8$)$R^9$; —C(=S)N($R^8$)$R^9$; and —C(=N$R^8$)$R^6$, where $R^6$, $R^7$, $R^8$ and $R^9$ have one of the meanings given above or in particular one of the preferred meanings given below.

In case Y is not a chemical bond, $R^2$ is specifically selected from the group consisting of hydrogen; $C_1$-$C_4$-alkyl, $C_1$-$C_4$-haloalkyl, in particular $C_1$-$C_4$-fluoroalkyl, $C_1$-$C_4$-alkyl which is substituted by one or more, e.g. 1, 2, 3 or 4, preferably 1 or 2, more preferably 1, radicals $R^{6a}$; —C(=O)$R^{6b}$, —C(=O)O$R^7$, —C(=O)N($R^8$)$R^9$, —C(=S)N($R^8$)$R^9$; —C(=N$R^8$)$R^6$ and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where
$R^{6a}$ is selected from CN, —C(=O)$R^{6b}$; —C(=O)N($R^8$)$R^9$, —C(=O)O$R^7$; phenyl which may be substituted by 1, 2, 3, 4 or 5 radicals $R^{10}$, a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, preferably from a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, more preferably from a 5- or 6-membered saturated, partially unsaturated or aromatic heterocyclic ring containing 1, 2 or 3 heteroatoms selected from N, O and S, as ring members, where the heterocyclic ring may be substituted by one or more, e.g. 1, 2 or 3, preferably 1 or 2, more preferably 1, radicals $R^{10}$, in particular from a 5- or 6-membered heteroaromatic ring containing 1 heteroatom selected from N, O and S and optionally 1 or two further N atoms, as ring members, where the heteroaromatic ring may be substituted by one or more, e.g. 1, 2 or 3, preferably 1 or 2, more preferably 1, radicals $R^{10}$, and is specifically 6-membered heteroaromatic ring selected from pyridinyl, pyridazinyl, pyrimidinyl, pyrazinyl and 1,3,5-triazinyl, preferably from pyridyl and pyrimidinyl, where the heteroaromatic ring may be substituted by one or more, e.g. 1, 2 or 3, preferably 1 or 2, more preferably 1, radicals $R^{10}$, where $R^{10}$ has one of the meanings given above or in particular one of the preferred meanings given below; and
$R^{6b}$ is selected from hydrogen, $C_1$-$C_6$-alkyl, $C_1$-$C_6$-haloalkyl, $C_3$-$C_6$-cycloalkyl, or has one of the meanings given for $R^{6a}$;
where $R^6$, $R^7$, $R^8$ and $R^9$ have one of the meanings given above or in particular one of the preferred meanings given below.

More specifically, $R^2$ is selected from the group consisting of hydrogen; $C_1$-$C_4$-alkyl; $C_1$-$C_4$-haloalkyl; a methyl group substituted by a radical $R^{6a}$ selected from CN, phenyl, which may carry 1, 2 or 3 substituents $R^{10a}$, —C(=O)$R^{6b}$; —C(=O)N($R^{8a}$)$R^{9a}$ and —C(=O)O$R^{7a}$; —C(=O)$R^{6c}$; —C(=O)N($R^{8a}$)$R^{9a}$; —C(=S)N($R^{8a}$)$R^{9a}$; —C(=N$R^{8a}$)$R^{6d}$ and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$,
where
$R^{6b}$ and $R^{6c}$ are independently selected from $C_1$-$C_4$-alkyl, $C_1$-$C_4$-haloalkyl, $C_3$-$C_6$-cycloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;
$R^{6d}$ is selected from N($R^{8a}$)$R^{9a}$;
$R^{7a}$ is selected from hydrogen, $C_1$-$C_4$-alkyl, $C_1$-$C_4$-haloalkyl, phenyl, benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;

each $R^{8a}$ is independently selected from hydrogen, cyano, $C_1$-$C_6$-alkyl which may be partially or fully halogenated and/or may be substituted by one or more radicals $R^{19}$, $C_2$-$C_4$-alkenyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —S(O)$_m$R$^{20}$, —S(O)$_n$N(R$^{21}$)R$^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and SO$_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy;

each $R^{9a}$ is independently selected from hydrogen, cyano, $C_1$-$C_6$-alkyl which may be partially or fully halogenated and/or may be substituted by one or more radicals $R^{19}$, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-halocycloalkyl-$C_1$-$C_4$-alkyl, —S(O)$_m$R$^{20}$, —S(O)$_n$N(R$^{21}$)R$^{22}$, phenyl, benzyl and a 5- or 6-membered saturated, partially unsaturated or aromatic heterocyclic ring containing 1, 2 or 3 heteroatoms or heteroatom groups selected from N, O, S, NO, SO and SO$_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy; or $R^{8a}$ and $R^{9a}$ together form a group =CR$^{11}$R$^{12}$; or $R^{8a}$ and $R^{9a}$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and SO$_2$, as ring members, where the heterocyclic ring may be substituted by one or more radicals $R^{10}$; and $R^{10a}$ is selected from halogen, CN, $C_1$-$C_4$-alkyl, $C_1$-$C_4$-haloalkyl, $C_1$-$C_4$-alkoxy and $C_1$-$C_4$-haloalkoxy;

where $R^{10}$, $R^{11}$, $R^{12}$ and $R^{19}$ have one of the general meanings given above or in particular one of the preferred meanings given below.

In the above preferred embodiment of $R^2$, $R^{11}$ is preferably hydrogen or methyl and $R^{12}$ is preferably $C_1$-$C_6$-alkoxy, $C_1$-$C_6$-haloalkoxy, —C(=O)R$^{19}$, —C(=O)OR$^{20}$, or —C(=O)N(R$^{21}$)R$^{22}$.

In the above preferred embodiment of $R^2$, $R^{9a}$, if it does not form together with $R^{8a}$ a group =CR$^{11}$R$^{12}$ or together with $R^{8a}$ and the N atom to which they are bound a heterocyclic ring, is preferably selected from hydrogen, cyano, $C_1$-$C_4$-alkyl, $C_1$-$C_4$-haloalkyl, cyclopropyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably hydrogen or $C_1$-$C_4$-alkyl.

In the above preferred embodiment of $R^2$, $R^{8a}$, if it does not form together with $R^{9a}$ a group =CR$^{11}$R$^{12}$ or together with $R^{9a}$ and the N atom to which they are bound a heterocyclic ring, is preferably selected from CN, $C_1$-$C_6$-alkyl; $C_1$-$C_6$-haloalkyl; $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl-$C_1$-$C_4$-alkyl; $C_3$-$C_6$-halocycloalkyl-$C_1$-$C_4$-alkyl; $C_3$-$C_8$-cycloalkyl which carries one radical $R^{19}$, —S(O)$_m$R$^{20}$; —S(O)$_n$N(R$^{21}$)R$^{22}$; phenyl; benzyl and a 5- or 6-membered saturated, partially unsaturated or aromatic heterocyclic ring containing 1, 2 or 3 heteroatoms or heteroatom groups selected from N, O, S, NO, SO and SO$_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

If $R^{8a}$ and $R^{9a}$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and SO$_2$, as ring members, this is preferably a 3, 5 or 6-membered saturated heterocyclic ring which may additionally containing 1 further heteroatom or heteroatom group selected from N, O, S, NO, SO and SO$_2$, as ring member.

In a particularly preferred embodiment of the invention, the combination of Y and $R^2$ is NR$^3$—CO—N(R$^8$)R$^9$. In this case, $R^3$ is preferably selected from hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably H or $C_1$-$C_4$-alkyl, and $R^8$ and $R^9$ have preferably one of the preferred meanings given below for $R^8$ and $R^9$ or have more preferably one of the general or preferred meanings given above for $R^{8a}$ and $R^{9a}$.

In an alternatively particularly preferred embodiment of the invention, the combination of Y and $R^2$ is NR$^3$—CS—N(R$^8$)R$^9$. In this case, $R^3$ is preferably selected from hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably H or $C_1$-$C_4$-alkyl, and $R^8$ and $R^9$ have preferably one of the preferred meanings given below for $R^8$ and $R^9$ or have more preferably one of the general or preferred meanings given above for $R^{8a}$ and $R^{9a}$.

In an alternatively particularly preferred embodiment of the invention, the combination of Y and $R^2$ is NR$^3$—CO—R$^6$. In this case, $R^3$ is preferably selected from hydrogen, $C_1$-$C_4$-alkyl, $C_1$-$C_4$-haloalkyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably H or $C_1$-$C_4$-alkyl, and $R^6$ has preferably one of the preferred meanings given below for $R^6$ or has more preferably one of the general or preferred meanings given above for $R^{6b}$ or $R^{6c}$. Specifically, $R^6$ is in this case selected from $C_3$-$C_6$-cycloalkyl and a 5- or 6-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

In an alternatively particularly preferred embodiment of the invention, the combination of Y and $R^2$ is NR$^3$—R$^2$, where $R^2$ is a 5- or 6-membered saturated, partially unsaturated or aromatic heterocyclic ring containing 1, 2 or 3 heteroatoms or heteroatom groups selected from N, O, S, NO, SO and SO$_2$, as ring members, where the heterocyclyl ring may carry 1, 2 or 3 substituents selected from halogen, CN, $C_1$-$C_4$-alkyl, $C_1$-$C_4$-haloalkyl, $C_1$-$C_4$-alkoxy, $C_1$-$C_4$-haloalkoxy and phenyl.

Preferably $R^3$ is selected from the group consisting of hydrogen; cyano; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —$N(R^8)R^9$; —$Si(R^{14})_2R^{13}$; —$OR^7$; —$SR^7$; —$S(O)_mR^7$; —$S(O)_nN(R^8)R^9$; —$C(=O)R^6$; —$C(=O)OR^7$; —$C(=O)N(R^8)R^9$; —$C(=S)R^6$; —$C(=S)OR^7$; —$C(=S)N(R^8)R^9$; —$C(=NR^8)R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or $R^2$ and $R^3$ together form a group =$CR^{11}R^{12}$; =$S(O)_mR^7$; =$S(O)_mN(R^8)R^9$; =$NR^8$; or =$NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or two O, S and/or $NR^{18}$ and/or 1 or 2 of the $CH_2$ groups of the alkylene chain may be replaced by a group C=O, C=S and/or C=$NR^{18}$; and/or the alkylene chain may be substituted by one or more, e.g. 1, 2, 3 or 4, preferably 1 or 2, more preferably 1, radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$, $R^{10}$, $R^{11}$, $R^{12}$, $R^{13}$, $R^{14}$ and $R^{18}$ have one of the meanings given above or in particular one of the preferred meanings given below.

More preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_{10}$-alkenyl which may be partially or fully halogenated and/or may be substituted by one or more, e.g. 1, 2, 3 or 4, preferably 1 or 2, more preferably 1, radicals $R^6$; $C_2$-$C_{10}$-alkynyl which may be partially or fully halogenated and/or may be substituted by one or more, e.g. 1, 2, 3 or 4, preferably 1 or 2, more preferably 1, radicals $R^6$; —$C(=O)R^6$; —$C(=O)OR^7$; —$C(=O)N(R^8)R^9$; —$C(=S)R^6$; —$C(=S)OR^7$; —$C(=S)N(R^8)R^9$; —$C(=NR^8)R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^6$, $R^7$, $R^8$, $R^9$ and $R^{10}$ have one of the meanings given above or in particular one of the preferred meanings given below.

Even more preferably, $R^3$ is selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —$C(=O)R^6$; —$C(=O)OR^7$; —$C(=O)N(R^8)R^9$; —$C(=S)R^6$; —$C(=S)OR^7$; —$C(=S)N(R^8)R^9$ and —$C(=NR^8)R^6$; where $R^6$, $R^7$, $R^8$ and $R^9$ have one of the meanings given above and in particular one of the preferred meanings given below.

In particular, $R^3$ is selected from the group consisting of hydrogen; $C_1$-$C_6$-alkyl which may be partially or fully halogenated and/or may be substituted by one or more, e.g. 1, 2, 3 or 4, preferably 1 or 2, more preferably 1, radicals $R^6$; —$C(=O)R^6$ and —$C(=O)N(R^8)R^9$; where $R^6$, $R^8$ and $R^9$ have one of the meanings given above and in particular one of the preferred meanings given below. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

More particularly, $R^3$ is selected from the group consisting of hydrogen, $C_1$-$C_4$-alkyl, $C_1$-$C_4$-haloalkyl and —$C(=O)R^6$, and is specifically selected from the group consisting of hydrogen, $C_1$-$C_4$-alkyl and $C_1$-$C_4$-haloalkyl, where $R^6$ has one of the meanings given above or in particular one of the preferred meanings given below and is specifically hydrogen or $C_1$-$C_4$-alkyl. Very specifically, $R^3$ is hydrogen.

Specifically, in the group —$C(R^1)=N$—Y—$R^2$, $R^1$ is hydrogen or $C_1$-$C_4$-alkyl, Y is NH and $R^2$ is $C(=O)NR^8R^9$, $C(=S)NR^8R^9$ or $C(=O)R^6$, where $R^6$, $R^8$ and $R^9$ have preferably one of the preferred meanings given below for $R^8$ and $R^9$ or have more preferably one of the general or preferred meanings given above for $R^{6b}$, $R^{6c}$, $R^{8a}$ and $R^{9a}$, or $R^2$ is a 5- or 6-membered saturated, partially unsaturated or aromatic heterocyclic ring containing 1, 2 or 3 heteroatoms or heteroatom groups selected from N, O, S, NO, SO and $SO_2$, as ring members, where the heterocyclyl ring may carry 1, 2 or 3 substituents selected from halogen, CN, $C_1$-$C_4$-alkyl, $C_1$-$C_4$-haloalkyl, $C_1$-$C_4$-alkoxy, $C_1$-$C_4$-haloalkoxy and phenyl.

Preferably, each $R^4$ is independently selected from Cl; F; cyano; nitro; —SCN; $SF_5$; $C_1$-$C_6$-alkyl which may be partially or fully halogenated and/or may be substituted by one or more, e.g. 1, 2, 3 or 4, preferably 1 or 2, more preferably 1, radicals $R^6$; $C_3$-$C_8$-cycloalkyl which may be partially or fully halogenated and/or may be substituted by one or more, e.g. 1, 2, 3 or 4, preferably 1 or 2, more preferably 1, radicals $R^6$; $C_2$-$C_6$-alkenyl which may be partially or fully halogenated and/or may be substituted by one or more, e.g. 1, 2, 3 or 4, preferably 1 or 2, more preferably 1, radicals $R^6$; $C_2$-$C_6$-alkynyl which may be partially or fully halogenated and/or may be substituted by one or more, e.g. 1, 2, 3 or 4, preferably 1 or 2, more preferably 1, radicals $R^6$; —$Si(R^{14})_2R^{13}$; —$OR^7$; —$OS(O)_nR^7$; —$SR^7$; —$S(O)_mR^7$; —$S(O)_nN(R^8)R^9$; —$N(R^8)R^9$; —$N(R^8)C(=O)R^6$; $C(=O)R^6$; —$C(=O)OR^7$; —$C(=NR^8)H$; —$C(=NR^8)R^6$; —$C(=O)N(R^8)R^9$; $C(=S)N(R^8)R^9$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$;

or two radicals $R^4$ bound on adjacent carbon atoms may be together a group selected from —$CH_2CH_2CH_2CH_2$—, —CH=CH—CH=CH—, —N=CH—CH=CH—, —CH=N—CH=CH—, —N=CH—N=CH—, —OCH$_2$CH$_2$CH$_2$—, —OCH═CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH═CHCH$_2$—, —CH$_2$CH$_2$O—, —CH═CHO—, —CH$_2$OCH$_2$—, —CH$_2$C(═O)O—, —C(═O)OCH$_2$—, —O(CH$_2$)O—, —SCH$_2$CH$_2$—, —SCH═CHCH$_2$—, —CH$_2$SCH$_2$CH$_2$—, —SCH$_2$CH$_2$S—, —SCH$_2$SCH$_2$—, —CH$_2$CH$_2$S—, —CH═CHS—, —CH$_2$SCH$_2$—, —CH$_2$C(═S)S—, —C(═S)SCH$_2$—, —S(CH$_2$)S—, —CH$_2$CH$_2$NR$^8$—, —CH$_2$CH═N—, —CH═CH—NR$^8$—, —OCH═N—, and —SCH═N—, thus forming, together with the carbon atoms to which they are bound, a 5- or 6-membered ring, where the hydrogen atoms of the above groups may be replaced by one or more, e.g. 1, 2, 3 or 4, preferably 1 or 2, more preferably 1, substituents selected from halogen, methyl, halomethyl, hydroxyl, methoxy and halomethoxy or one or more, e.g. 1 or 2, CH$_2$ groups of the above groups may be replaced by a C═O group, where R$^6$, R$^7$, R$^8$, R$^9$, R$^{10}$, R$^{13}$ and R$^{14}$ have one of the meanings given above or in particular one of the preferred meanings given below.

More preferably, each R$^4$ is independently selected from Cl; F; cyano; nitro; —SCN; C$_1$-C$_6$-alkyl which may be partially or fully halogenated and/or may be substituted by one or more, e.g. 1, 2, 3 or 4, preferably 1 or 2, more preferably 1, radicals R$^6$; C$_3$-C$_8$-cycloalkyl which may be partially or fully halogenated and/or may be substituted by one or more, e.g. 1, 2, 3 or 4, preferably 1 or 2, more preferably 1, radicals R$^6$; —OR$^7$; —OS(O)$_n$R$^7$; —SR$^7$; —S(O)$_m$R$^7$; —S(O)$_n$N(R$^8$)R$^9$; —N(R$^8$)R$^9$; C(═O)R$^6$; —C(═O)OR$^7$; —C(═NR$^8$)R$^6$; —C(═O)N(R$^8$)R$^9$; —C(═S)N(R$^8$)R$^9$ and phenyl which may be substituted by 1, 2, 3, 4 or 5 radicals R$^{10}$ or two radicals R$^4$ bound on adjacent carbon atoms may be together a group —CH═CH—CH═CH—; where R$^6$, R$^7$, R$^8$, R$^9$ and R$^{10}$ have one of the meanings given above or in particular one of the preferred meanings given below.

In particular, each R$^4$ is independently selected from Cl, F; cyano; C$_1$-C$_6$-alkyl; C$_1$-C$_6$-haloalkyl; C$_1$-C$_6$-alkoxy and C$_1$-C$_6$-haloalkoxy; or two radicals R$^4$ bound on adjacent carbon atoms may be together a group —CH═CH—CH═CH—.

More particularly, each R$^4$ is independently selected from Cl; F; cyano; C$_1$-C$_6$-alkyl, preferably C$_1$-C$_4$-alkyl, more preferably methyl; C$_1$-C$_4$-haloalkyl, preferably C$_1$-C$_2$-haloalkyl, more preferably CF$_3$; and C$_1$-C$_6$-alkoxy, preferably C$_1$-C$_4$-alkoxy, more preferably methoxy; or two radicals R$^4$ bound on adjacent carbon atoms may be together a group —CH═CH—CH═CH—.

Preferably, each R$^5$ is independently selected from the group consisting of Cl, F, cyano, nitro, —SCN, SF$_5$, C$_1$-C$_6$-alkyl, C$_1$-C$_6$-alkyl which may be partially or fully halogenated and/or may be substituted by one or more, e.g. 1, 2, 3 or 4, preferably 1 or 2, more preferably 1, radicals R$^6$, C$_3$-C$_8$-cycloalkyl which may be partially or fully halogenated and/or may be substituted by one or more, e.g. 1, 2, 3 or 4, preferably 1 or 2, more preferably 1, radicals R$^6$, C$_2$-C$_6$-alkenyl which may be partially or fully halogenated and/or may be substituted by one or more, e.g. 1, 2, 3 or 4, preferably 1 or 2, more preferably 1, radicals R$^6$, C$_2$-C$_6$-alkynyl which may be partially or fully halogenated and/or may be substituted by one or more, e.g. 1, 2, 3 or 4, preferably 1 or 2, more preferably 1, radicals R$^6$, Si(R$^{14}$)$_2$R$^{13}$, OR$^7$, OS(O)$_n$R$^7$, S(O)$_m$R$^7$, NR$^8$R$^9$, N(R$^8$)C(═O)R$^6$, C(═O)R$^6$, C(═O)OR$^7$, C(═NR$^8$)R$^6$, C(═S)NR$^6$, phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, preferably 1 or 2, more preferably 1, radicals R$^{10}$, where R$^6$, R$^7$, R$^8$, R$^9$, R$^{10}$, R$^{13}$ and R$^{14}$ have one of the meanings given above or in particular one of the preferred meanings given below.

More preferably, each R$^5$ is independently selected from the group consisting of Cl, F, cyano, nitro, C$_1$-C$_6$-alkyl, C$_1$-C$_6$-alkyl which may be partially or fully halogenated and/or may be substituted by one or more, e.g. 1, 2, 3 or 4, preferably 1 or 2, more preferably 1, radicals R$^6$, OR$^7$, phenyl which may be substituted by 1, 2, 3, 4 or 5 radicals R$^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more, e.g. 1, 2, 3 or 4, preferably 1 or 2, more preferably 1, radicals R$^{10}$, where R$^6$, R$^7$ and R$^{10}$ have one of the meanings given above or in particular one of the preferred meanings given below.

Even more preferably, each R$^5$ is independently selected from the group consisting of Cl, F, C$_1$-C$_6$-alkyl, C$_1$-C$_6$-haloalkyl, C$_1$-C$_6$-alkoxy and C$_1$-C$_6$-haloalkoxy, in particular from Cl, F, C$_1$-C$_4$-alkyl and C$_1$-C$_2$-haloalkyl and is specifically chlorine or C$_1$-C$_2$-haloalkyl, especially CF$_3$; or is specifically chlorine or fluorine.

In case R$^6$ is a substituent on an alkyl, alkenyl or alkynyl group, it is preferably selected from the group consisting of cyano, azido, nitro, —SCN, SF$_5$, C$_3$-C$_8$-cycloalkyl, C$_3$-C$_8$-halocycloalkyl, —Si(R$^{14}$)$_2$R$^{13}$, —OR$^7$, —OSO$_2$R$^7$, —SR$^7$, —S(O)$_m$R$^7$, —S(O)$_n$N(R$^8$)R$^9$, —N(R$^8$)R$^9$, —C(═O)N(R$^8$)R$^9$, —C(═S)N(R$^8$)R$^9$, —C(═O)R$^7$, —C(═O)R$^{19}$, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$; or two geminally bound radicals R$^6$ together form a group selected from ═CR$^{11}$R$^{12}$, ═S(O)$_m$R$^7$, ═S(O)$_m$N(R$^8$)R$^9$, ═NR$^8$, ═NOR$^7$ and ═NNR$^8$; or two radicals R$^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and SO$_2$, as ring members, where R$^7$, R$^8$, R$^9$, R$^{10}$, R$^{11}$, R$^{12}$, R$^{13}$, R$^{14}$ and R$^{19}$ have one of the meanings given above or in particular one of the preferred meanings given below.

In case R$^6$ is a substituent on an alkyl, alkenyl or alkynyl group, it is more preferably selected from the group consisting of cyano, C$_3$-C$_8$-cycloalkyl, C$_3$-C$_8$-halocycloalkyl, —OR$^7$, —SR$^7$, —C(═O)N(R$^8$)R$^9$, —C(═S)N(R$^8$)R$^9$, —C(═O)OR$^7$, —C(═O)R$^{19}$, phenyl which may be substituted by 1, 2, 3, 4 or 5 radicals R$^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$; where R$^7$, R$^8$, R$^9$ and R$^{10}$ have one of the meanings given above or in particular one of the preferred meanings given below.

In case R$^6$ is a substituent on an alkyl, alkenyl or alkynyl group, it is even more preferably selected from the group consisting of cyano, C$_3$-C$_6$-cycloalkyl, C$_3$-C$_6$-halocycloalkyl, C$_1$-C$_4$-alkoxy, C$_1$-C$_4$-haloalkoxy, C$_1$-C$_4$-alkylthio, $C_1$-$C_4$-haloalkylthio, —C(=O)N($R^8$)$R^9$, —C(=S)N($R^8$)$R^9$, —C(=O)O$R^7$, —C(=O)$R^{19}$, phenyl which may be substituted by 1, 2, 3, 4 or radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;
where $R^{10}$ has one of the meanings given above or in particular one of the preferred meanings given below.

In case $R^6$ is a substituent on an alkyl, alkenyl or alkynyl group, it is in particular selected from the group consisting of cyano, $C_3$-$C_6$-cycloalkyl, $C_3$-$C_6$-halocycloalkyl, —C(=O)N($R^8$)$R^9$, —C(=S)N($R^8$)$R^9$, —C(=O)O$R^7$, —C(=O)$R^{19}$, phenyl which may be substituted by 1, 2, 3, 4 or 5 radicals $R^{10}$, and a 5- or 6-membered heteroaromatic ring containing 1, 2 or 3 heteroatoms selected from N, O and S, as ring members, where the heteroaromatic ring may be substituted by one or more radicals $R^{10}$;
where $R^{10}$ has one of the meanings given above or in particular one of the preferred meanings given below.

In case $R^6$ is a substituent on a cycloalkyl group, it is preferably selected from the group consisting of cyano, azido, nitro, —SCN, $SF_5$, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —Si($R^{14}$)$_2$$R^{13}$, —O$R^7$, —OS$O_2$$R^7$, —S$R^7$, —S(O)$_m$$R^7$, —S(O)$_n$N($R^8$)$R^9$, —N($R^8$)$R^9$, —C(=O)N($R^8$)$R^9$, —C(=S)N($R^8$)$R^9$, —C(=O)O$R^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
or two geminally bound radicals $R^6$ together form a group selected from =C$R^{11}$$R^{12}$ =S(O)$_m$$R^7$, =S(O)$_m$N($R^8$)$R^9$, =N$R^8$, =NO$R^7$ and =NN$R^8$;
or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members, where $R^7$, $R^8$, $R^9$, $R^{10}$, $R^{11}$, $R^{12}$, $R^{13}$ and $R^{14}$ have one of the meanings given above or in particular one of the preferred meanings given below.

In case $R^6$ is a substituent on a cycloalkyl group, it is more preferably selected from the group consisting of halogen, cyano, $C_1$-$C_6$-alkyl, $C_1$-$C_6$-haloalkyl, $C_1$-$C_6$-alkoxy-$C_1$-$C_6$-alkyl, —O$R^7$, —OS$O_2$$R^7$, —S$R^7$, —S(O)$_m$$R^7$, —S(O)$_n$N($R^8$)$R^9$, —N($R^8$)$R^9$, —C(=O)N($R^8$)$R^9$, —C(=S)N($R^8$)$R^9$, —C(=O)O$R^7$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^7$, $R^8$, $R^9$ and $R^{10}$ have one of the meanings given above or in particular one of the preferred meanings given below.

In case $R^6$ is a substituent on a cycloalkyl group, it is even more preferably selected from the group consisting of halogen, $C_1$-$C_4$-alkyl, $C_1$-$C_3$-haloalkyl, $C_1$-$C_4$-alkoxy and $C_1$-$C_3$-haloalkoxy. In particular, $R^6$ as a substituent on a cycloalkyl group is selected from halogen, $C_1$-$C_4$-alkyl and $C_1$-$C_3$-haloalkyl.

In case $R^6$ is a substituent on C(=O), C(=S) or C(=N$R^8$), it is preferably selected from the group consisting of hydrogen, $C_1$-$C_6$-alkyl, $C_1$-$C_6$-haloalkyl, $C_1$-$C_6$-alkoxy-$C_1$-$C_6$-alkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, —O$R^7$, —S$R^7$, —N($R^8$)$R^9$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^7$, $R^8$, $R^9$ and $R^{10}$ have one of the meanings given above or in particular one of the preferred meanings given below.

In case $R^6$ is a substituent on C(=O), C(=S) or C(=N$R^8$), it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^{10}$ has one of the meanings given above or in particular one of the preferred meanings given below.

In case $R^6$ is a substituent on C(=O), C(=S) or C(=N$R^8$), it is more preferably selected from the group consisting of $C_1$-$C_6$-alkyl, $C_1$-$C_6$-haloalkyl, $C_3$-$C_8$-cycloalkyl, $C_3$-$C_8$-halocycloalkyl, $C_1$-$C_6$-alkoxy, $C_1$-$C_6$-haloalkoxy, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^{10}$ has one of the meanings given above or in particular one of the preferred meanings given below.

In case $R^6$ is a substituent on C(=O), C(=S) or C(=N$R^8$), it is even more preferably selected from the group consisting of $C_1$-$C_4$-alkyl, $C_1$-$C_3$-haloalkyl, $C_3$-$C_6$-cycloalkyl, $C_3$-$C_6$-halocycloalkyl, $C_1$-$C_4$-alkoxy, $C_1$-$C_3$-haloalkoxy, phenyl which may be substituted by 1, 2, 3, 4 or 5 radicals $R^{10}$, a 5- or 6-membered heteroaromatic ring containing 1, 2 or 3 heteroatoms selected from N, O and S, as ring members, where the heteroaromatic ring may be substituted by one or more radicals $R^{10}$ and a 5- or 6-membered saturated heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$;
where $R^{10}$ has one of the meanings given above or in particular one of the preferred meanings given below.

Preferably, each $R^7$ is independently selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more, e.g. 1, 2, 3 or 4, preferably 1 or 2, more preferably 1, radicals $R^{10}$, where $R^{10}$ has one of the meanings given above or in particular one of the preferred meanings given below.

More preferably, each $R^7$ is independently selected from the group consisting of hydrogen, $C_1$-$C_6$-alkyl, $C_1$-$C_6$-haloalkyl, phenyl which may be substituted by 1, 2, 3, 4 or 5 radicals $R^{10}$; and a 5- or 6-membered heteroaromatic ring containing 1, 2 or 3 heteroatoms selected from N, O and S, as ring members, where the heteroaromatic ring may be substituted by one or more radicals $R^{10}$; where $R^{10}$ has one of the meanings given above or in particular one of the preferred meanings given below.

$R^8$ and $R^9$ are independently of each other and independently of each occurrence preferably selected from the group consisting of hydrogen, cyano, $C_1$-$C_6$-alkyl which may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, $C_3$-$C_8$-cycloalkyl, $C_3$-$C_8$-halocycloalkyl, $C_3$-$C_8$-cycloalkyl-$C_1$-$C_6$-alkyl, $C_3$-$C_8$-cycloalkyl which carries one or more radicals $R^{19}$, $S(O)_m R^{20}$, $S(O)_n NR^{21}R^{22}$, phenyl which may be substituted by 1, 2, 3, 4 or radicals $R^{10}$, benzyl wherein the phenyl moiety may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$; where $R^{10}$ has one of the meanings given above or in particular one of the preferred meanings given below; or $R^8$ and $R^9$ together form a group $=CR^{11}R^{12}$; or $R^8$ and $R^9$, together with the nitrogen atom to which they are bound, form a 3-, 4-, 5-, 6- or 7-membered saturated, partially unsaturated or aromatic, preferably a saturated, heterocyclic ring which may additionally containing 1 or 2 further heteroatoms or heteroatom groups selected from N, O, S, NO, SO and $SO_2$, as ring members, where the heterocyclic ring may be substituted by one or more radicals $R^{10}$.

In the above preferred embodiment of $R^8$ and $R^9$, $R^{11}$ is preferably hydrogen or methyl and $R^{12}$ is preferably $C_1$-$C_6$-alkoxy, $C_1$-$C_6$-haloalkoxy, —C(=O)R^{19}, —C(=O)OR^{20}, or —C(=O)N(R^{21})R^{22}.

In the above preferred embodiment of $R^8$ and $R^9$, $R^9$, if it does not form together with $R^8$ a group $=CR^{11}R^{12}$ or together with $R^8$ and the N atom to which they are bound a heterocyclic ring, is preferably selected from hydrogen, cyano, $C_1$-$C_4$-alkyl, $C_1$-$C_4$-haloalkyl, cyclopropyl, $C_1$-$C_4$-alkylcarbonyl, $C_1$-$C_4$-haloalkylcarbonyl, $C_1$-$C_4$-alkoxycarbonyl and $C_1$-$C_4$-haloalkoxycarbonyl and is more preferably hydrogen or $C_1$-$C_4$-alkyl.

In the above preferred embodiment of $R^8$ and $R^9$, $R^8$, if it does not form together with $R^9$ a group $=CR^{11}R^{12}$ or together with $R^9$ and the N atom to which they are bound a heterocyclic ring, is preferably selected from CN, $C_1$-$C_6$-alkyl; $C_1$-$C_6$-haloalkyl; $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl-$C_1$-$C_4$-alkyl; $C_3$-$C_6$-halocycloalkyl-$C_1$-$C_4$-alkyl; $C_3$-$C_8$-cycloalkyl which carries one or more radicals $R^{19}$; —S(O)_m R^{20}; —S(O)_n N(R^{21})R^{22}; phenyl; benzyl and a 5- or 6-membered saturated, partially unsaturated or aromatic heterocyclic ring containing 1, 2 or 3 heteroatoms or heteroatom groups selected from N, O, S, NO, SO and $SO_2$, as ring members, where the phenyl or heterocyclyl rings in the three last-mentioned radicals may carry 1, 2 or 3 substituents selected from halogen, CN, $C_1$-$C_4$-alkyl, $C_1$-$C_4$-haloalkyl, $C_1$-$C_4$-alkoxy and $C_1$-$C_4$-haloalkoxy.

If $R^8$ and $R^9$, together with the nitrogen atom to which they are bound, form a 3-, 4-, 5-, 6- or 7-membered saturated, partially unsaturated or aromatic heterocyclic ring which may additionally containing 1 or 2 further heteroatoms or heteroatom groups selected from N, O, S, NO, SO and $SO_2$, as ring members, this is preferably a 3, 5 or 6-membered saturated heterocyclic ring which may additionally containing 1 further heteroatom or heteroatom group selected from N, O, S, NO, SO and $SO_2$, as ring member.

Specifically, $R^8$ and $R^9$ are independently of each other and independently of each occurrence selected from the group consisting of hydrogen, $C_1$-$C_6$-alkyl, $C_1$-$C_6$-haloalkyl, $C_1$-$C_4$-alkyl which carries one radical $R^{19}$; $C_2$-$C_6$-alkenyl; $C_2$-$C_6$-haloalkenyl; $C_2$-$C_4$-alkenyl which is substituted by one radical $R^{19}$; $C_3$-$C_6$-cycloalkyl; $C_3$-$C_6$-halocycloalkyl; $C_3$-$C_6$-cycloalkyl-$C_1$-$C_4$-alkyl; $C_3$-$C_6$-halocycloalkyl-$C_1$-$C_4$-alkyl; $C_3$-$C_8$-cycloalkyl which carries one or more radicals $R^{19}$; and a 5- or 6-membered heterocyclic ring containing 1, 2 or 3 heteroatoms or heteroatom groups selected from N, O, S, NO, SO and $SO_2$, as ring members, where the heterocyclic ring may be substituted by one or more radicals $R^{10}$. More specifically, $R^9$ is hydrogen or $C_1$-$C_4$-alkyl and $R^8$ has one of the meanings specified above.

Preferably, each $R^{10}$ is independently selected from the group consisting of Cl, F, cyano, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, —OR^{20}, —SR^{20}, —S(O)_m R^{20}, —S(O)_n N(R^{21})R^{22}, —N(R^{21})R^{22}, C(=O)R^{19}, —C(=O)OR^{20}, —C(=O)N(R^{21})R^{22}, phenyl which may be substituted by 1, 2, 3, 4 or 5 radicals independently selected from Cl, F, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from Cl, F, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from —CH_2CH_2CH_2CH_2—, —CH=CH—CH=CH—, —N=CH—CH=CH—, —CH=N—CH=CH—, —N=CH—N=CH—, —OCH_2CH_2CH_2—, —OCH=CHCH_2—, —CH_2OCH_2CH_2—, —OCH_2CH_2O—, —OCH_2OCH_2—, —CH_2CH_2CH_2—, —CH=CHCH_2—, —CH_2CH_2O—, —CH=CHO—, —CH_2OCH_2—, —CH_2C(=O)O—, —C(=O)OCH_2—, and —O(CH_2)O—, thus forming, together with the atoms to which they are bound, a 5- or 6-membered ring, where the hydrogen atoms of the above groups may be replaced by one or more substituents selected from Cl, F, methyl, halomethyl, hydroxyl, methoxy and halomethoxy or one or more $CH_2$ groups of the above groups may be replaced by a C=O group, where $R^{19}$, $R^{20}$, $R^{21}$ and $R^{22}$ have one of the general meanings given above or in particular one of the preferred meanings given below.

More preferably, each $R^{10}$ is independently selected from the group consisting of Cl, F, cyano, $C_1$-$C_{10}$-alkyl which may be partially or fully halogenated and/or may be substituted by one or more radicals $R^{19}$, —OR^{20}, —N(R^{21})R^{22}, C(=O)R^{19}, —C(=O)OR^{20}, —C(=O)N(R^{21})R^{22}, phenyl which may be substituted by 1, 2, 3, 4 or 5 radicals independently selected from Cl, F, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from N, O, S, NO, SO and $SO_2$, as ring members, which may be substituted by one or more radicals independently selected from Cl, F, cyano, nitro, $C_1$-$C_6$-alkyl, $C_1$-$C_6$-haloalkyl, $C_1$-$C_6$-alkoxy and $C_1$-$C_6$-haloalkoxy;

where $R^{19}$, $R^{20}$, $R^{21}$ and $R^{22}$ have one of the general meanings given above or in particular one of the preferred meanings given below.

Even more preferably, each $R^{10}$ is independently selected from the group consisting of Cl, F, $C_1$-$C_4$-alkyl, $C_1$-$C_4$-haloalkyl, $C_1$-$C_4$-alkoxy and $C_1$-$C_4$-haloalkoxy. In particular, each $R^{10}$ is independently selected from the group consisting of Cl, F, $C_1$-$C_4$-alkyl and $C_1$-$C_4$-haloalkyl and is specifically Cl or F, more specifically chlorine.

Preferably, $R^{11}$ and $R^{12}$ are, independently of each other and independently of each occurrence, selected from the group consisting of hydrogen, halogen, $C_1$-$C_6$-alkyl and $C_1$-$C_6$-haloalkyl. More preferably, $R^{11}$ and $R^{12}$ are, independently of each other and independently of each occurrence, selected from the group consisting of hydrogen, halogen and $C_1$-$C_6$-alkyl and in particular from the group consisting of hydrogen and halogen. Specifically, they are hydrogen.

Preferably, $R^{13}$ and $R^{14}$ are, independently of each other and independently of each occurrence, selected from $C_1$-$C_4$-alkyl and are in particular methyl.

Preferably, $R^{15}$ and $R^{16}$ are, independently of each other and independently of each occurrence, selected from the group consisting of $C_1$-$C_6$-alkyl, $C_1$-$C_6$-haloalkyl and phenyl which may be substituted by 1, 2, 3, 4, or 5 radicals $R^{10}$; where $R^{10}$ has one of the general or in particular one of the preferred meanings given above.

Preferably, each $R^{17}$ is independently selected from the group consisting of $C_1$-$C_6$-alkyl, $C_1$-$C_6$-haloalkyl, $C_3$-$C_8$-cycloalkyl, $C_3$-$C_8$-halocycloalkyl, phenyl and benzyl. More preferably, each $R^{17}$ is independently selected from the group consisting of $C_1$-$C_6$-alkyl, $C_1$-$C_6$-haloalkyl and phenyl and is in particular $C_1$-$C_4$-alkyl or $C_1$-$C_3$-haloalkyl.

Preferably, each $R^{18}$ is independently selected from the group consisting of hydrogen; $C_1$-$C_{10}$-alkyl which may be partially or fully halogenated and/or may be substituted by one or more, e.g. 1, 2, 3 or 4, preferably 1 or 2, more preferably 1, radicals $R^6$; —C(=O)$R^6$; —C(=O)$OR^7$; —C(=O)N($R^8$)$R^9$; —C(=S)$R^6$; —C(=S)$OR^7$; —C(=S)N($R^8$)$R^9$ and —C(=N$R^8$)$R^6$; where $R^6$, $R^7$, $R^8$ and $R^9$ have one of the general or in particular one of the preferred meanings given above.

More preferably, each $R^{18}$ is selected from the group consisting of hydrogen; $C_1$-$C_6$-alkyl which may be partially or fully halogenated and/or may be substituted by one or more, e.g. 1, 2, 3 or 4, preferably 1 or 2, more preferably 1, radicals $R^6$; —C(=O)$R^6$ and —C(=O)N($R^8$)$R^9$; where $R^6$, $R^8$ and $R^9$ have one of the general or in particular one of the preferred meanings given above. Preferably, in this case, $R^6$ as a $C_1$-$C_6$-alkyl substituent, is selected from CN, $C_3$-$C_6$-cycloalkyl, $C_3$-$C_6$-halocycloalkyl, $C_1$-$C_6$-alkoxy, $C_1$-$C_6$-haloalkoxy, $C_1$-$C_6$-alkylthio, $C_1$-$C_6$-haloalkylthio and a 5- or 6-membered hetaryl ring containing 1, 2 or 3 heteroatoms selected from N, O and S as ring members and being optionally substituted by 1, 2 or 3 radicals $R^{10}$. In this case, $R^6$ as a CO substituent, is preferably selected from $C_1$-$C_6$-alkyl, $C_1$-$C_6$-haloalkyl, $C_1$-$C_6$-alkoxy and $C_1$-$C_6$-haloalkoxy. In this case, $R^8$ and $R^9$ are preferably selected from hydrogen and $C_1$-$C_6$-alkyl.

In particular, each $R^{18}$ is selected from the group consisting of hydrogen, $C_1$-$C_4$-alkyl, $C_1$-$C_4$-haloalkyl and —C(=O)$R^6$, and is specifically selected from the group consisting of hydrogen, $C_1$-$C_4$-alkyl and —C(=O)$R^6$, where $R^6$ has one of the general or in particular one of the preferred meanings given above and is specifically $C_1$-$C_4$-alkyl.

In case $R^{19}$ is a substituent on an alkyl, alkenyl or alkynyl group, it is preferably selected from the group consisting of cyano, $C_3$-$C_6$-cycloalkyl, $C_3$-$C_6$-halocycloalkyl, —$OR^{20}$, $SR^{20}$, $S(O)_m R^{20}$, —C(=O)N($R^{21}$)$R^{22}$, —C(=S)N($R^{21}$)$R^{22}$, —C(=O)$OR^{20}$, —C(=O)$R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$;
where
$R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;
$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and
$R^{21}$ and $R^{22}$, independently of each other and independently of each occurrence, are selected from hydrogen, $C_1$-$C_4$-alkyl, $C_1$-$C_4$-haloalkyl, $C_3$-$C_6$-cycloalkyl, $C_3$-$C_6$-halocycloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a cycloalkyl group, it is preferably selected from the group consisting of cyano, $C_1$-$C_4$-alkyl, $C_1$-$C_4$-haloalkyl, $C_3$-$C_6$-cycloalkyl, $C_3$-$C_6$-halocycloalkyl, —C(=O)N($R^{21}$)$R^{22}$, —C(=S)N($R^{21}$)$R^{22}$, —C(=O)$OR^{20}$, —C(=O)$R^{20}$, phenyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$;
where
$R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;
$R^{20}$ is selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; and
$R^{21}$ and $R^{22}$, independently of each other and independently of each occurrence, are selected from hydrogen, $C_1$-$C_4$-alkyl, $C_1$-$C_4$-haloalkyl, phenyl, benzyl, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$.

In case $R^{19}$ is a substituent on a C(=O) group, it is preferably selected from the group consisting of hydrogen, $C_1$-$C_4$-alkyl, $C_1$-$C_4$-haloalkyl, $C_3$-$C_6$-cycloalkyl, $C_3$-$C_6$-halocycloalkyl, $C_3$-$C_6$-cycloalkyl-$C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{20}$ is preferably selected from the group consisting of hydrogen, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_6$-cycloalkyl, $C_3$-$C_6$-halocycloalkyl, $C_3$-$C_6$-cycloalkyl- $C_1$-$C_4$-alkyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy.

$R^{21}$ and $R^{22}$, independently of each other and independently of each occurrence, are preferably selected from the group consisting of hydrogen, $C_1$-$C_6$-alkyl, $C_1$-$C_6$-haloalkyl, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, benzyl which may be substituted by 1, 2, 3, 4 or 5 radicals $R^{10}$, and a 5- or 6-membered heterocyclic ring containing 1, 2 or 3 heteroatoms or heteroatom groups selected from N, O, S, NO, SO and $SO_2$, as ring members, where the rings in the three last-mentioned radicals may be substituted by one or more radicals $R^{10}$; where $R^{10}$ is selected from halogen, cyano, $C_1$-$C_4$-alkyl, $C_1$-$C_4$-haloalkyl, $C_1$-$C_4$-alkoxy and $C_1$-$C_4$-haloalkoxy;

or $R^{21}$ and $R^{22}$, together with the nitrogen atom to which they are bound, may form a 5- or 6-membered saturated, partially unsaturated or aromatic heterocyclic ring which may additionally containing 1 or 2 further heteroatoms or heteroatom groups selected from N, O, S, NO, SO and $SO_2$, as ring members, where the heterocyclic ring may be substituted by one or more radicals selected from halogen, $C_1$-$C_6$-alkyl, $C_1$-$C_6$-haloalkyl, $C_1$-$C_6$-alkoxy and $C_1$-$C_6$-haloalkoxy.

Specifically, process B refers to the preparation of compounds of the formula III-1

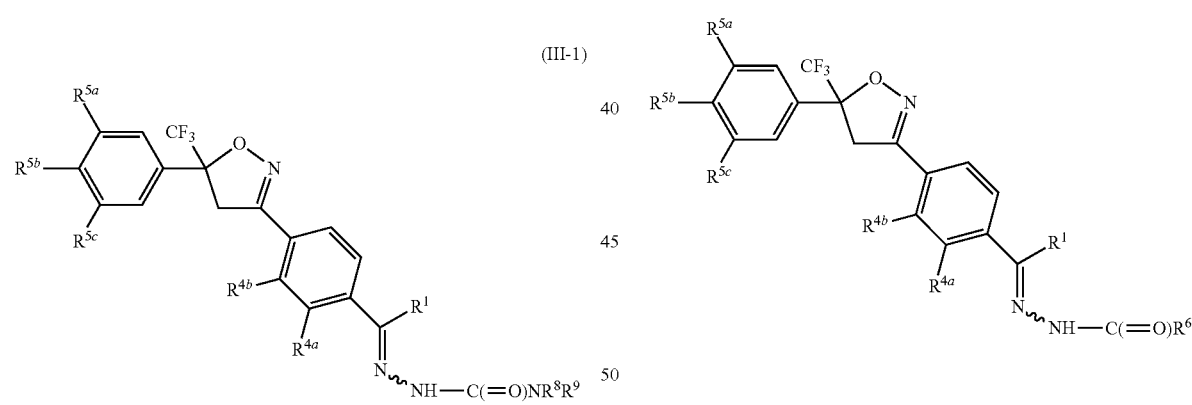

(III-1)

wherein $R^1$ is hydrogen or $C_1$-$C_4$-alkyl;

$R^{5a}$, $R^{5b}$, $R^{5c}$ are hydrogen or have one of the general or in particular one of the preferred meanings given above for $R^5$;

$R^{4a}$ and $R^{4b}$, independently of each other, are hydrogen or have one of the general or in particular one of the preferred meanings given above for $R^4$; and $R^8$ and $R^9$ have one of the general or in particular one of the preferred meanings given above.

In an alternative specific embodiment, process B refers to the preparation of compounds of the formula III-2

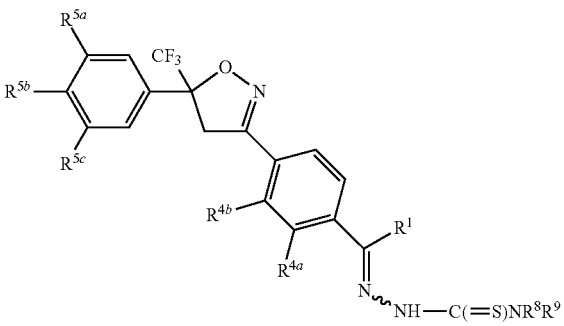

(III-2)

wherein $R^1$ is hydrogen or $C_1$-$C_4$-alkyl;

$R^{5a}$, $R^{5b}$, $R^{5c}$ are hydrogen or have one of the general or in particular one of the preferred meanings given above for $R^5$;

$R^{4a}$ and $R^{4b}$, independently of each other, are hydrogen or have one of the general or in particular one of the preferred meanings given above for $R^4$; and $R^8$ and $R^9$ have one of the general or in particular one of the preferred meanings given above.

In an alternative specific embodiment, process B refers to the preparation of compounds of the formula III-3

(III-3)

wherein $R^1$ is hydrogen or $C_1$-$C_4$-alkyl;

$R^{5a}$, $R^{5b}$, $R^{5c}$ are hydrogen or have one of the general or in particular one of the preferred meanings given above for $R^5$;

$R^{4a}$ and $R^{4b}$, independently of each other, are hydrogen or have one of the general or in particular one of the preferred meanings given above for $R^4$; and $R^6$ has one of the general or in particular one of the preferred meanings given above and is specifically selected from $C_3$-$C_6$-cycloalkyl, $C_3$-$C_6$-halocycloalkyl, a 5- or 6-membered heteroaromatic ring containing 1, 2 or 3 heteroatoms selected from N, O and S, as ring members, where the heteroaromatic ring may be substituted by one or more radicals $R^{10}$ and a 5- or 6-membered saturated heterocyclic ring containing 1, 2 or 3 heteroatoms or heteroatom groups selected from N, O, S, NO, SO and SO$_2$, as ring members, where the heterocyclic ring may be substituted by one or more radicals R$^{10}$, where R$^{10}$ has one of the general or inparticular one of the preferred meanings given above.

In an alternative specific embodiment, process B refers to the preparation of compounds of the formula III-4

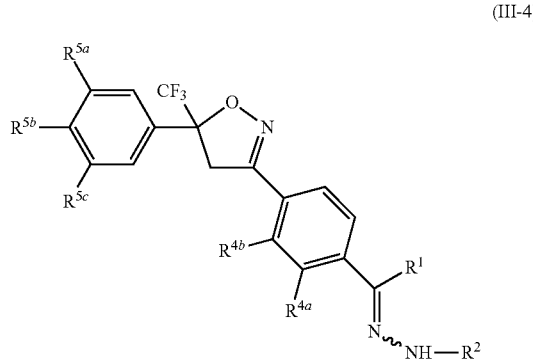

(III-4)

wherein
R$^1$ is hydrogen or C$_1$-C$_4$-alkyl;
R$^{5a}$, R$^{5b}$, R$^{5c}$ are hydrogen or have one of the general or in particular one of the preferred meanings given above for R$^5$;
R$^{4a}$ and R$^{4b}$, independently of each other, are hydrogen or have one of the general or in particular one of the preferred meanings given above for R$^4$; and
R$^2$ is a 5- or 6-membered saturated, partially unsaturated or aromatic heterocyclic ring containing 1, 2 or 3 heteroatoms or heteroatom groups selected from N, O, S, NO, SO and SO$_2$, as ring members, where the heterocyclyl ring may carry 1, 2 or 3 substituents selected from halogen, CN, C$_1$-C$_4$-alkyl, C$_1$-C$_4$-haloalkyl, C$_1$-C$_4$-alkoxy, C$_1$-C$_4$-haloalkoxy and phenyl.

By the method of the invention it is possible to produce the important intermediate of formula II in a simple and industrially applicable method. Moreover, the method requires less catalyst than the prior art methods.

The invention also refers to compounds obtainable by the method of the invention, especially compounds of formulae I and III or an enantiomer, diastereoisomer and/or an agriculturally acceptable salt thereof and specifically to every singly compound listed below in the examples (compounds C) and their enantiomers, diastereoisomers and/or an agriculturally acceptable salts.

The invention further relates to an agricultural composition comprising at least one imine compound of the formula III as defined above, obtainable by the process according to the invention, or an enantiomer, diastereoisomer and/or an agriculturally acceptable salt thereof, and at least one inert liquid and/or solid agriculturally acceptable carrier.

The invention also relates to a veterinary composition comprising at least one imine compound of the formula III as defined above, obtainable by the process according to the invention, or an enantiomer, diastereoisomer and/or a veterinarily acceptable salt thereof, and at least one inert liquid and/or solid veterinarily acceptable carrier.

Moreover, the invention relates to the use of an imine compound of formula III as defined above, obtainable by the process according to the invention, or an enantiomer, diastereoisomer and/or an agriculturally or veterinarily acceptable salt thereof, for combating invertebrate pests.

Another aspect of the invention is the use of an imine compound of formula III as defined above, obtainable by the process according to the invention, or an enantiomer, diastereoisomer and/or a veterinarily acceptable salt thereof, for treating or protecting an animal from infestation or infection by invertebrate pests.

A further aspect of the invention is plant propagation material, comprising at least one compound of the formula III as defined above, obtainable by the process according to the invention, or an enantiomer, diastereoisomer and/or an agriculturally acceptable salt thereof.

A preferred plant propargation material is seeds.

The invention will now be illustrated by following non-limiting examples.

EXAMPLES

Compounds were characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution:acetonitrile+0.1% trifluoroacetic acid (TFA)/water+0.1% trifluoroacetic acid (TFA) in a ratio of from 5:95 to 95:5 in 5 minutes at 40° C.

$^1$H-NMR, respectively $^{13}$C-NMR: The signals are characterized by chemical shift (ppm) vs. tetramethylsilane, respectively CDCl$_3$ or DMSO-d$_6$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet, dd=doublet of doublet and s=singulett.

S. Synthesis Examples

S.1 Synthesis of 4-[5-(3,5-dichloro-phenyl)-5-trifluoromethyl-4,5-dihydro-isoxazol-3-yl]-2-methyl-benzaldehyde-4-trifluoroethylsemicarbazone (Compound I-1 of table C.1; see below)

Step 1: Synthesis of 4-[5-(3,5-dichloro-phenyl)-5-trifluoromethyl-4,5-dihydro-isoxazol-3-yl]-2-methyl-benzaldehyde A reaction autoclave was charged with 3-(4-bromo-3-methyl-phenyl)-5-(3,5-dichlorophenyl)-5-trifluoromethyl-4,5-dihydro-isoxazole (0.10 g, 0.22 mmol), palladium dichloride cyclooctadiene complex (1.6 mg, 2.5 mol-%), xanthphos (9.7 mg, 7.5 mol-%), N,N,N',N'-tetramethylethylene diamine (19.3 mg, 0.75 equiv.) and DMF (2 mL) and purged with synthesis gas (carbon monoxide:hydrogen=1:1) to 5 bar. The reaction autoclave was heated to 100° C. for 16 h and then cooled to ambient temperature. After release of the pressure, the reaction mixture was concentrated under reduced pressure and the residue was purified by flash chromatography on silica gel to yield the title compound (13 mg, 15%).

Alternative Step 1: Synthesis of 4-[5-(3,5-dichloro-phenyl)-5-trifluoromethyl-4,5-dihydro-isoxazol-3-yl]-2-methyl-benzaldehyde A reaction autoclave was charged with 3-(4-bromo-3-methyl-phenyl)-5-(3,5-dichlorophenyl)-5-trifluoromethyl-4,5- dihydro-isoxazole 8.2 g, 18 mmol), palladium(II) acetate (13.4 mg, 59.7 μm), cataCXium (107.4 mg), N,N,N',N'-tetramethylethylene diamine (1.6 g) and toluene (7.9 g) and purged with synthesis gas (carbon monoxide:hydrogen=1:1) to 5 bar. The reaction autoclave was pressurized to 10 bar synthesis gas and was heated to 120° C. for 18 h and then cooled to ambient temperature. After release of the pressure, the reaction mixture was concentrated under reduced pressure and the residue was purified by flash chromatography on silica gel to yield the title compound (3.4 g, 37%).

Characterization by GC-MS (DB-XLB 30 m×0.25 mm, 0.25 μM film, helium 2 mL/min 50-10-260/10-10-300, 0.5 μM/split 10:1, injector 250° C.): 26.750 min, m/z=401 (TOF MS FI+)

Step 2: Synthesis of 4-[5-(3,5-dichloro-phenyl)-5-trifluoromethyl-4,5-dihydro-isoxazol-3-yl]-2-methyl-benzaldehyde-4-trifluoroethylsemicarbazone A mixture of 4-[5-(3,5-dichloro-phenyl)-5-trifluoromethyl-4,5-dihydro-isoxazol-3-yl]-2-methyl-benzaldehyde (72.5 g, 0.18 mol) and 4-trifluoroethyl semicarbazide hydrochloride (39.92 g, 0.21 mol) in ethanol (50 mL) and glacial acetic acid (40 mL) was heated at 70° C. over night. After this, water was added until the clear solution became turbid, then MTBE (10 mL) was added and the mixture was allowed to cool to ambient temperature. The resulting precipitate was filtered and washed with water to obtain the title compound (84.10 g, 86%).

Characterization by HPLC-MS: 4.281 min, M=541.00
Characterization by $^1$H-NMR (500 MHz, CDCl$_3$):
δ[delta]=2.52 (s, 3H), 3.71 (d, 1H), 4.03 (m, 2H), 4.11 (d, 1H), 6.46 (dd, 1H), 7.44 (s, 1H), 7.50-7.58 (m, 3H), 7.80 (d, 1H), 8.01 (s, 1H), 9.40 (s, 1H) ppm.

S.2 Synthesis of (E)- and (Z)-1-{4-[5-(3,5-dichloro-phenyl)-5-trifluoromethyl-4,5-dihydro-isoxazol-3-yl]-2-methyl-phenyl}-ethanone-4-trifluoroethylsemicarbazone (Compounds 1-19 and 1-57 of Table C.1; See Below)

Step 1: Synthesis of 1-{4-[5-(3,5-dichloro-phenyl)-5-trifluoromethyl-4,5-dihydro-isoxazol-3-yl]-2-methyl-phenyl}-ethanol To a solution of 4-[5-(3,5-dichloro-phenyl)-5-trifluoromethyl-4,5-dihydro-isoxazol-3-yl]-2-methyl-benzaldehyde (i.e. the product of example S.1, Step 1, 0.50 g) and lithium chloride (53 mg, 1.24 mmol, 1.00 equiv.) in THF (15 mL) was added a solution of methyl magnesium bromide (1.78 mL, 1.4 M in THF/toluene, 2.49 mmol, 2.00 equiv.) at −70° C.

After 1 h at this temperature, the mixture was allowed to warm to room temperature and was quenched with a saturated aqueous NH$_4$Cl solution. The layers were separated and extracted with toluene. Combined organic layers were dried over Na$_2$SO$_4$ and evaporated. The residue was purified by flash chromatography on silica gel to afford the title compound (0.20 g, 38%).

Characterization by HPLC-MS: 4.301 min, M=418.05

Step 2: Synthesis of 1-{4-[5-(3,5-dichloro-phenyl)-5-trifluoromethyl-4,5-dihydro-isoxazol-3-yl]-2-methyl-phenyl}-ethanone To a solution of 1-{4-[5-(3,5-dichloro-phenyl)-5-trifluoromethyl-4,5-dihydro-isoxazol-3-yl]-2-methyl-phenyl}-ethanol (i.e. the product of example S.2, Step 1, 160 mg, 0.38 mmol) in CH$_2$Cl$_2$ (10 mL) was added Dess-Martin-Periodinane (243 mg, 0.57 mmol, 1.5 equiv.) in small portions. The mixture was stirred at room temperature over night, then saturated aqueous NaHCO$_3$-solution was added and the mixture was left at room temperature for 1 h. The layers were separated and the organic layer was washed with water, dried over Na$_2$SO$_4$ and evaporated in vacuum to give the title compound (120 mg, 75%), which was used in the next reaction without further purification.

Characterization by HPLC-MS: 4.572 min, M=415.95

Step 3: Synthesis of (E)- and (Z)-1-{4-[5-(3,5-dichloro-phenyl)-5-trifluoromethyl-4,5-dihydro-isoxazol-3-yl]-2-methyl-phenyl}-ethanone-4-trifluoroethylsemicarbazone A mixture of 1-{4-[5-(3,5-dichloro-phenyl)-5-trifluoromethyl-4,5-dihydro-isoxazol-3-yl]-2-methyl-phenyl}-ethanone (1.37 g) and 4-trifluoroethyl semicarbazide hydrochloride (0.729 g) in ethanol (1 mL) and glacial acetic acid (0.5 mL) was heated at 70° C. for 6 h. After cooling, the solvents were evaporated in vacuum. Ethyl acetate was added, and the organic layer was washed with water. After drying over Na$_2$SO$_4$, the solvent was evaporated and the residue was chromatographed on silica gel to afford the title compounds (Z-isomer elutes first, 300 mg, E-isomer elutes second, 400 mg, total yield 38%).

Z-Isomer:
Characterization by HPLC-MS: 4.497 min, M=555.00
Characterization by $^1$H-NMR (400 MHz, DMSO-d$^6$):
δ [delta]=2.16 (s, 3H), 2.17 (s, 3H), 3.87 (m, 2H), 4.29 (d, 1H), 4.36 (d, 1H), 7.26 (d, 1H), 7.34 (m, 1H), 7.64-7.69 (m, 4H), 7.82 (m, 1H), 8.52 (s, 1H) ppm.

E-Isomer:
Characterization by HPLC-MS: 4.531 min, M=555.05

Compound 1-1 and the intermediate aldehyde were also obtained when MeSkatOX, TPP, TPPit, tBuOMeTPPit, BINAP, CyH$_3$P, cataCXium, Complex 130, Complex 34 or Complex 128 was used instead of Xanthphos.

The compounds of the following examples were synthesized analogously.

C. Compound Examples

C.1 Compound Examples 1

Compound examples 1-1 to 1-95 correspond to compounds of formula C.1:

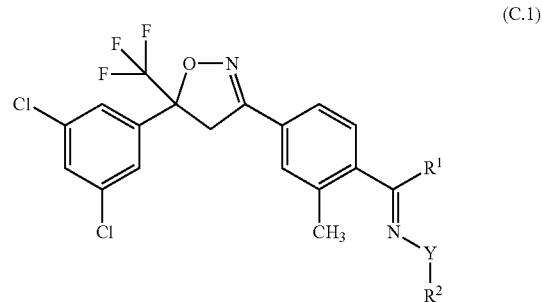

(C.1)

wherein R$^1$, R$^2$ and Y of each synthesized compound is defined in one row of table C.1 below.

TABLE C.1

| Compound Ex. | R¹ | R² | Y | $R_t$ (min) | [M + H] |
|---|---|---|---|---|---|
| 1-1 | H | C(=O)NH—CH₂CF₃ | NH | 4.281 | 541.00 |
| 1-2 | H | C(=O)NH-3-thiolyl-1,1-dioxide | NH | 4.092 | 577.05 |
| 1-3 | H | C(=O)—NH—CH₃ | NH | 4.193 | 473.05 |
| 1-4 | H | C(=O)NH—CH₂CH₃ | NH | 4.308 | 487.05 |
| 1-5 | H | C(=O)NH—CH₂CH(CH₃)₂ | NH | 4.575 | 515.05 |
| 1-6 | H | C(=O)NH—CH₂CH₂-thiophene-2-yl | NH | 4.597 | 569.05 |
| 1-7 | H | C(=O)NH—CH₂-furan-2-yl | NH | 4.368 | 538.70 |
| 1-8 | H | C(=O)—NH-cyclopropyl | NH | 4.324 | 499.05 |
| 1-9 | H | C(=O)NH—CH₂CH₂-2-pyridyl | NH | 3.627 | 563.80 |
| 1-10 | H | C(=O)NH—CH₂-tetrahydro-furan-2-yl | NH | 4.284 | 542.80 |
| 1-11 | H | C(=O)NH—CH₂CH₂CH₂OCH₃ | NH | 4.278 | 530.80 |
| 1-12 | H | C(=O)—NH—CH₂-cyclopropyl | NH | 4.452 | 513.05 |
| 1-13 | H | C(=O)NH—CH₂CH₂OCH₃ | NH | 4.183 | 516.80 |
| 1-14 | H | C(=O)NH—CH₂CH₂CH₃ | NH | 4.422 | 500.80 |
| 1-15 | H | C(=O)NH—CH₂CH₂CH₂CH₃ | NH | 4.572 | 514.80 |
| 1-16 | H | C(=O)NH—CH₂CH₂CH₂CH₂CH₃ | NH | 4.722 | 528.80 |
| 1-17 | H | C(=O)NH—CH₂CH₂CH(CH₃)₂ | NH | 4.698 | 528.80 |
| 1-18 | H | C(=O)NH—CH₂CH₂CH₂-1,3-imidazole-1-yl | NH | 3.604 | 566.80 |
| 1-19 | CH₃ | C(=O)NH—CH₂CF₃ (Z)-isomer | NH | 4.474 | 555.00 |
| 1-20 | H | C(=O)-pyrrolidine-1-yl | NH | 4.175 | 513.10 |
| 1-21 | H | C(=O)NH—CH₂CH₂CF₃ | NH | 4.507 | 555.10 |
| 1-22 | H | C(=O)NH-pyridine-3-yl | NH | 3.746 | 536.00 |
| 1-23 | H | C(=O)-morpholine-4-yl | NH | 4.039 | 529.00 |
| 1-24 | H | C(=O)NH—CH₂CH₂SCH₃ | NH | 4.456 | 533.00 |
| 1-25 | H | C(=O)NH—CH₂-pyridine-4-yl | NH | 3.659 | 550.00 |
| 1-26 | H | C(=O)NH-pyridine-4-yl | NH | 3.770 | 536.00 |
| 1-27 | H | C(=O)NH—CH₂-2-chloropyridine-5-yl | NH | 4.437 | 586.00 |
| 1-28 | H | C(=O)NH—CH₂-pyridine-2-yl | NH | 3.701 | 550.00 |
| 1-29 | H | C(=O)—NH-cyclopentyl | NH | 4.729 | 527.05 |
| 1-30 | H | C(=O)NH—CH(CH₃)₂ | NH | 4.527 | 501.05 |
| 1-31 | H | C(=O)-thiomorpholine-4-yl | NH | 4.281 | 545.05 |
| 1-32 | H | C(=O)—NH-cyclohexyl | NH | 4.840 | 541.00 |
| 1-33 | H | C(=O)NH—CH₂CHF₂ | NH | 4.331 | 523.00 |
| 1-34 | H | C(=O)NH—CH₂C(=O)NH—CH₂CF₃ | NH | 4.218 | 598.05 |
| 1-35 | H | C(=O)NH—CH₂CH₂SCF₃ | NH | 4.634 | 586.90 |
| 1-36 | H | C(=O)NH—CH₂CH=CCl₂ | NH | 4.703 | 568.95 |
| 1-37 | H | C(=O)NH-2-trifluoromethyl-thiazole-4-yl | NH | 4.920 | 610.00 |
| 1-38 | H | C(=O)NH—CH₂CH=CH-4-chlorophenyl | NH | 4.971 | 609.00 |
| 1-39 | H | C(=O)NH-2-chloropyridine-4-yl | NH | 4.522 | 571.95 |
| 1-40 | H | C(=O)NH—CH₂-2-chloropyrimidine-4-yl | NH | 4.342 | 585.05 |
| 1-41 | H | C(=O)NH-pyridazine-4-yl | NH | 3.773 | 537.05 |
| 1-42 | H | C(=O)NH—CH₂-pyrimidine-4-yl | NH | 4.002 | 551.00 |
| 1-43 | H | C(=O)NH—CH₂-pyrimidine-2-yl | NH | 4.081 | 551.00 |
| 1-44 | H | C(=O)N(CH₃)—CH₂CF₃ | NH | 4.291 | 555.00 |
| 1-45 | H | C(=O)NH—CH₂-2-chloropyridine-4-yl | NH | 4.342 | 584.00 |
| 1-46 | H | C(=O)NH-3-chloropyridine-4-yl | NH | 2.180 | 571.90 |
| 1-47 | H | C(=O)NH-3-chloropyridazine-6-yl hydrochloride | NH | ¹H-NMR (400 MHz, DMSO-d⁶): δ [delta] = 3.34 (s, 3H), 4.35 (d 1H), 4.40 (d, 1H), 7.60-7.75 (m, 5H), 7.88 (s, 1H), 7.95-8.04 (m, 1H), 8.34 (m, 1H), 8.97 (d, 1H), 9.04 (d, 1H), 12.42 (m, 1H) ppm. | |
| 1-48 | H | C(=O)NH-pyrimidine-4-yl | NH | 3.912 | 537.00 |
| 1-49 | H | C(=O)NH₂ | NH | 3.997 | 459.0 |
| 1-50 | H | C(=O)NH-1,2,4-triazole-3-yl | NH | 3.893 | 526.05 |
| 1-51 | H | C(=O)NH—CH₂CH₂S(=O)₂CH₃ | NH | 4.028 | 565.05 |
| 1-52 | H | C(=O)NH-3-chloropyridine-2-yl | NH | 4.352 | 569.95 |
| 1-53 | H | C(=O)NH—CH₂C(=O)NH-cyclopropyl | NH | 3.979 | 556.00 |
| 1-54 | H | C(=O)NH—CH₂C(=O)N(CH₃)₂ | NH | 4.012 | 544.00 |
| 1-55 | H | C(=O)NH—CH₂C(=O)NH—CH₃ | NH | 3.853 | 530.00 |
| 1-56 | H | C(=O)NH—CH₂C(=O)NH—CH(CH₃)₂ | NH | 4.123 | 558.10 |
| 1-57 | CH₃ | C(=O)NH—CH₂CF₃ (E)-isomer | NH | 4.531 | 555.05 |
| 1-58 | H | C(=O)NH—CH₂CH₂S(=O)₂CF₃ | NH | 4.414 | 618.90 |
| 1-59 | H | C(=O)NH—CH₂C(=O)NH—CH₂CH₃ | NH | 3.951 | 544.00 |

TABLE C.1-continued

| Compound Ex. | R¹ | R² | Y | $R_t$ (min) | [M + H] |
|---|---|---|---|---|---|
| 1-60 | H | C(=O)-5-chloro-1,2,4-triazole-3-yl | NH | 4.249 | 544.95 |
| 1-61 | H | C(=O)NH-6-chloropyridine-2-yl | NH | 4.813 | 570.00 |
| 1-62 | H | C(=O)NH—CH₂CH=CH₂ | NH | 4.318 | 499.00 |
| 1-63 | H | C(=O)N(CH₃) CH₂CH₃ | NH | 4.067 | 501.00 |
| 1-64 | H | C(=O)NH-thiazole-4-yl | NH | 4.409 | 541.95 |
| 1-65 | H | C(=O)NH-2-chlorothiazole-4-yl | NH | 4.921 | 576.00 |
| 1-66 | H | C(=O)NH-4-chloropyridine-2-yl | NH | 3.965 | 569.95 |
| 1-67 | H | C(=S)NH—CH₂CF₃ | NH | 4.620 | 556.95 |
| 1-68 | H | C(=S)NH—CH₃ | NH | 4.704 | 489.00 |
| 1-69 | H | C(=O)NH—CH₂CH₂OC₆H₅ | NH | 4.620 | 579.00 |
| 1-70 | H | C(=O)NH—CH₂C₆H₅ | NH | 4.559 | 549.00 |
| 1-71 | H | C(=O)NH—CH(CH₃)CH₂OCH₃ | NH | 4.369 | 531.00 |
| 1-72 | H | C(=O)NH—CH₂CH₂CF=CF₂ | NH | 4.501 | 567.00 |
| 1-73 | H | C(=S)NH₂ | NH | 4.144 | 474.95 |
| 1-74 | H | C(=O)NH—CH(CH₃)cyclopropyl | NH | 4.586 | 527.00 |
| 1-75 | H | C(=O)NH—CH₂-pyridine-3-yl | NH | 3.567 | 550.00 |
| 1-76 | H | 4-CH₃-thiazole-2-yl | NH | 4.110 | 513.00 |
| 1-77 | H | pyridine-2-yl | NH | 3.709 | 493.00 |
| 1-78 | H | C(=O)NH—CH(CH₃)CH₂OC₆H₅ | NH | 4.725 | 593.00 |
| 1-79 | H | C(=O)NH-1-(C₆H₅)cyclopropyl 1-yl | NH | 4.638 | 575.00 |
| 1-80 | H | C(=O)NH—CH(CH₃) C₆H₅ | NH | 4.654 | 563.00 |
| 1-81 | H | 5-chloro-pyridine-2-yl | NH | 4.425 | 529.00 |
| 1-82 | H | 6-chloro-pyridine-2-yl | NH | 4.274 | 528.95 |
| 1-83 | H | C(=O)NH—CH(CH₃)CH₂SCH₃ | NH | 4.521 | 547.00 |
| 1-84 | H | C(=O)NH—C(CH₃)₂CH₂SCH₃ | NH | 4.705 | 561.00 |
| 1-85 | H | C(=O)NH—CH(CH₃)CF₃ | NH | 4.539 | 555.00 |
| 1-86 | H | C(=O)NH—CH(CH₃) pyridine-3-yl | NH | 3.623 | 564.10 |
| 1-87 | H | C(=O)NH—C(CH₃)₂CH₂ S(=O)₂CH₃ | NH | 4.278 | 593.00 |
| 1-88 | H | C(=O)NH—C(CH₃)₂CH₂ S(=O)CH₃ | NH | 4.059 | 577.00 |
| 1-89 | H | C(=O)NH—CH(CH₃)CH₂S(=O)CH₃ | NH | 3.923 | 563.00 |
| 1-90 | H | C(=O)NH—CH(CH₃)CH₂ S(=O)₂CH₃ | NH | 4.051 | 578.90 |
| 1-91 | H | 4-CF₃-thiazole-2-yl | NH | 4.908 | 566.90 |
| 1-92 | H | 6-CF₃-pyridine-2-yl | NH | 4.300 | 561.05 |
| 1-93 | H | 4-C₆H₅-thiazole-2-yl | NH | 4.940 | 574.90 |
| 1-94 | H | thiazole-2-yl | NH | 4.049 | 498.90 |
| 1-95 | H | 4,5-(CH₃)₂-thiazole-2-yl | NH | 4.280 | 527.05 |

C.2 Compound Examples 2

Compound example 2-1 to 2-19 corresponds to compound formula C.2:

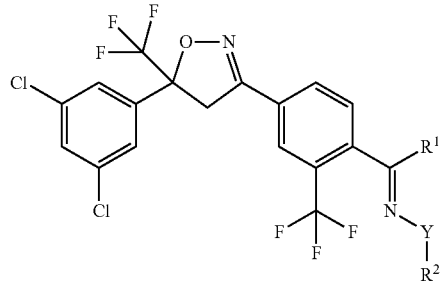

(formula C.2)

wherein R¹, R² and Y of each synthesized compound is defined in one row of table C.2 below.

TABLE C.2

| Compound Ex. | R¹ | R² | Y | $R_t$ (min) | [M + H] |
|---|---|---|---|---|---|
| 2-1 | H | C(=O)NH—CH₂CF₃ | NH | 4.612 | 594.95 |
| 2-2 | H | C(=O)NH—CH₃ | NH | 4.319 | 527.00 |
| 2-3 | H | C(=O)NH—CH₂CH₃ | NH | 4.446 | 541.00 |
| 2-4 | H | C(=O)NH-cyclopropyl | NH | 4.441 | 553.00 |
| 2-5 | H | C(=O)NH—CH₂cyclopropyl | NH | 4.569 | 567.00 |
| 2-6 | H | C(=O)NH—CH₂CH₂CF₃ | NH | 4.560 | 609.00 |
| 2-7 | H | C(=O)NH—CH₂-tetrahydro-furan-2-yl | NH | 4.518 | 597.10 |
| 2-8 | H | C(=O)NH—CH₂CH₂CH₂OCH₃ | NH | 4.438 | 585.00 |
| 2-9 | H | C(=O)NH—CH₂CH₂OCH₃ | NH | 4.428 | 571.05 |
| 2-10 | H | C(=O)NH—CH₂CH₂SCH₃ | NH | 4.507 | 587.00 |
| 2-11 | H | C(=O)NH—CH(CH₃)₂ | NH | 4.570 | 555.00 |
| 2-12 | H | C(=O)NH₂ | NH | 4.227 | 512.95 |
| 2-13 | H | C(=O)NH—CH₂CH(CH₃)₂ | NH | 4.669 | 569.00 |
| 2-14 | H | C(=O)NH—CH₂CHF₂ | NH | 4.513 | 576.95 |
| 2-15 | H | C(=O)NH—CH₂CH₂CH₃ | NH | 4.637 | 555.00 |
| 2-16 | H | C(=O)NH—CH₂C(=O)NH—CH₂CF₃ | NH | 4.301 | 652.00 |
| 2-17 | H | C(=O)NH—CH₂-pyridine-2-yl | NH | 3.840 | 604.10 |
| 2-18 | H | C(=O)NH—CH₂-2-chloropyridine-4-yl | NH | 4.481 | 640.00 |
| 2-19 | H | C(=O)NH—CH₂-pyrimidine-4-yl | NH | 4.255 | 605.00 |

C.3 Compound Examples 3

Compound example 3-1 to 3-5 corresponds to compound formula C.3:

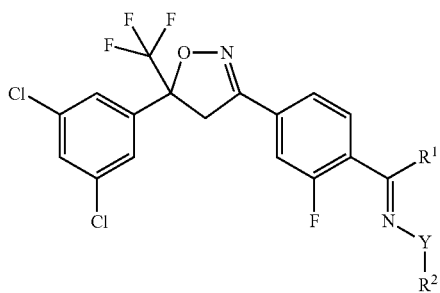

(formula C.3)

wherein $R^1$, $R^2$ and Y of each synthesized compound is defined in one row of table C.3 below.

TABLE C.3

| Compound Ex. | $R^1$ | $R^2$ | Y | $R_t$ (min) | [M + H] |
|---|---|---|---|---|---|
| 3-1 | H | C(=O)NH—CH$_3$ | NH | 4.174 | 476.95 |
| 3-2 | H | C(=O)NH—CH$_2$CH$_3$ | NH | 4.322 | 491.05 |
| 3-3 | H | C(=O)NH—CH$_2$CF$_3$ | NH | 4.417 | 544.95 |
| 3-4 | H | C(=O)NH-cyclopropyl | NH | 3.724* | 503.00 |
| 3-5 | H | C(=O)NH—CH$_2$cyclopropyl | NH | 3.832 | 517.00 |

*this chromatogram was measured using the long method with a total run-time of 6 minutes.

C.4 Compound Examples 4

Compound examples 4-1 to 4-55 correspond to compound formula C.4:

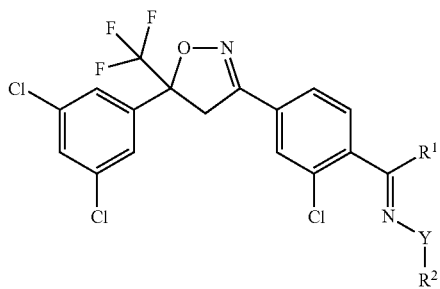

(formula C.4)

wherein $R^1$, $R^2$ and Y of each synthesized compound is defined in one row of table C.4 below.

TABLE C.4

| Compound Ex. | $R^1$ | $R^2$ | Y | $R_t$ (min) | [M + H] |
|---|---|---|---|---|---|
| 4-1 | H | C(=O)NH—CH$_2$CF$_3$ | NH | 4.167 | 560.95 |
| 4-2 | H | C(=O)—NH-cyclopropyl | NH | 4.449 | 519.00 |
| 4-3 | H | C(=O)—NH—CH$_2$-cyclopropyl | NH | 4.584 | 533.00 |
| 4-4 | H | C(=O)NH—CH$_3$ | NH | 4.301 | 493.00 |
| 4-5 | H | C(=O)NH—CH$_2$CH$_3$ | NH | 4.435 | 507.00 |
| 4-6 | H | C(=O)NH—CH$_2$CH$_2$CH(CH$_3$)$_2$ | NH | 4.834 | 549.10 |
| 4-7 | H | C(=O)NH—CH$_2$CH(CH$_3$)$_2$ | NH | 4.703 | 535.10 |
| 4-8 | H | C(=O)NH—CH$_2$CH$_2$-thiophene-2-yl | NH | 4.718 | 589.10 |
| 4-9 | H | C(=O)-thiomorpholine-4-yl | NH | 4.366 | 565.00 |
| 4-10 | H | C(=O)NH—CH$_2$CH$_2$-pyridine-2-yl | NH | 3.790 | 584.00 |
| 4-11 | H | C(=O)NH—CH$_2$-tetrahydrofuran-2-yl | NH | 4.449 | 563.05 |
| 4-12 | H | C(=O)NH-3-thiolyl-1,1-dioxide | NH | 4.126 | 596.90 |
| 4-13 | H | C(=O)NH—CH$_2$CH$_2$CH$_2$-1-imidazolyl | NH | 3.770 | 587.05 |
| 4-14 | H | C(=O)NH—CH$_2$-furan-2-yl | NH | 4.511 | 559.00 |
| 4-15 | H | C(=O)NH-cyclopentyl | NH | 4.756 | 547.00 |
| 4-16 | H | C(=O)NH—CH$_2$C(=O)NH-cyclopropyl | NH | 4.105 | 576.10 |
| 4-17 | H | C(=O)NH—CH$_2$CH$_2$CH$_3$ | NH | 4.571 | 522.95 |
| 4-18 | H | C(=O)NH—CH$_2$CH$_2$CF$_3$ | NH | 4.576 | 574.95 |
| 4-19 | H | C(=O)NH—CH$_2$CHF$_2$ | NH | 4.422 | 542.95 |
| 4-20 | H | C(=O)NH—CH$_2$CH$_2$OCH$_3$ | NH | 4.396 | 537.00 |
| 4-21 | H | C(=O)NH—CH$_2$CH$_2$SCH$_3$ | NH | 4.596 | 555.00 |
| 4-22 | H | C(=O)NH—CH$_2$CH$_2$SCF$_3$ | NH | 4.802 | 608.90 |
| 4-23 | H | C(=O)NH—CH$_2$CH=CCl$_2$ | NH | 4.747 | 588.90 |
| 4-24 | H | C(=O)NH-2-trifluoromethyl-thiazole-4-yl | NH | 4.967 | 632.00 |
| 4-25 | H | C(=O)NH—CH$_2$-2-chloropyrimidine-4-yl | NH | 4.528 | 606.00 |
| 4-26 | H | C(=O)NH$_2$ | NH | 4.177 | 480.90 |
| 4-27 | H | C(=S)NH—CH$_2$CH$_3$ | NH | 4.779 | 523.00 |
| 4-28 | H | C(=S)NH—CH$_2$CF$_3$ | NH | 4.820 | 578.90 |
| 4-29 | H | C(=S)NH—CH$_3$ | NH | 4.607 | 510.90 |
| 4-30 | H | 4-CH$_3$-thiazole-2-yl | NH | 4.200 | 534.95 |
| 4-31 | H | C(=O)NH—CH$_2$C$_6$H$_5$ | NH | 4.560 | 570.90 |
| 4-32 | H | C(=O)NH—CH$_2$-pyridine-3-yl | NH | 3.659 | 570.00 |
| 4-33 | H | C(=O)NH—CH(CH$_3$)CH$_2$SCH$_3$ | NH | 4.574 | 569.00 |
| 4-34 | H | C(=O)NH—CH(CH$_3$)CH$_2$OCH$_3$ | NH | 4.469 | 551.00 |
| 4-35 | H | C(=O)NH—CH$_2$CH$_2$OC$_6$H$_5$ | NH | 4.720 | 599.00 |
| 4-36 | H | C(=O)NH—CH(CH$_3$) C$_6$H$_5$ | NH | 4.777 | 585.00 |
| 4-37 | H | C(=S)NH$_2$ | NH | 4.167 | 496.74 |
| 4-38 | H | C(=O)NH—CH(CH$_3$)CF$_3$ | NH | 4.509 | 574.90 |
| 4-39 | H | C(=O)NH—CH(CH$_3$)cyclopropyl | NH | 4.576 | 546.90 |
| 4-40 | H | C(=O)NH—CH$_2$CH$_2$CF=CF$_2$ | NH | 4.493 | 586.90 |
| 4-41 | H | C(=O)NH—C(CH$_3$)$_2$CH$_2$SCH$_3$ | NH | 4.690 | 582.90 |
| 4-42 | H | C(=O)NH—CH(CH$_3$)CH$_2$OC$_6$H$_5$ | NH | 4.822 | 615.00 |
| 4-43 | H | C(=O)NH-1-(C$_6$H$_5$)cyclopropyl-1-yl | NH | 4.737 | 576.00 |
| 4-44 | H | pyridine-2-yl | NH | 3.821 | 515.00 |
| 4-45 | H | 6-chloro-pyridine-2-yl | NH | 4.919 | 548.90 |
| 4-46 | H | 5-chloro-pyridine-2-yl | NH | 4.689 | 548.95 |
| 4-47 | H | C(=O)NH—CH(CH$_3$) pyridine-3-yl | NH | 3.698 | 586.00 |
| 4-48 | H | C(=O)NH—CH(CH$_3$)CH$_2$S(=O)CH$_3$ | NH | 3.990 | 584.90 |
| 4-49 | H | C(=O)NH—CH(CH$_3$)CH$_2$S(=O)$_2$CH$_3$ | NH | 4.170 | 601.00 |
| 4-50 | H | 4,5-(CH$_3$)$_2$-thiazole-2-yl | NH | 4.342 | 548.95 |
| 4-51 | H | thiazole-2-yl | NH | 4.339 | 520.95 |
| 4-52 | H | 6-CF$_3$-pyridine-2-yl | NH | 4.392 | 580.90 |
| 4-53 | H | 4-CF$_3$-thiazole-2-yl | NH | 4.958 | 586.90 |
| 4-54 | H | C(=O)NH—C(CH$_3$)$_2$CH$_2$S(=O)$_2$CH$_3$ | NH | 4.361 | 615.00 |
| 4-55 | H | C(=O)NH—C(CH$_3$)$_2$CH$_2$S(=O)CH$_3$ | NH | 4.164 | 599.00 |

C.5 Compound Examples 5

Compound examples 5-1 to 5-13 correspond to compound formula C.5:

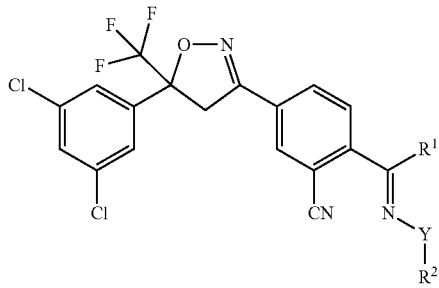

(formula C.5)

wherein R¹, R² and Y of each synthesized compound is defined in one row of table C.5 below.

TABLE C.5

| Compound Ex. | R¹ | R² | Y | $R_t$ (min) | [M + H] |
|---|---|---|---|---|---|
| 5-1 | H | C(=O)NH—CH₂CF₃ | NH | 4.394 | 552.00 |
| 5-2 | H | C(=O)NH—CH₃ | NH | 4.128 | 484.00 |
| 5-3 | H | C(=O)NH—CH₂CH₃ | NH | 4.288 | 498.05 |
| 5-4 | H | C(=O)NH-cyclopropyl | NH | 4.310 | 510.05 |
| 5-5 | H | C(=O)NH—CH₂-cyclopropyl | NH | 4.447 | 524.05 |
| 5-6 | H | C(=O)NH₂ | NH | 3.953 | 469.95 |
| 5-7 | H | C(=O)NH—CH₂CH₂CF₃ | NH | 4.424 | 566.10 |
| 5-8 | H | C(=O)NH—CH₂CHF₂ | NH | 4.269 | 534.05 |
| 5-9 | H | C(=O)NH—CH(CH₃)₂ | NH | 4.439 | 512.05 |
| 5-10 | H | C(=O)NH—CH₂CH(CH₃)₂ | NH | 4.566 | 526.05 |
| 5-11 | H | C(=O)NH—CH₂-tetrahydro-furan-2-yl | NH | 4.257 | 554.05 |
| 5-12 | H | C(=O)NH—CH₂CH₂CH₂OCH₃ | NH | 4.261 | 542.05 |
| 5-13 | H | C(=O)NH—CH₂CH₂OCH₃ | NH | 4.166 | 528.05 |

C.6 Compound Examples 6

Compound examples 6-1 to 6-7 correspond to compounds of formula C.6:

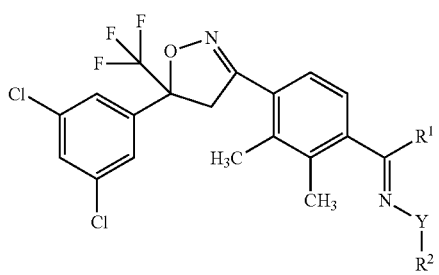

(C.6)

wherein R¹, R² and Y of each synthesized compound is defined in one row of table C.6 below.

TABLE C.6

| Compound Ex. | R¹ | R² | Y | $R_t$ (min) | [M + H] |
|---|---|---|---|---|---|
| 6-1 | H | C(=S)NH—CH₂CF₃ | NH | 4.571 | 570.90 |
| 6-2 | H | C(=O)NH—CH₂CH₃ | NH | 4.283 | 501.00 |
| 6-3 | H | C(=O)NH—CH₃ | NH | 4.231 | 487.05 |
| 6-4 | H | C(=S)NH—CH₃ | NH | 4.485 | 503.00 |

TABLE C.6-continued

| Compound Ex. | R¹ | R² | Y | $R_t$ (min) | [M + H] |
|---|---|---|---|---|---|
| 6-5 | H | C(=S)NH—CH₂CH₃ | NH | 4.609 | 517.05 |
| 6-6 | H | C(=O)NH-cyclopropyl | NH | 4.383 | 513.05 |
| 6-7 | H | C(=O)NH—CH₂CF₃ | NH | 4.364 | 555.00 |

C.7 Compound Examples 7

Compound examples 7-1 to 7-8 correspond to compounds of formula C.7:

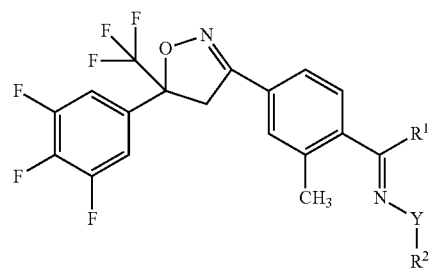

(C.7)

wherein R¹, R² and Y of each synthesized compound is defined in one row of table C.7 below.

TABLE C.7

| Compound Ex. | R¹ | R² | Y | $R_t$ (min) | [M + H] |
|---|---|---|---|---|---|
| 7-1 | H | C(=O)NH—CH₂CF₃ | NH | 4.025 | 527.00 |
| 7-2 | H | C(=O)NH—CH₂-cyclopropyl | NH | 4.078 | 499.00 |
| 7-3 | H | C(=O)NH-cyclopropyl | NH | 3.939 | 485.00 |
| 7-4 | H | C(=O)NH—CH₂CH₃ | NH | 3.920 | 473.00 |
| 7-5 | H | C(=O)NH—CH₃ | NH | 3.861 | 459.05 |
| 7-6 | H | C(=S)NH—CH₃ | NH | 4.110 | 475.05 |
| 7-7 | H | C(=S)NH—CH₂CH₃ | NH | 4.263 | 489.05 |
| 7-8 | H | C(=S)NH—CH₂CF₃ | NH | 4.234 | 543.00 |

C.8 Compound Examples 8

Compound examples 8-1 to 8-8 correspond to compounds of formula C.8:

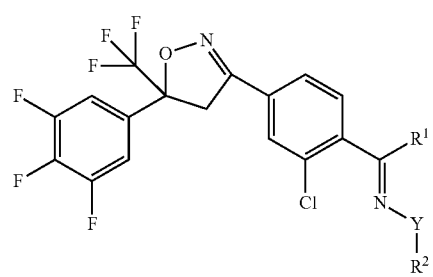

(C.8)

wherein R¹, R² and Y of each synthesized compound is defined in one row of table C.8 below.

TABLE C.8

| Compound Ex. | $R^1$ | $R^2$ | Y | $R_t$ (min) | [M + H] |
|---|---|---|---|---|---|
| 8-1 | H | C(=O)NH—CH$_2$CF$_3$ | NH | 4.271 | 546.95 |
| 8-2 | H | C(=O)NH—CH$_2$-cyclopropyl | NH | 4.205 | 519.00 |
| 8-3 | H | C(=O)NH-cyclopropyl | NH | 4.160 | 505.10 |
| 8-4 | H | C(=O)NH—CH$_2$CH$_3$ | NH | 4.149 | 493.10 |
| 8-5 | H | C(=O)NH—CH$_3$ | NH | 4.002 | 479.10 |
| 8-6 | H | C(=S)NH—CH$_3$ | NH | 4.253 | 495.00 |
| 8-7 | H | C(=S)NH—CH$_2$CH$_3$ | NH | 4.399 | 509.00 |
| 8-8 | H | C(=S)NH—CH$_2$CF$_3$ | NH | 4.339 | 562.90 |

C.9 Compound Examples 9

Compound examples 9-1 to 9-15 correspond to compounds of formula C.9:

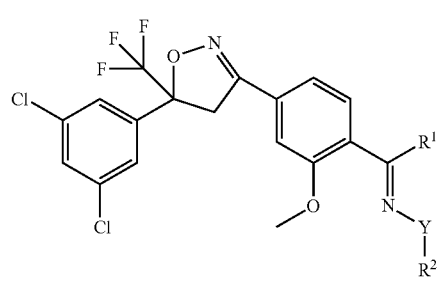

(C.9)

wherein $R^1$, $R^2$ and Y of each synthesized compound is defined in one row of table C.9 below.

TABLE C.9

| Compound Ex. | $R^1$ | $R^2$ | Y | $R_t$ (min) | [M + H] |
|---|---|---|---|---|---|
| 9-1 | H | C(=O)NH—CH$_2$CF$_3$ | NH | 4.389 | 556.95 |
| 9-2 | H | C(=O)NH—CH$_2$CH$_3$ | NH | 4.291 | 503.05 |
| 9-3 | H | C(=O)NH—CH$_3$ | NH | 4.153 | 489.05 |
| 9-4 | H | C(=O)NH—CH$_2$C$_6$H$_5$ | NH | 4.535 | 565.00 |
| 9-5 | H | C(=O)NH—CH$_2$-pyridine-3-yl | NH | 3.543 | 566.00 |
| 9-6 | H | C(=O)NH—CH(CH$_3$)CH$_2$SCH$_3$ | NH | 4.400 | 562.90 |
| 9-7 | H | C(=O)NH—CH$_2$OC$_6$H$_5$ | NH | 4.506 | 595.00 |
| 9-8 | H | C(=O)NH—CH(CH$_3$)CH$_2$OCH$_3$ | NH | 4.245 | 547.00 |
| 9-9 | H | C(=O)NH—CH(CH$_3$) C$_6$H$_5$ | NH | 4.552 | 579.00 |
| 9-10 | H | C(=O)NH—CH(CH$_3$)CF$_3$ | NH | 4.519 | 571.00 |
| 9-11 | H | C(=O)NH—CH(CH$_3$)cyclopropyl | NH | 4.566 | 543.00 |
| 9-12 | H | C(=O)NH—CH$_2$CH$_2$CF=CF$_2$ | NH | 4.490 | 583.00 |
| 9-13 | H | C(=O)NH—CH(CH$_3$)CH$_2$OC$_6$H$_5$ | NH | 4.715 | 609.00 |
| 9-14 | H | C(=O)NH-1-(C$_6$H$_5$)cyclopropyl 1-yl | NH | 4.635 | 591.00 |
| 9-15 | H | C(=O)NH—C(CH$_3$)$_2$CH$_2$SCH$_3$ | NH | 4.946 | 577.00 |

C.10 Compound Examples 10

Compound examples 10-1 to 10-6 correspond to compounds of formula C.10:

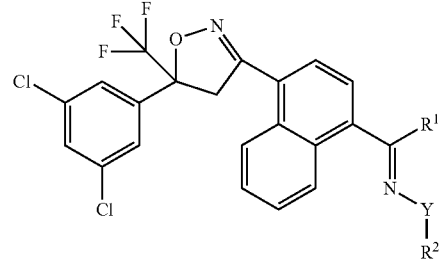

(C.10)

wherein $R^1$, $R^2$ and Y of each synthesized compound is defined in one row of table C.10 below.

TABLE C.10

| Compound Ex. | $R^1$ | $R^2$ | Y | $R_t$ (min) | [M + H] |
|---|---|---|---|---|---|
| 10-1 | H | C(=O)NH—CH$_2$CF$_3$ | NH | 4.598 | 577.00 |
| 10-2 | H | C(=O)NH—CH$_3$ | NH | 4.291 | 508.90 |
| 10-3 | H | C(=O)NH—CH$_2$CH$_3$ | NH | 4.527 | 523.00 |
| 10-4 | H | C(=O)NH-cyclopropyl | NH | 4.527 | 535.10 |
| 10-5 | H | C(=O)NH—CH$_2$cyclopropyl | NH | 4.675 | 549.10 |
| 10-6 | H | C(=S)NH—CH$_3$ | NH | 4.596 | 524.95 |

C.11 Compound Examples 11

Compound examples 11-1 to 11-3 correspond to compounds of formula C.11:

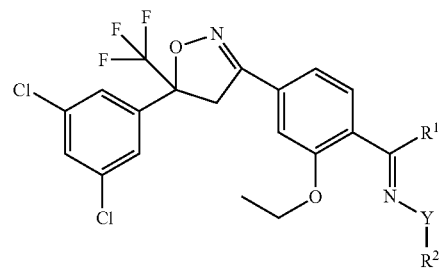

(C.11)

wherein $R^1$, $R^2$ and Y of each synthesized compound is defined in one row of table C.11 below.

TABLE C.11

| Compound Ex. | $R^1$ | $R^2$ | Y | $R_t$ (min) | [M + H] |
|---|---|---|---|---|---|
| 11-1 | H | C(=O)NH—CH$_2$CF$_3$ | NH | 4.556 | 571.10 |
| 11-2 | H | C(=O)NH—CH$_3$ | NH | 4.322 | 503.10 |
| 11-3 | H | C(=O)NH—CH$_2$CH$_3$ | NH | 4.464 | 517.10 |

B. Biological Examples

Evaluation of Pesticidal Activity

The activity of the compounds of formula III of the present invention could be demonstrated and evaluated by the following biological test.

B.1 Tobacco Budworm (*Heliothis virescens*) I

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 μl, using a custom built micro atomizer, at two replications. After application, microtiter plates are incubated at about 28±1° C. and about 80±5% relative humidity for 5 days. Egg and larval mortality is then visually assessed.

In this test, the compounds 1-1, 1-2, 1-3, 1-4, 1-5, 1-6, 1-7, 1-8, 1-9, 1-10, 1-11, 1-12, 1-13, 1-14, 1-15, 1-16, 1-17, 1-18, 1-19, 1-20, 1-21, 1-22, 1-23, 1-26, 1-27, 1-28, 1-29, 1-30, 1-31, 1-32, 1-33, 1-34, 1-35, 1-36, 1-39, 1-40, 1-41, 1-42, 1-43, 1-44, 1-45, 1-47, 1-48, 1-49, 1-51, 1-52, 1-53, 1-54, 1-55, 1-56, 1-57, 1-58, 1-59, 1-60, 1-62, 1-63, 1-64, 1-65, 1-66, 1-67, 1-68, 1-69, 1-70, 1-71, 1-72, 1-73, 1-74, 1-75, 1-76, 1-77, 1-79, 1-80, 1-81, 1-82, 1-83, 1-84, 1-85, 1-86, 1-87, 1-88, 1-89, 1-90, 1-91, 1-92, 1-93, 1-94, 1-95, 2-1, 2-2, 2-3, 2-4, 2-5, 2-6, 2-7, 2-8, 2-9, 2-10, 2-11, 2-12, 2-13, 2-14, 2-15, 2-16, 2-17, 2-18, 2-19, 3-1, 3-2, 3-3, 4-1, 4-2, 4-3, 4-4, 4-5, 4-6, 4-7, 4-8, 4-9, 4-10, 4-11, 4-12, 4-13, 4-14, 4-15, 4-16, 4-17, 4-18, 4-19, 4-20, 4-21, 4-22, 4-23, 4-24, 4-25, 4-26, 4-27, 4-28, 4-29, 4-30, 4-31, 4-32, 4-33, 4-34, 4-35, 4-36, 4-37, 4-38, 4-39, 4-40, 4-41, 4-42, 4-43, 4-44, 4-45, 4-46, 4-47, 4-48, 4-49, 4-50, 4-51, 4-52, 4-53, 4-54, 4-55, 5-1, 5-2, 5-3, 5-4, 5-5, 5-6, 5-9, 5-10, 5-11, 5-12, 5-13, 5-14, 6-1, 6-2, 6-3, 6-4, 6-5, 6-6, 6-7, 7-1, 7-2, 7-3, 7-4, 7-5, 7-6, 7-7, 7-8, 8-1, 8-2, 8-3, 8-4, 8-5, 8-6, 8-7, 8-8, 9-1, 9-2, 9-3, 9-4, 9-5, 9-6, 9-7, 9-8, 9-9, 9-10, 9-11, 9-12, 9-13, 9-14, 9-15, 10-1, 10-2, 10-3, 10-4, 10-5, 10-6, 10-6, 11-1, 11-2 and 11-3, at 2500 ppm, respectively showed a mortality of at least 75% in comparison with untreated controls.

We claim:

1. A process for producing a carbonyl compound of formula I (I)

wherein $A^1$, $A^2$, $A^3$ and $A^4$ are C or substituted C;

$B^1$, $B^2$ and $B^3$ are C or substituted C;

X is selected from the group consisting of $C_1$-$C_4$-alkyl and fluorinated $C_1$-$C_4$ alkyl;

each $R^4$ is independently selected from the group consisting of fluorine; chlorine; cyano; $C_1$-$C_6$-alkyl; fluorinated $C_1$-$C_6$-alkyl; $C_1$-$C_6$-alkoxy and fluorinated $C_1$-$C_6$-alkoxy;

or two radicals $R^4$ bound on adjacent carbon atoms may be together a group selected from the group consisting of $—CH_2CH_2CH_2CH_2—$, $—CH{=}CH—CH{=}CH—$, and $—CH_2CH_2CH_2—$, thus forming, together with the carbon atoms to which they are bound, a 5- or 6-membered ring;

each $R^5$ is independently selected from the group consisting of fluorine, chlorine, and fluorinated $C_1$-$C_6$-alkyl;

p is 0, 1, 2, 3 or 4; and q is 0, 1 2, 3, 4 or 5;

comprising following step:

reacting a compound of formula II (II)

wherein

Z is selected from the group consisting of Br, I, and $—OSO_2—R^{z1}$, where $R^{z1}$ is $C_1$-$C_4$-alkyl, $C_1$-$C_4$-haloalkyl or phenyl which may be substituted by 1, 2 or 3 radicals selected from the group consisting of $C_1$-$C_4$-alkyl, $C_1$-$C_4$-haloalkyl $C_1$-$C_4$-alkoxy and $C_1$-$C_4$-haloalkoxy;

with carbon monoxide and hydrogen in the presence of a transition metal complex catalyst.

2. A process for producing imine compounds of the formula III (III)

wherein

Y is O, $N—R^3$, $S(O)_n$ or a chemical bond;

$R^1$ is selected from the group consisting of hydrogen; $C_1$-$C_6$-alkyl and fluorinated $C_1$-$C_6$-alkyl;

$R^2$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$;

$—N(R^8)R^9$; $—N(R^8)C({=}O)R^6$; $—Si(R^{14})_2R^{13}$; $—OR^7$; $—SR^7$; $—S(O)_mR^7$; $—S(O)_nN(R^8)R^9$; $—C({=}O)R^6$; $—C({=}O)OR^7$; $—C({=}O)N(R^8)R^9$; $—C({=}S)R^6$; $—C({=}S)OR^7$, $—C({=}S)N(R^8)R^9$; $—C({=}NR^8)R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^2$ is not $-OR^7$ if Y is O;

$R^3$ is selected from the group consisting of hydrogen; cyano; $C_1$-$C_{10}$-alkyl which may be partially or fully halogenated and/or may be substituted by one or more radicals $R^6$; $C_3$-$C_8$-cycloalkyl which may be partially or fully halogenated and/or may be substituted by one or more radicals $R^6$; $C_2$-$C_{10}$-alkenyl which may be partially or fully halogenated and/or may be substituted by one or more radicals $R^6$; $C_2$-$C_{10}$-alkynyl which may be partially or fully halogenated and/or may be substituted by one or more radicals $R^6$;

$-N(R^8)R^9$; $-Si(R^{14})_2R^{13}$; $-OR^7$; $-SR^7$; $-S(O)_mR^7$; $-S(O)_nN(R^8)R^9$; $-C(=O)R^6$; $-C(=O)OR^7$; $-C(=O)N(R^8)R^9$; $-C(=S)R^6$; $-C(=S)OR^7$; $-C(=S)N(R^8)R^9$;

$-C(=NR^8)R^6$; phenyl which may be substituted by 1, 2, 3, 4 or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

or $R^2$ and $R^3$ together form a group $=CR^{11}R^{12}$; $=S(O)_mR^7$; $=S(O)_mN(R^8)R^9$; $=NR^8$; or $=NOR^7$;

or $R^2$ and $R^3$ together form a $C_2$-$C_7$ alkylene chain, thus forming, together with the nitrogen atom to which they are bound, a 3-, 4-, 5-, 6-, 7- or 8-membered ring, where the alkylene chain may be interrupted by 1 or 2 O, S and/or $NR^{18}$ and/or 1 or 2 of the $CH_2$ groups of the alkylene chain may be replaced by a group $C=O$, $C=S$ and/or $C=NR^{18}$; and/or the alkylene chain may be substituted by one or more radicals selected from the group consisting of halogen, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^6$ is independently selected from the group consisting of cyano, azido, nitro, $-SCN$, $SF_5$, $C_3$-$C_8$-cycloalkyl, $C_3$-$C_8$-halocycloalkyl, $-Si(R^{14})_2R^{13}$, $-OR^7$, $-OSO_2R^7$, $-SR^7$, $-S(O)R^7$, $-S(O)_nN(R^8)R^9$, $-N(R^8)R^9$, $-C(=O)N(R^8)R^9$, $-C(=S)N(R^8)R^9$, $-C(=O)OR^7$, $-C(=O)R^{19}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO, as ring members, where the heterocyclic ring may be substituted by one or more radicals $R^{10}$;

and, in case $R^6$ is bound to a cycloalkyl group or to a heterocyclic ring formed by $R^1$ and $R^2$ together with the atoms to which they are bound, $R^6$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl and benzyl which may be substituted by 1, 2, 3, 4 or 5 radicals $R^{10}$; and in groups $-C(=O)R^6$, $-C(=S)R^6$, $-C(=NR^8)R^6$ and $-N(R^8)C(=O)R^6$, $R^6$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl, $C_1$-$C_6$-haloalkynyl and benzyl which may be substituted by 1, 2, 3, 4 or 5 radicals $R^{10}$;

or two geminally bound radicals $R^6$ together form a group selected from the group consisting of $=CR^{11}R^{12}$, $=S(O)_mR^7$, $=S(O)_mN(R^8)R^9$, $=N-R^8$, $=NOR^7$ and $=NNR^8$;

or two radicals $R^6$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^7$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, $-Si(R^{14})_2R^{13}$, $-SR^8$, $-S(O)N(R^8)R^9$, $-N(R^8)R^9$, $-N=CR^{15}R^{16}$, $-C(=O)R^{17}$, $-C(=O)N(R)R^9$, $-C(=S)N(R^8)R^9$, $-C(=O)OR^{17}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

with the proviso that $R^7$ is not $C_1$-$C_6$-alkoxy or $C_1$-$C_6$-haloalkoxy if it is bound to an oxygen atom;

each $R^8$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_1$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, $-S(O)_mR^{20}$, $-S(O)_nN(R^{21})R^{22}$, phenyl which may be substituted by 1, 2, 3, 4 or 5 radicals $R^{10}$, benzyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals $R^{10}$;

each $R^9$ is independently selected from the group consisting of hydrogen, cyano, $C_1$-$C_6$-alkyl which may be partially or fully halogenated and/or may be substituted by one or more radicals $R^{19}$, $C_1$-$C_6$-alkoxy, $C_1$-$C_6$-haloalkoxy, $C_1$-$C_6$-alkylthio, $C_1$-$C_6$-haloalkylthio, where the alkyl moiety in the four last-mentioned radicals may be substituted by one or more radicals $R^{19}$, $C_3$-$C_8$-cycloalkyl which may be partially or fully halogenated and/or may be substituted by one or more radicals $R^{19}$, $C_3$-$C_8$-cycloalkyl-$C_1$-$C_4$-alkyl where the cycloalkyl moiety may be partially or fully halogenated and/or may be substituted by one or more radicals $R^{19}$, $C_2$-$C_6$-alkenyl which may be partially or fully halogenated and/or may be substituted by one or more radicals $R^{19}$, $C_2$-$C_6$-alkynyl which may be partially or fully halogenated and/or may be substituted by one or more radicals $R^{19}$, —S(O)$_m$R$^{20}$, —S(O)$_n$N(R$^{21}$)R$^{22}$, phenyl which may be substituted by 1, 2, 3, 4 or 5 radicals $R^{10}$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^{10}$;

or $R^8$ and $R^9$ together form a group =CR$^{11}$R$^{12}$;

or $R^8$ and $R^9$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and SO$_2$, as ring members, where the heterocyclic ring may be substituted by one or more radicals $R^{1'}$;

each $R^{10}$ is independently selected from the group consisting of fluorine, chlorine, cyano, nitro, —SCN, SF$_5$, $C_1$-$C_{10}$-alkyl which may be partially or fully halogenated and/or may be substituted by one or more radicals $R^{19}$, $C_3$-$C_8$-cycloalkyl which may be partially or fully halogenated and/or may be substituted by one or more radicals $R^{19}$, $C_2$-$C_{10}$-alkenyl which may be partially or fully halogenated and/or may be substituted by one or more radicals $R^{19}$, $C_2$-$C_{10}$-alkynyl which may be partially or fully halogenated and/or may be substituted by one or more radicals $R^{19}$, —OR$^{20}$, —SR$^{20}$, —S(O)$_m$R$^{20}$, —S(O)$_n$N(R$^{21}$)R$^{22}$, C(=O)R$^9$, —C(=O)OR$^{20}$, —C(=NR$^{21}$)R$^{22}$, —C(=O)N(R$^{21}$)R$^{22}$, —C(=S)N(R$^{21}$)R$^{22}$, phenyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy; and a 3-, 4-, 5-, 6- or 7-membered saturated or unsaturated heterocyclic ring containing 1, 2 or 3 heteroatoms or heteroatom groups selected from the group consisting of N, O, S, NO, SO and SO$_2$, as ring members, which may be substituted by one or more radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

or two radicals $R^{10}$ bound on adjacent atoms together form a group selected from the group consisting of —CH$_2$CH$_2$CH$_2$CH$_2$—, —CH=CH—CH=CH—, —N=CH—CH=CH—, —CH=N—CH=CH—, —N=CH—N=CH—, —OCH$_2$CH$_2$—, —OCH=CHCH$_2$—, —CH$_2$OCH$_2$CH$_2$—, —OCH$_2$CH$_2$O—, —OCH$_2$OCH$_2$—, —CH$_2$CH$_2$CH$_2$—, —CH=CH$_2$CH$_2$—, —CH$_2$CH$_2$O—, —CH=CHO—, —CH$_2$OCH$_2$—, —CH$_2$C(=O)O—, —C(=O)OCH$_2$—, —O(CH$_2$)O—, —SCH$_2$CH$_2$CH$_2$—, —SCH=CHCH$_2$—, —CH$_2$SCH$_2$CH$_2$—, —SCH$_2$CH$_2$S—, —SCH$_2$SCH$_2$—, —CH$_2$CH$_2$S—, —CH=CHS—, —CH$_2$SCH$_2$—, —CH$_2$C(=S)S—, —C(=S)SCH$_2$—, —S(CH$_2$)S—, —CH$_2$CH$_2$NR$^{21}$—, —CH$_2$CH=N—, —CH=CH—NR$^{21}$—, —OCH=N— and —SCH=N—, thus forming, together with the atoms to which they are bound, a 5- or 6-membered ring, where the hydrogen atoms of the above groups may be replaced by one or more substituents selected from the group consisting of fluorine, chlorine, methyl, halomethyl, hydroxyl, methoxy and halomethoxy or one or more CH$_2$ groups of the above groups may be replaced by a C=O group;

$R^{11}$, $R^{12}$ are, independently of each other and independently of each occurrence, selected from the group consisting of hydrogen, halogen, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy, $C_1$-$C_6$-haloalkoxy, —C(=O)R$^{19}$, —C(=O)OR$^{20}$, —C(=NR$^{21}$R$^{22}$, —C(=O)N(R$^{21}$)R$^{22}$, —C(=S)N(R$^{21}$)R$^{22}$, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

$R^{13}$, $R^{14}$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^{15}$, $R^{16}$ are, independently of each other and independently of each occurrence, selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl which may be substituted by 1, 2, 3, 4, or 5 radicals $R^{10}$; and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, which may be substituted by one or more radicals $R^{10}$;

each $R^{17}$ is independently selected from the group consisting of $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_8$-cycloalkyl, $C_3$-$C_8$-halocycloalkyl, $C_1$-$C_6$-alkoxy-$C_1$-$C_6$-alkyl, $C_1$-$C_6$-haloalkoxy-$C_1$-$C_6$-alkyl, phenyl and benzyl;

each $R^{18}$ is independently defined like $R^3$;

each $R^{19}$ is independently selected from the group consisting of cyano, azido, nitro, —SCN, SF$_5$, $C_3$-$C_8$-cycloalkyl, $C_3$-$C_8$-halocycloalkyl, —Si(R$^{14}$)$_2$R$^{13}$, —OR$^{20}$, —OSO$_2$R$^{20}$, —SR$^{20}$, —S(O), R$^{20}$, —S(O)$_n$N(R$^{21}$)R$^{22}$, —N(R$^{21}$)R$^{22}$, —C(=O)N(R$^{21}$)R$^{22}$, —C(=S)N(R$^{21}$)R$^{22}$, —C(=O)OR$^{20}$, —C(=O)R$^{20}$, phenyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

and, in case $R^{19}$ is bound to a cycloalkyl group, $R^{19}$ may additionally be selected from the group consisting of $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_2$-$C_6$-alkynyl and $C_2$-$C_6$-haloalkynyl;

and in groups —C(=O)$R^{19}$, $R^{19}$ may additionally be selected from the group consisting of hydrogen, halogen, $C_1$-$C_6$-alkyl, $C_1$-$C_6$-haloalkyl, $C_1$-$C_6$-alkoxy-$C_1$-$C_6$-alkyl, $C_2$-$C_6$-alkenyl, $C_2$-$C_6$-haloalkenyl, $C_1$-$C_6$-alkynyl, and $C_2$-$C_6$-haloalkynyl;

or two geminally bound radicals $R^{19}$ together form a group selected from the group consisting of =$CR^{11}R^{12}$, =$S(O)_mR^{20}$, =$S(O)_mN(R^{21})R^{22}$, =$NR^{21}$, =$NOR^{20}$ and =$NNR^{21}$;

or two radicals $R^{19}$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and $SO_2$, as ring members;

each $R^{20}$ is independently selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_3$-$C_8$-cycloalkyl, $C_3$-$C_8$-cycloalkyl-$C_1$-$C_4$-alkyl, $C_3$-$C_8$-halocycloalkyl, $C_2$-$C_6$-alkenyl, $C_2$-$C_6$-haloalkenyl, $C_1$-$C_6$-alkynyl, $C_2$-$C_6$-haloalkynyl, —Si($R^{14}$)$_2R^{13}$, $C_1$-$C_6$-alkylaminosulfonyl, amino, $C_1$-$C_6$-alkylamino, di-($C_1$-$C_6$-alkyl)-amino, $C_1$-$C_6$-alkylcarbonyl, $C_1$-$C_6$-haloalkylcarbonyl, aminocarbonyl, $C_1$-$C_6$-alkylaminocarbonyl, di-($C_1$-$C_6$-alkyl)-aminocarbonyl, $C_1$-$C_6$-alkoxycarbonyl, $C_1$-$C_6$-haloalkoxycarbonyl, phenyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

with the proviso that $R^{20}$ is not $C_1$-$C_6$-alkoxy or $C_1$-$C_6$-haloalkoxy if it is bound to an oxygen atom;

$R^{21}$ and $R^{22}$ are independently of each other and independently of each occurrence selected from the group consisting of hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_3$-$C_8$-cycloalkyl-$C_1$-$C_4$-alkyl, $C_2$-$C_6$-alkenyl, $C_2$-$C_6$-haloalkenyl, $C_2$-$C_6$-alkynyl, $C_1$-$C_6$-haloalkynyl, phenyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy, benzyl which may be substituted by 1, 2, 3, 4 or 5 radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and $SO_2$, as ring members, where the heterocyclic ring may be substituted by one or more radicals independently selected from the group consisting of fluorine, chlorine, cyano, nitro, $C_1$-$C_6$-alkyl, $C_1$-$C_6$-haloalkyl, $C_1$-$C_6$-alkoxy and $C_1$-$C_6$-haloalkoxy;

or $R^{21}$ and $R^{22}$, together with the nitrogen atom to which they are bound, may form a 3-, 4-, 5-, 6- or 7-membered saturated, partially unsaturated or aromatic heterocyclic ring which may additionally containing 1 or 2 further heteroatoms or heteroatom groups selected from the group consisting of N, O, S, NO, SO and $SO_2$, as ring members, where the heterocyclic ring may be substituted by one or more radicals selected from f the group consisting of fluorine, chlorine, $C_1$-$C_6$-alkyl, $C_1$-$C_6$-haloalkyl, $C_1$-$C_6$-alkoxy and $C_1$-$C_6$-haloalkoxy;

each m is independently 1 or 2:

each n is independently 0, 1 or 2;

and $A^1$, $A^2$, $A^3$, $A^4$, $B^2$, $B^3$, X, $R^4$, $R^5$, p and q are as defined in claim 1;

comprising following step:

in preparing compound of formula (III) wherein $R^1$ is hydrogen, reacting a compound of formula II

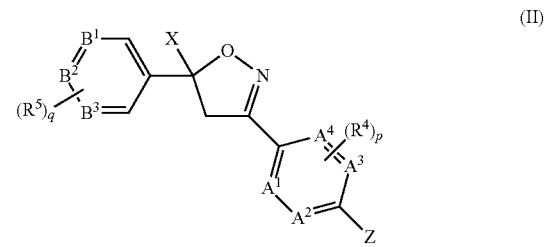

(II)

wherein $A^1$, $A^2$, $A^3$, $A^4$, $B^1$, $B^2$, $B^3$, X, $R^4$, $R^5$, p and q are as defined above and Z is selected from the group consisting of Br, I, and —$OSO_2$—$R^{z1}$, where $R^{z1}$ is $C_1$-$C_4$-alkyl, $C_1$-$C_4$-haloalkyl or phenyl which may be substituted by 1, 2 or 3 radicals selected from the group consisting of $C_1$-$C_4$-alkyl, $C_1$-$C_4$-haloalkyl $C_1$-$C_4$-alkoxy or $C_1$-$C_4$-haloalkoxy;

with carbon monoxide and hydrogen in the presence of a transition metal complex catalyst to produce a carbonyl compound of formula I

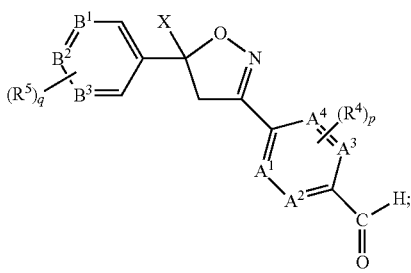

(I)

reacting the compound of formula I with a compound $NH_2$—Y—$R^2$ to obtain the compound of formula (III) wherein $R^1$ is hydrogen; or in preparing compound of formula (III) wherein $R^1$ is not hydrogen, reacting a compound of formula II with a Grignard reagent $R^1$—MgHal, where Hal is Cl, Br or I, or an organolithium compound $R^1$—Li to obtain an alcohol of formula IV

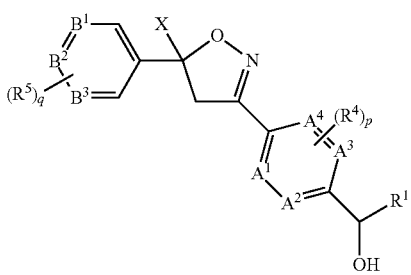

(IV)

oxidizing the alcohol of formula IV to obtain a carbonyl compound V

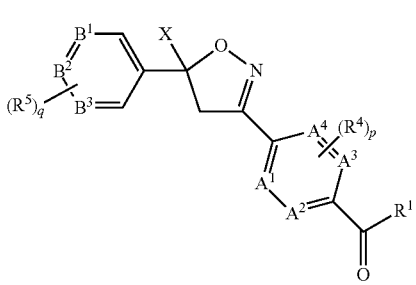

(V)

and reacting the carbonyl compound of formula V with a compound $NH_2$—Y—$R^2$ wherein $R^1$ is not hydrogen.

3. The process as claimed in claim 1, where Z is Br, I or —$OSO_2$—$R^{z1}$, where $R^{z1}$ is selected from the group consisting of $CH_3$, $CF_3$ and 4-methylphenyl.

4. The process as claimed in claim 1, where carbon monoxide and hydrogen are used in a molar ratio of from 20:1 to 1:10.

5. The process as claimed in claim 4, where carbon monoxide and hydrogen are used in a molar ratio of from 2:1 to 1:2.

6. The process as claimed in claim 1, where the catalyst is a group VIII metal complex.

7. The process as claimed in claim 6, where the metal is selected from the group consisting of Pd, Pt, Ni, Rh, Ir and Ru.

8. The process as claimed in claim 1, where the catalyst contains a monodentate and/or bidentate ligand.

9. The process as claimed in claim 1, where the catalyst contains a phosphorus-containing ligand.

10. The process as claimed in claim 9, where the phosphorus-containing ligand is a monodentate ligand selected from the group consisting of phosphorus compounds of formula $PR^aR^bR^c$, where $R^a$, $R^b$ and $R^c$, independently of each other, are selected from the group consisting of $C_3$-$C_{12}$-alkyl, $C_3$-$C_{12}$-alkoxy, where the alkyl moieties in the 2 last-mentioned radicals may carry 1, 2 or 3 substituents $R^d$; $C_3$-$C_{10}$-cycloalkyl, $C_3$-$C_{10}$-cycloalkoxy, heterocycyl, heterocyclyloxy, $C_5$-$C_{18}$-polycyclyl, $C_5$-$C_{18}$-polycyclyloxy, aryl, aryloxy, hetaryl and hetaryloxy, where the cycloalkyl, heterocyclyl, polycyclyl, aryl and hetaryl moieties in the 10 last-mentioned radicals may carry 1, 2, 3 or 4 substituents $R^e$;

or $R^a$ and $R^b$ together with the phosphorus atom to which they are bound form a 5-, 6-, 7- or 8-membered heterocyclic ring which may be additionally fused to one, two or three $C_3$-$C_{10}$-cycloalkyl, heterocyclyl, aryl or hetaryl groups, where the heterocyclic ring and, if present, the fused-on groups may each independently carry one, two, three or four substituents Re;

each $R^d$ is independently selected from the group consisting of $C_3$-$C_{10}$-cycloalkyl, $C_3$-$C_{10}$-cycloalkoxy, heterocyclyl, heterocyclyloxy, aryl, aryloxy, hetaryl, hetaryloxy, $C_1$-$C_6$-alkoxy, OH, SH, COOH, carboxylate, $SO_3H$, sulfonate, $NE^1E^2$, $NE^1E^2E^{3+}X^-$, halogen, nitro, acyl and cyano;

each $R^e$ is independently selected from the group consisting of $C_1$-$C_6$-alkyl, $C_3$-$C_{10}$-cycloalkyl, $C_3$-$C_{10}$-cycloalkoxy, heterocyclyl, heterocyclyloxy, aryl, aryloxy, hetaryl, hetaryloxy, $C_1$-$C_6$-alkoxy, OH, SH, COOH, carboxylate, $SO_3H$, sulfonate, $NE^1E^2$, $NE^1E^2E^{3+}X^-$, halogen, nitro, acyl and cyano;

$E^1$, $E^2$ and $E^3$ are identical or different radicals selected from the group consisting of hydrogen, $C_1$-$C_6$-alkyl, $C_3$-$C_{10}$-cycloalkyl and aryl; and $X^-$ is an anion equivalent.

11. The process as claimed in claim 10, where $R^a$, $R^b$ and $R^c$, independently of each other, are selected from the group consisting of $C_3$-$C_{12}$-alkyl, cyclohexyl, adamantyl, phenyl and phenoxy, where the cyclohexyl, adamantyl and phenyl moiety in the 4 last-mentioned radicals may carry 1, 2 or 3 substituents selected from the group consisting of $C_1$-$C_6$-alkyl and $C_1$-$C_4$-alkoxy.

12. The process as claimed in claim 9, where the phosphorus-containing ligand is a bidentate ligand selected from phosphorus compounds of formula

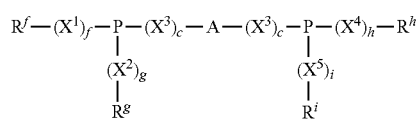

where $X^1$, $X^2$, $X^3$, $X^4$ and $X^5$, independently of each other and independently of each occurrence, are selected from O, S, NR and a group $SiR^kR^l$, where $R^j$, $R^k$ and $R^l$, independently of each other, are selected from the group consisting of hydrogen, $C_1$-$C_4$-alkyl, $C_3$-$C_6$-cycloalkyl, heterocyclyl, aryl and hetaryl;

c, f, g, h and i are independently 0 or 1;

$R^f$, $R^g$, $R^h$ and $R^i$, independently of each other, are selected from the group consisting of $C_3$-$C_{12}$-alkyl which may carry 1, 2 or 3 substituents $R^d$; $C_3$-$C_{10}$-cycloalkyl, heterocyclyl, $C_5$-$C_{18}$-polycyclyl, aryl and hetaryl, where the cycloalkyl, heterocyclyl, polycyclyl, aryl and hetaryl moieties in the 5 last-mentioned radicals may carry 1, 2, 3 or 4 substituents $R^e$;

where $R^d$ and $R^e$ are as defined in claim 10;

or in case $X^1$ and $X^2$ are O or NR and f and g are 1, $R^f$ together with $R^g$ form a $C_2$-$C_5$-alkylene group; and/or in case $X^4$ and $X^5$ are O or $NR^j$ and h and g are 1, $R^h$ together with $R^i$ form a $C_2$-$C_5$-alkylene group; and A is a bridging group.

13. The process as claimed in claim 12, where the bridging group A is selected from the group consisting of divalent aliphatic groups, divalent alicyclic groups, divalent heterocyclic groups, divalent aliphatic-alicyclic groups, divalent aromatic groups, divalent araliphatic groups, divalent heteroaromatic groups, divalent heteroaromatic-aliphatic groups and metallocene groups.

14. The process as claimed in claim 13, where the bridging group A is selected from the group consisting of $C_2$-$C_6$-alkylene, binaphthenediylyl, xanthenediyl and ferrocenediyl, where the cyclic moieties in the 3 last-mentioned radicals may carry 1, 2, 3, 4, 5 or 6 radicals selected from $C_1$-$C_6$-alkyl and $C_1$-$C_4$-alkoxy.

15. The process as claimed in claim 12, where $R^f$, $R^g$, $R^h$ and $R^i$, independently of each other, are selected from the group consisting of $C_3$-$C_{12}$-alkyl, cyclohexyl, adamantyl, phenyl, phenoxy and indolyl, where the phenyl moiety in phenyl and phenoxy and the indolyl radical may carry 1, 2 or 3 substituents selected from the group consisting of $C_1$-$C_6$-alkyl and $C_1$-$C_4$-alkoxy.

16. The process as claimed in claim 1, where the catalyst is produced by bringing the transition metal or a salt thereof and the ligand in a molar ratio of from 10:1 to 1:100 into contact with each other.

17. The process as claimed in claim 1, where the catalyst is used in such an amount that the metal is present in an amount of 0.001 to 10 mol-%, relative to 100 mol-% of compound II.

18. The process as claimed in claim 1, where reaction is carried out at 1 to 100 bar.

19. The process as claimed in claim 1, where reaction is carried out at 50 to 170° C.

20. The process as claimed in claim 1, where reaction is carried out in the presence of a base.

21. The process as claimed in claim 20, where the base is selected from the group consisting of aliphatic mono and polyamines, aromatic amines, alkanol amines, nitrogen-containing heterocyclic compounds and inorganic bases.

22. The process as claimed in claim 20 where the base is used in an amount of 0.1 to 10 mole equivalents, relative to 1 mole of compound II.

23. The process as claimed in claim 1, where X is trifluoromethyl.

24. The process as claimed in claim 1, where Y is $NR^3$.

25. The process as claimed in claim 1, where $R^2$ is CO—N$(R^8)R^9$, CS—N$(R^8)R^9$ or CO—$R^6$.

26. The process as claimed in claim 1, where $R^3$ is selected from the group consisting of hydrogen, $C_1$-$C_4$-alkyl, $C_1$-$C_4$-haloalkyl and —C(=O)$R^6$.

27. The process as claimed in claim 26, where $R^3$ is selected from the group consisting of hydrogen, $C_1$-$C_4$-alkyl and $C_1$-$C_4$-haloalkyl.

28. The process as claimed in claim 1, where each $R^4$ is independently selected from the group consisting of Cl, F; cyano; $C_1$-$C_6$-alkyl, fluorinated $C_1$-$C_6$-alkyl, $C_1$-$C_6$-alkoxy and fluorinated $C_1$-$C_6$-alkoxy or two radicals $R^4$ bound on adjacent carbon atoms form together a group —CH=CH—CH=CH—.

29. The process as claimed in claim 2, where each $R^5$ is independently selected from the group consisting of Cl, F and fluorinated $C_1$-$C_2$-alkyl.

30. The process as claimed in claim 29, where each $R^5$ is independently selected from the group consisting of chlorine and fluorine.

31. The process as claimed in claim 2, where Z is Br, I or —OSO$_2$—$R^{z1}$, where $R^{z1}$ is selected from the group consisting of $CH_3$, $CF_3$ and 4-methylphenyl.

* * * * *